United States Patent
Salome et al.

(10) Patent No.: US 8,916,176 B2
(45) Date of Patent: Dec. 23, 2014

(54) MODIFIED PARVOVIRUS HAVING ENHANCED ANTI-TUMOR EFFICACY

(71) Applicant: Deutsches Krebsforschungszentrum, Heidelberg (DE)

(72) Inventors: Nathalie Salome, Dossenheim (DE); Christiane Dinsart, Ladenburg (DE); Nadine Michel, Dossenheim (DE); Jean Rommelaere, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 13/713,889

(22) Filed: Dec. 13, 2012

(65) Prior Publication Data

US 2013/0189265 A1   Jul. 25, 2013

Related U.S. Application Data

(63) Continuation of application No. PCT/EP2011/003021, filed on Jun. 17, 2011.

(30) Foreign Application Priority Data

Jun. 17, 2010 (EP) .................................... 10166332

(51) Int. Cl.
| | |
|---|---|
| *A61K 39/12* | (2006.01) |
| *A61K 39/23* | (2006.01) |
| *A61K 39/235* | (2006.01) |
| *C12N 7/00* | (2006.01) |
| *A61K 35/76* | (2006.01) |
| *C12N 15/86* | (2006.01) |
| *C07K 14/005* | (2006.01) |
| *C07K 16/08* | (2006.01) |

(52) U.S. Cl.
CPC ................ *C12N 7/00* (2013.01); *A61K 35/768* (2013.01); *C12N 2750/14332* (2013.01); *C12N 2750/14343* (2013.01); *C12N 15/86* (2013.01); *C12N 2750/14322* (2013.01); *C07K 14/005* (2013.01); *C07K 16/081* (2013.01)
USPC ................................... 424/233.1; 424/186.1

(58) Field of Classification Search
None
See application file for complete search history.

(56) References Cited

U.S. PATENT DOCUMENTS 6,491,907 B1 * 12/2002 Rabinowitz et al. ......... 424/93.2
2006/0223775 A1 * 10/2006 Zeicher ........................ 514/44

OTHER PUBLICATIONS

Brown et al., "Production of Recombinant Parvovirus Stocks Devoid of Replication-Competent Viruses," Human Gene Therapy, 13: pp. 2135-2145 (2002).*

(Continued)

*Primary Examiner* — Michelle S Horning
*Assistant Examiner* — M. Franco Salvoza
(74) *Attorney, Agent, or Firm* — Perkins Coie LLP; Viola T. Kung

(57) ABSTRACT

Described are parvovirus variants derived, e.g., from H-1PV, showing higher anti-tumor potential compared to the wild type parvovirus, wherein said variant is characterized by (a) an amino acid substitution, alteration or addition, preferably substitution at position Lys96 of NS-2 and/or position Leu103 of NS-2 (together with a amino acid substitution at position Tyr595 of NS-1 in the latter case), or (b) an in-frame deletion in the parvovirus genome, preferably a deletion resulting in a large amino acid deletion in both the central part (aa 96-133) of NS-2 and the C-terminal part (aa 587-624) of NS-1. The present invention also relates to the use of said parvovirus variants for cancer therapy.

9 Claims, 30 Drawing Sheets

(56) References Cited

OTHER PUBLICATIONS

Ponnazhagan, "Parvovirus vectors for cancer gene therapy," Expert Opin. Biol. Ther (4)(1): pp. 53-64 (2004).*

Rommelaere et al., "Oncolytic parovoviruses as cancer therapeutics," Cytokine & Growth Factor Reviews, 21: pp. 185-195 (2010).*

International Search Report and Written Opinion of International Application No. PCT/EP2011/003021 with a mailing date of Mar. 5, 2012.

Daeffler Laurent et al.; "Modulation of Minute Virus of Mice Cytotoxic Activities Through Site-Directed Mutagenesis Within the NS Coding Region"; Journal of Virology; vol. 77, No. 23, pp. 12466-12478 (Dec. 2003).

Faisst S. et al.; "Isolation of a Fully Infectious Variant of Parvovirus H-1 Supplanting the Standard Strain in Human Cells"; Journal of Virology; vol. 69, No. 7, pp. 4538-4543 (Jul. 1995).

Lopez-Bueno Alberto, et al.; "Enhanced Cytoplasmic Sequestration of the Nuclear Export Receptor CRM1 by NS2 Mutations Developed in the Host Regulates Parvovirus Fitness"; Journal of Virology; vol. 78, No. 19, pp. 10674-10684 (Oct. 2004).

Moehler M. et al.; "Effective Infection, Apoptotic Cell Killing and Gene Transfer of Human Hepatoma Cells But Not Primary Hepatocytes by Parvovirus H1 and Derived Vectors"; vol. 8, No. 3, pp. 158-167 (Jan. 1, 2001).

* cited by examiner

D- pPMut4H-1PV

E- pDelH-1PV

Figure 2

|  | P/I – ratio 1 Full particles PFU | P/I – ratio 2 Full particles RU |
|---|---|---|
| wt H-1 PV | 1050 | 3438 |
| Del H-1 PV | 223 | 566 |
| PMut1 H-1PV | 139 | 151 |
| PMut2 H-1PV | 207 | 189 |
| PMut3 H-1PV | 2125 | 1932 |
| PMut4 H-1PV | 2351 | 5000 |

A- Growth inhibition of infected NB-324K cells

B- Kinetics of virus production in infected NB-324K cells a)

b)

c)

d)

A- wt H-1PV

Del H-1PV

H-1PV complete genome sequence (in nucleotides)(SEQ ID NO:11)
&
H-1PV NS1 (SEQ ID NO:12), NSs (NS2P (SEQ ID NO:13), NS2Y (SEQ ID NO:14), VP1 (SEQ ID NO:15) and VP2 (SEQ ID NO:16) protein sequences (in amino acids)

```
CATTTTTAGAACTGACCAACCATGTTCACGCAAGTGACGTGATGACGCGCGCTGCGCGCG        nt 60

CTGCCTTCGGCAGTCACACGTCACTAGCGTTTCACATGGTTGGTCAGTTCTAAAAATGAT        nt 120

AAGCGGTTCAGAGAGTTTGAAACCAAGGCGGGAAACGGAAGTGGGCGTGGCTAACTGTAT        nt 180

ATAAGCAGTCACTCTGGTCGGTTACTCACTCTGCTTTCATTTCTGAGTTTGTGAGACACA        nt 240

GGAGCGAGACTAACCAACTAACCATGGCTGGAAACGCTTACTCCGATGAGGTTTTGGGAG        nt 300
                             M  A  G  N  A  Y  S  D  E  V  L  G  V     aa 13 NS1
                             M  A  G  N  A  Y  S  D  E  V  L  G  V     aa 13 NS2

TAACCAACTGGCTGAAGGACAAAAGTAGCCAGGAGGTGTTCTCATTTGTTTTTAAAAATG        nt 360
 T  N  W  L  K  D  K  S  S  Q  E  V  F  S  F  V  F  K  N  E           aa 33 NS1
 T  N  W  L  K  D  K  S  S  Q  E  V  F  S  F  V  F  K  N  E           aa 33 NS2

AAAACGTCCAACTAAATGGAAAGGACATCGGTTGGAATAGTTACAGAAAGGAGCTACAAG        nt 420
 N  V  Q  L  N  G  K  D  I  G  W  N  S  Y  R  K  E  L  Q  D           aa 53 NS1
 N  V  Q  L  N  G  K  D  I  G  W  N  S  Y  R  K  E  L  Q  D           aa 53 NS2

ATGACGAGCTGAAGTCTCTACAACGAGGGGCGGAGACCACTTGGGACCAAAGCGAGGACA        nt 480
 D  E  L  K  S  L  Q  R  G  A  E  T  T  W  D  Q  S  E  D  M           aa 73 NS1
 D  E  L  K  S  L  Q  R  G  A  E  T  T  W  D  Q  S  E  D  M           aa 73 NS2

TGGAATGGGAGAGCGCAGTGGATGACATGACCAAAAAGCAAGTATTTATTTTTGATTCTT        nt 540
 E  W  E  S  A  V  D  D  M  T  K  K  Q  V  F  I  F  D  S  L           aa 93 NS1
 E  W  E  S  A  V  D  D  M  T  K  K                                   aa 85 NS2
```

Figure 11-2

```
TGGTTAAGAAGTGTTTGTTTGAAGTGCTCAGCACAAAGAACATAGCTCCTAGTAATGTTA    nt 600
  V  K  K  C  L  F  E  V  L  S  T  K  N  I  A  P  S  N  V  T   aa 113 NS1

CTTGGTTCGTGCAGCATGAATGGGGAAAGGACCAAGGCTGGCACTGTCATGTGCTGATTG    nt 660
  W  F  V  Q  H  E  W  G  K  D  Q  G  W  H  C  V  L  I  G      aa 133 NS1

GAGGCAAGGACTTTAGTCAACCTCAAGGAAAATGGTGGAGAAGGCAGCTAAATGTGTACT    nt 720
  G  K  D  F  S  Q  P  Q  G  K  W  W  R  R  Q  L  N  V  Y  W   aa 153 NS1

GGAGTAGATGGTTGGTGACTGCCTGTAATGTTCAACTAACACCAGCTGAAAGAATTAAAC    nt 780
  S  R  W  L  V  T  A  C  N  V  Q  L  T  P  A  E  R  I  K  L   aa 173 NS1

TGAGAGAAATAGCAGAGGACAGTGAATGGGTCACTTTGCTTACCTATAAGCATAAGCACA    nt 840
  R  E  I  A  E  D  S  E  W  V  T  L  L  T  Y  K  H  K  H  T   aa 193 NS1

CCAAGAAGGACTATACCAAGTGTGTTCTTTTTGGAAACATGATTGCTTATTACTTTTTAA    nt 900
  K  K  D  Y  T  K  C  V  L  F  G  N  M  I  A  Y  Y  F  L  S   aa 213 NS1

GCAAAAAGAAAATATGTACCAGTCCACCAAGGGACGGAGGCTATTTTCTTAGCAGTGACT    nt 960
  K  K  K  I  C  T  S  P  P  R  D  G  G  Y  F  L  S  S  D  S   aa 233 NS1

CTGGCTGGAAAACTAACTTTTTGAAAGAGGGCGAGCGCCATCTAGTGAGCAAACTGTATA    nt 1020
  G  W  K  T  N  F  L  K  E  G  E  R  H  L  V  S  K  L  Y  T   aa 253 NS1

CTGATGAGATGAAACCAGAAACGGTCGAGACCACAGTGACCACTGCACAGGAAGCTAAGC    nt 1080
  D  E  M  K  P  E  T  V  E  T  T  V  T  T  A  Q  E  A  K  R   aa 273 NS1

GCGGCAGAATTCAAACTAGAAAGGAGGTCTCGATTAAAACCACACTCAAAGAGTTGGTAC    nt 1140
  G  R  I  Q  T  R  K  E  V  S  I  K  T  T  L  K  E  L  V  H   aa 293 NS1

ATAAAAGAGTAACCTCACCAGAAGACTGGATGATGATGCAGCCAGACAGTTACATTGAAA    nt 1200
  K  R  V  T  S  P  E  D  W  M  M  M  Q  P  D  S  Y  I  E  M   aa 313 NS1

TGATGGCTCAACCAGGTGGAGAAAACTTGCTTAAAAATACACTAGAGATCTGTACACTGA    nt 1260
  M  A  Q  P  G  G  E  N  L  L  K  N  T  L  E  I  C  T  L  T   aa 333 NS1
```

Figure 11-3

```
CTCTAGCAAGAACCAAAACAGCCTTTGACTTGATTCTGGAAAAAGCTGAAACCAGCAAAC    nt 1320
  L   A   R   T   K   T   A   F   D   L   I   L   E   K   A   E   T   S   K   L     aa 353 NS1

TAGCCAACTTTTCCATGGCTAGCACCAGAACCTGTAGAATCTTTGCTGAGCATGGCTGGA    nt 1380
  A   N   F   S   M   A   S   T   R   T   C   R   I   F   A   E   H   G   W   N     aa 373 NS1

ACTATATTAAAGTCTGCCATGCCATCTGTTGTGTGCTAATAGACAAGGAGGCAAAAGGA     nt 1440
  Y   I   K   V   C   H   A   I   C   C   V   L   N   R   Q   G   G   K   R   N     aa 393 NS1

ACACTGTGCTCTTTCACGGACCAGCCAGCACAGGCAAATCTATTATTGCACAAGCCATAG    nt 1500
  T   V   L   F   H   G   P   A   S   T   G   K   S   I   I   A   Q   A   I   A     aa 413 NS1

CACAAGCAGTTGGTAATGTTGGTTGTTACAATGCTGCCAATGTGAACTTTCCATTTAATG    nt 1560
  Q   A   V   G   N   V   G   C   Y   N   A   A   N   V   N   F   P   F   N   D     aa 433 NS1

ACTGTACCAACAAAAACTTGATTTGGGTGGAAGAAGCTGGTAACTTTGGCCAGCAAGTAA    nt 1620
  C   T   N   K   N   L   I   W   V   E   E   A   G   N   F   G   Q   Q   V   N     aa 453 NS1

ACCAATTCAAAGCTATTTGTTCTGGCCAAACCATACGCATTGATCAAAAAGGAAAAGGCA   nt 1680
  Q   F   K   A   I   C   S   G   Q   T   I   R   I   D   Q   K   G   K   G   S     aa 473 NS1

GCAAACAGATTGAACCAACACCAGTTATTATGACCACCAACGAGAACATTACCGTGGTTA    nt 1740
  K   Q   I   E   P   T   P   V   I   M   T   T   N   E   N   I   T   V   V   R     aa 493 NS1

GAATAGGCTGTGAGGAAAGACCAGAACACACTCAACCAATCAGAGACAGAATGCTCAACA    nt 1800
  I   G   C   E   E   R   P   E   H   T   Q   P   I   R   D   R   M   L   N   I     aa 513 NS1

TTCACCTGACACGTACACTACCTGGTGACTTTGGTTTGGTGGATAAGCACGAATGGCCTC   nt 1860
  H   L   T   R   T   L   P   G   D   F   G   L   V   D   K   H   E   W   P   L     aa 533 NS1

TGATCTGTGCTTGGTTGGTGAAGAATGGTTACCAATCTACCATGGCTTGTTACTGTGCTA    nt 1920
  I   C   A   W   L   V   K   N   G   Y   Q   S   T   M   A   C   Y   C   A   K     aa 553 NS1

AATGGGGCAAAGTTCCTGATTGGTCAGAGGACTGGGCGGAGCCGAAGCTAGACACTCCTA    nt 1980
  W   G   K   V   P   D   W   S   E   D   W   A   E   P   K   L   D   T   P   I     aa 573 NS1
```

Figure 11-4

```
TAAATTCGCTAGGTTCAATGCGCTCACCATCTCTGACTCCGAGAAGTACGCCTCTCAGCC    nt 2040
  N  S  L  G  S  M  R  S  P  S  L  T  P  R  S  T  P  L  S  Q    aa 593 NS1
           F  N  A  L  T  I  S  D  S  E  K  Y  A  S  Q  P       aa 101 NS2

AAAACTACGCTCTTACTCCACTTGCATCGGACCTTGCGGACCTAGCTCTAGAGCCTTGGA    nt 2100
  N  Y  A  L  T  P  L  A  S  D  L  A  D  L  A  L  E  P  W  S    aa 613 NS1
  K  L  R  S  Y  S  T  C  I  G  P  C  G  P  S  S  R  A  L  E    aa 121 NS2

GCACACCAAATACTCCTGTTGCGGGCACTGCAGCAAGCCAAAACACTGGGGAGGCTGGTT    nt 2160
  T  P  N  T  P  V  A  G  T  A  A  S  Q  N  T  G  E  A  G  S    aa 633 NS1
  H  T  K  Y  S  C  C  G  H  C  S  K  P  K  H  W  G  G  W  F    aa 141 NS2

CCACAGCCTGCCAAGGTGCTCAACGGAGCCCAACCTGGTCCGAGATCGAGGCGGATTTGA    nt 2220
  T  A  C  Q  G  A  Q  R  S  P  T  W  S  E  I  E  A  D  L  R    aa 653 NS1
  H  S  L  P  R  C  S  T  E  P  N  L  V  R  D  R  G  G  F  E    aa 161 NS2

GAGCTTGCTTCAGTCAAGAACAGTTGGAGAGCGACTTCAACGAGGAGCTGACCTTGGACT    nt 2280
  A  C  F  S  Q  E  Q  L  E  S  D  F  N  E  E  L  T  L  D  *    aa 672 NS1
  S  L  L  Q  S  R  T  V  G  E  R  L  Q  R  G  A  D  L  G  L    aa 181 NS2

AAGGTACAATGGCACCTCCAGCTAAAAGAGCTAAAAGAGGTAAGGGGCTAAGGGATGGTT    nt 2340
        R  Y  N  G  T  S  S  *                                   aa 188
NS2Y
              M  A  P  P  A  K  R  A  K  R  G                    aa 11 VP1

GGTTGGTGGGGTACTAATGTATGACTACCTGTTTTACAGGCCTGAAATCACTTGGTTCTA    nt 2400
                                         P  E  I  T  W  F  *     aa 188
NS2P

GGTTGGGTGCCTCCTGGCTACAAGTACCTGGGACCAGGGAACAGCCTTGACCAAGGAGAA    nt 2460
  W  V  P  P  G  Y  K  Y  L  G  P  G  N  S  L  D  Q  G  E       aa 30 VP1

CCAACCAACCCTTCTGACGCCGCTGCCAAAGAACACGACGAAGCCTACGACCAATACATC    nt 2520
  P  T  N  P  S  D  A  A  A  K  E  H  D  E  A  Y  D  Q  Y  I    aa 50 VP1

AAATCTGGAAAAAATCCTTACCTGTACTTCTCTCCTGCTGATCAACGCTTCATTGACCAA    nt 2580
  K  S  G  K  N  P  Y  L  Y  F  S  P  A  D  Q  R  F  I  D  Q    aa 70 VP1
```

Figure 11-5

```
ACCAAAGACGCCAAGGACTGGGGCGGCAAGGTTGGTCACTACTTTTTAGAACCAAGCGA    nt 2640
 T  K  D  A  K  D  W  G  G  K  V  G  H  Y  F  F  R  T  K  R    aa 90 VP1

GCTTTTGCACCTAAGCTTTCTACTGACTCTGAACCTGGCACTTCTGGTGTGAGCAGACCT    nt 2700
 A  F  A  P  K  L  S  T  D  S  E  P  G  T  S  G  V  S  R  P    aa 110 VP1

GGTAAACGAACTAAACCACCTGCTCACATTTTTGTAAATCAAGCCAGAGCTAAAAAAAAA    nt 2760
 G  K  R  T  K  P  P  A  H  I  F  V  N  Q  A  R  A  K  K  K    aa 130 VP1

CGCGCTTCTCTTGCTGCACAGCAGAGGACTCTGACAATGAGTGATGGCACCGAAACAAAC    nt 2820
 R  A  S  L  A  A  Q  Q  R  T  L  T  M  S  D  G  T  E  T  N    aa 150 VP1
                                        M  S  D  G  T  E  T  N    aa 8 VP2

CAACCAGACACTGGAATCGCTAATGCTAGAGTTGAGCGATCAGCTGACGGAGGTGGAAGC    nt 2880
 Q  P  D  T  G  I  A  N  A  R  V  E  R  S  A  D  G  G  S       aa 170 VP1
 Q  P  D  T  G  I  A  N  A  R  V  E  R  S  A  D  G  G  S       aa 28 VP2

TCTGGGGGTGGGGGCTCTGGCGGGGGTGGGATTGGTGTTTCTACTGGGACTTATGATAAT    nt 2940
 S  G  G  G  S  G  G  G  G  I  G  V  S  T  G  T  Y  D  N       aa 190 VP1
 S  G  G  G  S  G  G  G  G  I  G  V  S  T  G  T  Y  D  N       aa 48 VP2

CAAACGACTTATAAGTTTTTGGGAGATGGATGGGTAGAAATAACTGCACATGCTTCTAGA    nt 3000
 Q  T  T  Y  K  F  L  G  D  G  W  V  E  I  T  A  H  A  S  R    aa 210 VP1
 Q  T  T  Y  K  F  L  G  D  G  W  V  E  I  T  A  H  A  S  R    aa 68 VP2

CTTTTGCACTTGGGAATGCCTCCTTCAGAAAACTACTGCCGCGTCACCGTTCACAATAAT    nt 3060
 L  L  H  L  G  M  P  P  S  E  N  Y  C  R  V  T  V  H  N  N    aa 230 VP1
 L  L  H  L  G  M  P  P  S  E  N  Y  C  R  V  T  V  H  N  N    aa 88 VP2

CAAACAACAGGACACGGAACTAAGGTAAAGGGAAACATGGCCTATGACACACATCAACAA    nt 3120
 Q  T  T  G  H  G  T  K  V  K  G  N  M  A  Y  D  T  H  Q  Q    aa 250 VP1
 Q  T  T  G  H  G  T  K  V  K  G  N  M  A  Y  D  T  H  Q  Q    aa 108 VP2

ATTTGGACACCATGGAGCTTGGTAGATGCTAATGCTTGGGGAGTTTGGTTCCAACCAAGT    nt 3180
 I  W  T  P  W  S  L  V  D  A  N  A  W  G  V  W  F  Q  P  S    aa 270 VP1
 I  W  T  P  W  S  L  V  D  A  N  A  W  G  V  W  F  Q  P  S    aa 128 VP2
```

Figure 11-6

```
GACTGGCAGTTCATTCAAAACAGCATGGAATCGCTGAATCTTGACTCATTGAGCCAAGAA    nt 3240
 D   W   Q   F   I   Q   N   S   M   E   S   L   N   L   D   S   L   S   Q   E     aa 290 VP1
 D   W   Q   F   I   Q   N   S   M   E   S   L   N   L   D   S   L   S   Q   E     aa 148 VP2

CTATTTAATGTAGTAGTCAAAACAGTCACTGAACAACAAGGAGCTGGCCAAGATGCCATT    nt 3300
 L   F   N   V   V   V   K   T   V   T   E   Q   Q   G   A   G   Q   D   A   I     aa 310 VP1
 L   F   N   V   V   V   K   T   V   T   E   Q   Q   G   A   G   Q   D   A   I     aa 168 VP2

AAAGTCTATAATAATGACTTGACGGCCTGTATGATGGTTGCTCTGGATAGTAACAACATA    nt 3360
 K   V   Y   N   N   D   L   T   A   C   M   M   V   A   L   D   S   N   N   I     aa 330 VP1
 K   V   Y   N   N   D   L   T   A   C   M   M   V   A   L   D   S   N   N   I     aa 188 VP2

CTGCCTTACACACCTGCAGCTCAAACATCAGAAACACTTGGTTTCTACCCATGGAAACCA    nt 3420
 L   P   Y   T   P   A   A   Q   T   S   E   T   L   G   F   Y   P   W   K   P     aa 350 VP1
 L   P   Y   T   P   A   A   Q   T   S   E   T   L   G   F   Y   P   W   K   P     aa 208 VP2

ACCGCACCAGCTCCTTACAGATACTACTTTTTCATGCCTAGACAACTCAGTGTAACCTCT    nt 3480
 T   A   P   A   P   Y   R   Y   Y   F   F   M   P   R   Q   L   S   V   T   S     aa 370 VP1
 T   A   P   A   P   Y   R   Y   Y   F   F   M   P   R   Q   L   S   V   T   S     aa 228 VP2

AGCAACTCTGCTGAAGGAACTCAAATCACAGACACCATTGGAGAGCCACAGGCACTAAAC    nt 3540
 S   N   S   A   E   G   T   Q   I   T   D   T   I   G   E   P   Q   A   L   N     aa 390 VP1
 S   N   S   A   E   G   T   Q   I   T   D   T   I   G   E   P   Q   A   L   N     aa 248 VP2

TCTCAATTTTTTACTATTGAGAACACCTTGCCTATTACTCTCCTGCGCACAGGTGATGAG    nt 3600
 S   Q   F   F   T   I   E   N   T   L   P   I   T   L   L   R   T   G   D   E     aa 410 VP1
 S   Q   F   F   T   I   E   N   T   L   P   I   T   L   L   R   T   G   D   E     aa 268 VP2

TTTACAACTGGCACCTACATCTTTAACACTGACCCACTTAAACTTACTCACACATGGCAA    nt 3660
 F   T   T   G   T   Y   I   F   N   T   D   P   L   K   L   T   H   T   W   Q     aa 430 VP1
 F   T   T   G   T   Y   I   F   N   T   D   P   L   K   L   T   H   T   W   Q     aa 288 VP2

ACCAACAGACACTTGGCATGCCTCCAAGGAATAACTGACCTACCAACATCAGATACAGCA    nt 3720
 T   N   R   H   L   A   C   L   Q   G   I   T   D   L   P   T   S   D   T   A     aa 450 VP1
 T   N   R   H   L   A   C   L   Q   G   I   T   D   L   P   T   S   D   T   A     aa 308 VP2

ACAGCATCACTAACTGCAAATGGAGACAGATTTGGATCAACACAAACACAGAATGTGAAC    nt 3780
 T   A   S   L   T   A   N   G   D   R   F   G   S   T   Q   T   Q   N   V   N     aa 470 VP1
 T   A   S   L   T   A   N   G   D   R   F   G   S   T   Q   T   Q   N   V   N     aa 328 VP2
```

Figure 11-7

```
TATGTCACAGAGGCTTTGCGCACCAGGCCTGCTCAGATTGGCTTCATGCAACCTCATGAC    nt 3840
Y   V   T   E   A   L   R   T   R   P   A   Q   I   G   F   M   Q   P   H   D       aa 490 VP1
Y   V   T   E   A   L   R   T   R   P   A   Q   I   G   F   M   Q   P   H   D       aa 348 VP2

AACTTTGAAGCAAACAGAGGTGGCCCATTTAAGGTTCCAGTGGTACCGCTAGACATAACA    nt 3900
N   F   E   A   N   R   G   G   P   F   K   V   P   V   V   P   L   D   I   T       aa 510 VP1
N   F   E   A   N   R   G   G   P   F   K   V   P   V   V   P   L   D   I   T       aa 368 VP2

GCTGGCGAGGACCATGATGCAAACGGAGCCATACGATTTAACTATGGCAAACAACATGGC    nt 3960
A   G   E   D   H   D   A   N   G   A   I   R   F   N   Y   G   K   Q   H   G       aa 530 VP1
A   G   E   D   H   D   A   N   G   A   I   R   F   N   Y   G   K   Q   H   G       aa 388 VP2

GAAGATTGGGCCAAACAAGGAGCAGCACCAGAAAGGTACACATGGGATGCAATTGATAGT    nt 4020
E   D   W   A   K   Q   G   A   A   P   E   R   Y   T   W   D   A   I   D   S       aa 550 VP1
E   D   W   A   K   Q   G   A   A   P   E   R   Y   T   W   D   A   I   D   S       aa 408 VP2

GCAGCTGGGAGGGACACAGCTAGATGCTTTGTACAAAGTGCACCAATATCTATTCCACCA    nt 4080
A   A   G   R   D   T   A   R   C   F   V   Q   S   A   P   I   S   I   P   P       aa 570 VP1
A   A   G   R   D   T   A   R   C   F   V   Q   S   A   P   I   S   I   P   P       aa 428 VP2

AACCAAAACCAGATCTTGCAGCGAGAAGACGCCATAGCTGGCAGAACTAACATGCATTAT    nt 4140
N   Q   N   Q   I   L   Q   R   E   D   A   I   A   G   R   T   N   M   H   Y       aa 590 VP1
N   Q   N   Q   I   L   Q   R   E   D   A   I   A   G   R   T   N   M   H   Y       aa 448 VP2

ACTAATGTTTTTAACAGCTATGGTCCACTTAGTGCATTTCCTCATCCAGATCCCATTTAT    nt 4200
T   N   V   F   N   S   Y   G   P   L   S   A   F   P   H   P   D   P   I   Y       aa 610 VP1
T   N   V   F   N   S   Y   G   P   L   S   A   F   P   H   P   D   P   I   Y       aa 468 VP2

CCAAATGGACAAATTTGGGACAAAGAATTGGACCTGGAACACAAACCTAGACTACACGTA    nt 4260
P   N   G   Q   I   W   D   K   E   L   D   L   E   H   K   P   R   L   H   V       aa 630 VP1
P   N   G   Q   I   W   D   K   E   L   D   L   E   H   K   P   R   L   H   V       aa 488 VP2

ACTGCACCATTTGTTTGTAAAAACAACCCACCAGGTCAACTATTTGTTCACTTGGGGCCT    nt 4320
T   A   P   F   V   C   K   N   N   P   P   G   Q   L   F   V   H   L   G   P       aa 650 VP1
T   A   P   F   V   C   K   N   N   P   P   G   Q   L   F   V   H   L   G   P       aa 508 VP2
```

Figure 11-8

```
AATCTGACTGACCAATTTGACCCAAACAGCACAACTGTTTCTCGCATTGTTACATATAGC    nt 4380
 N  L  T  D  Q  F  D  P  N  S  T  T  V  S  R  I  V  T  Y  S     aa 670 VP1
 N  L  T  D  Q  F  D  P  N  S  T  T  V  S  R  I  V  T  Y  S     aa 528 VP2

ACTTTTTACTGGAAGGGTATTTTGAAATTCAAAGCCAAACTAAGACCAAATCTGACCTGG    nt 4440
 T  F  Y  W  K  G  I  L  K  F  K  A  K  L  R  P  N  L  T  W     aa 690 VP1
 T  F  Y  W  K  G  I  L  K  F  K  A  K  L  R  P  N  L  T  W     aa 548 VP2

AATCCTGTATACCAAGCAACCACAGACTCTGTTGCCAATTCTTACATGAATGTTAAGAAA    nt 4500
 N  P  V  Y  Q  A  T  T  D  S  V  A  N  S  Y  M  N  V  K  K     aa 710 VP1
 N  P  V  Y  Q  A  T  T  D  S  V  A  N  S  Y  M  N  V  K  K     aa 568 VP2

TGGCTCCCATCTGCAACTGGCAACATGCACTCTGATCCATTGATTTGTAGACCTGTGCCT    nt 4560
 W  L  P  S  A  T  G  N  M  H  S  D  P  L  I  C  R  P  V  P     aa 730 VP1
 W  L  P  S  A  T  G  N  M  H  S  D  P  L  I  C  R  P  V  P     aa 588 VP2

CACATGACATACTAACCAACCAACTATGTTTCTCTGTTTGCTTCACATAATACTTAAACT    nt 4620
 H  M  T  Y  *                                                  aa 734 VP1
 H  M  T  Y  *                                                  aa 592 VP2

AACTAGACTACAACATAAAAATATACACTTAATAATAGATTATTAAAAATAACATAATAT    nt 4680

GGTAGGTTAACTGTAAAAAATAATAGAACTTTTGGAATAAATATAGTTAGTTGGTTAATG    nt 4740

TTAGATAGAATATAAAAAGATTTTGTATTTTAAAATAAATATAGTTAGTTGGTTAATGTT    nt 4800

AGATAGAATATAAAAAGATTTTGTATTTGGGAAATAAAAAGGGTGGTTGGGTGGTTGGTT    nt 4860

GGTACTCCCTTAGACTGAATGTTAGGGACCAAAAAAATAATAAAATAATTAAAATGAACA    nt 4920

AGGACTACTGTCTATTCAGTTGACCAACTGAACCTATAGTATCACTATGTTTTTAGGGTG    nt 4980

GGGGGGTGGGAGATACATACGTTCGCTATGGACCAAGTGGTACCGGTTGGTTGCTAAGCT    nt 5040
```

Figure 11-9

```
CGAACAAGACGGCTAAGCCGGTCCGGTTGGTTGAGCGCAACCAACCGGTACCACTTGGTC    nt 5100

CATAGCGAACGTATGTATCTCCCACCCCCCCACCCTAAAAACATAGTGATACTATAGGTT    nt 5160

CAGTTGGTCAACTGAA                                                nt 5176
```

| transfection | pfu / ml | vg / ml | P / I -ratio | wt / del |
|---|---|---|---|---|
| phH-1 | $2.82 \times 10^8$ | $4.58 \times 10^{11}$ | 1624 | |
| pdelhH-1 | $2.17 \times 10^9$ | $6.06 \times 10^{11}$ | 279 | 5.8 |
| pwtH-1 | $9.80 \times 10^8$ | $1.46 \times 10^{11}$ | 149 | |
| pdelH-1 | $2.18 \times 10^{10}$ | $7.29 \times 10^{11}$ | 33 | 4.5 |

SEQUENCE LISTING

```
<160> NUMBER OF SEQ ID NOS: 16

<210> SEQ ID NO 1
<211> LENGTH: 71
<212> TYPE: DNA
<213> ORGANISM: artificial sequences
<220> FEATURE:
<221> NAME/KEY: source
<222> LOCATION: 1..71
<223> OTHER INFORMATION: /mol_type="DNA"
      /note="primer"
      /organism="artificial sequences"

<400> SEQUENCE: 1
ctataaattc gctaggttca atgcgctcac catctctgac tccgagccaa aacactgggg      60
aggctggttc c                                                          71

<210> SEQ ID NO 2
<211> LENGTH: 28
<212> TYPE: DNA
```

```
<213> ORGANISM: artificial sequences
<220> FEATURE:
<221> NAME/KEY: source
<222> LOCATION: 1..28
<223> OTHER INFORMATION: /mol_type="DNA"
      /note="primer"
      /organism="artificial sequences"

<400> SEQUENCE: 2
gaaagcttag gtgcaaaagc tcgcttgg                                              28

<210> SEQ ID NO 3
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="primer"
      /organism="artificial sequences"

<400> SEQUENCE: 3
cgcctctcag ccaaaaccac gctcttactc cac                                        33

<210> SEQ ID NO 4
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="primer"
      /organism="artificial sequences"

<400> SEQUENCE: 4
gtggagtaag agcgtggttt tggctgagag gcg                                        33

<210> SEQ ID NO 5
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="primer"
      /organism="artificial sequences"

<400> SEQUENCE: 5
atctctgact ccgaggagta cgcctctcag c                                          31

<210> SEQ ID NO 6
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="primer"
      /organism="artificial sequences"

<400> SEQUENCE: 6
gctgagaggc gtactcctcg gagtcagaga t                                          31

<210> SEQ ID NO 7
<211> LENGTH: 29
```

```
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="primer"
      /organism="artificial sequences"

<400> SEQUENCE: 7
caacggagcc caacatggtc cgagatcga                              29

<210> SEQ ID NO 8
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="primer"
      /organism="artificial sequences"

<400> SEQUENCE: 8
tcgatctcgg accatgttgg gctccgttg                              29

<210> SEQ ID NO 9
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="primer"
      /organism="artificial sequences"

<400> SEQUENCE: 9
atctctgact ccgaggagta cgcctctcag c                           31

<210> SEQ ID NO 10
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="primer"
      /organism="artificial sequences"

<400> SEQUENCE: 10
gctgagaggc gtactcctcg gagtcagaga t                           31

<210> SEQ ID NO 11
<211> LENGTH: 5176
<212> TYPE: DNA
<213> ORGANISM: Parvovirus
<220> FEATURE:
<221> NAME/KEY: source
<222> LOCATION: 1..5176
<223> OTHER INFORMATION: /mol_type="DNA"
      /note="SEQ ID NO:11"
      /organism="Parvovirus"

<400> SEQUENCE: 11
cattttagaa actgaccaac catgttcacg caagtgacgt gatgacgcgc gctgcgcgcg    60
ctgccttcgg cagtcacacg tcactagcgt ttcacatggt tggtcagttc taaaaatgat   120
```

```
aagcggttca gagagtttga aaccaaggcg ggaaacggaa gtgggcgtgg ctaactgtat      180
ataagcagtc actctggtcg gttactcact ctgctttcat ttctgagttt gtgagacaca      240
ggagcgagac taaccaacta accatggctg aaacgcttta ctccgatgag gttttgggag      300
taaccaactg gctgaaggac aaaagtagcc aggaggtgtt ctcatttgtt tttaaaaatg      360
aaaacgtcca actaaatgga aaggacatcg gttggaatag ttacagaaag gagctacaag      420
atgacgagct gaagtctcta caacgagggg cggagaccac ttgggaccaa agcgaggaca      480
tggaatggga gagcgcagtg gatgacatga ccaaaaagca agtatttatt tttgattctt      540
tggttaagaa gtgtttgttt gaagtgctca gcacaaagaa catagctcct agtaatgtta      600
cttggttcgt gcagcatgaa tggggaaagg accaaggctg gcactgtcat gtgctgattg      660
gaggcaagga ctttagtcaa cctcaaggaa aatggtggag aaggcagcta aatgtgtact      720
ggagtagatg gttggtgact gcctgtaatg ttcaactaac accagctgaa agaattaaac      780
tgagagaaat agcagaggac agtgaatggg tcactttgct tacctataag cataagcaca      840
ccaagaagga ctataccaag tgtgttcttt ttggaaacat gattgcttat tactttttaa      900
gcaaaaagaa aatatgtacc agtccaccaa gggacggagg ctattttctt agcagtgact      960
ctggctggaa aactaacttt ttgaaagagg gcgagcgcca tctagtgagc aaactgtata     1020
ctgatgagat gaaccagaaa acggtcgaga ccacagtgac cactgcacag gaagctaagc     1080
gcggcagaat tcaaactaga aaggaggtct cgattaaaac cacactcaaa gagttggtac     1140
ataaaagagt aacctcacca gaagactgga tgatgatgca gccagacagt tacattgaaa     1200
tgatggctca accaggtgga gaaaacttgc ttaaaaatac actagagatc tgtacactga     1260
ctctagcaag aaccaaaaca gcctttgact tgattctgga aaaagctgaa accagcaaac     1320
tagccaactt ttccatggct agcaccagaa cctgtagaat ctttgctgag catggctgga     1380
actatattaa agtctgccat gccatctgtt gtgtgctgaa tagacaagga ggcaaaagga     1440
acactgtgct ctttcacgga ccagccagca caggcaaatc tattattgca caagccatag     1500
cacaagcagt tggtaatgtt ggttgttaca atgctgccaa tgtgaacttt ccatttaatg     1560
actgtaccaa caaaaacttg atttgggtgg aagaagctgg taactttggc cagcaagtaa     1620
accaattcaa agctatttgt tctggccaaa ccatacgcat tgatcaaaaa ggaaaaggca     1680
gcaaacagat tgaaccaaca ccagttatta tgaccaccaa cgagaacatt accgtggtta     1740
gaataggctg tgaggaaaga ccagaacaca ctcaaccaat cagagacaga atgctcaaca     1800
ttcacctgac acgtacacta cctggtgact ttggttttgt ggataagcac gaatggcctc     1860
tgatctgtgc ttggttggtg aagaatggtt accaatctac catggcttgt tactgtgcta     1920 aatgggcaa agttcctgat tggtcagagg actgggcgga gccgaagcta gacactccta     1980
taaattcgct aggttcaatg cgctcaccat ctctgactcc gagaagtacg cctctcagcc     2040
aaaactacgc tcttactcca cttgcatcgg accttgcgga cctagctcta gagccttgga     2100
gcacaccaaa tactcctgtt gcgggcactg cagcaagcca aaacactggg gaggctggtt     2160
ccacagcctg ccaaggtgct caacggagcc caacctggtc cgagatcgag gcggatttga     2220
gagcttgctt cagtcaagaa cagttggaga gcgacttcaa cgaggagctg acccttggact     2280 aaggtacaat ggcacctcca gctaaagag ctaaagagg taagggcta agggatggtt      2340 ggttggtggg gtactaatgt atgactacct gttttacagg cctgaaatca cttggttcta     2400
ggttgggtgc ctcctggcta caagtacctg ggaccaggga acagccttga ccaaggagaa     2460
ccaaccaacc cttctgacgc cgctgccaaa gaacacgacg aagcctacga ccaatacatc     2520
```

```
aaatctggaa aaaatcctta cctgtacttc tctcctgctg atcaacgctt cattgaccaa    2580
accaaagacg ccaaggactg gggcggcaag gttggtcact acttttttag aaccaagcga    2640
gcttttgcac ctaagctttc tactgactct gaacctggca cttctggtgt gagcagacct    2700
ggtaaacgaa ctaaaccacc tgctcacatt tttgtaaatc aagccagagc taaaaaaaaa    2760
cgcgcttctc ttgctgcaca gcagaggact ctgacaatga gtgatggcac cgaaacaaac    2820
caaccagaca ctggaatcgc taatgctaga gttgagcgat cagctgacgg aggtggaagc    2880
tctgggggtg ggggctctgg cggggtggg  attggtgttt ctactgggac ttatgataat    2940
caaacgactt ataagttttt gggagatgga tgggtagaaa taactgcaca tgcttctaga    3000
cttttgcact tgggaatgcc tccttcagaa aactactgcc gcgtcaccgt tcacaataat    3060
caaacaacag gacacggaac taaggtaaag ggaaacatgg cctatgacac acatcaacaa    3120
atttggacac catggagctt ggtagatgct aatgcttggg gagtttggtt ccaaccaagt    3180
gactggcagt tcattcaaaa cagcatggaa tcgctgaatc ttgactcatt gagccaagaa    3240
ctatttaatg tagtagtcaa aacagtcact gaacaacaag gagctggcca agatgccatt    3300
aaagtctata ataatgactt gacggcctgt atgatggttg ctctggatag taacaacata    3360
ctgccttaca cacctgcagc tcaaacatca gaaacacttg gtttctaccc atggaaacca    3420
accgcaccag ctccttacag atactacttt tcatgccta  gacaactcag tgtaacctct    3480
agcaactctg ctgaaggaac tcaaatcaca gacaccattg gagagccaca ggcactaaac    3540
tctcaatttt ttactattga gaacaccttg cctattactc tcctgcgcac aggtgatgag    3600
tttacaactg gcacctacat ctttaacact gacccactta aacttactca cacatggcaa    3660
accaacagac acttggcatg cctccaagga ataactgacc taccaacatc agatacagca    3720
acagcatcac taactgcaaa tggagacaga tttggatcaa cacaaacaca gaatgtgaac    3780
tatgtcacag aggcttttgcg caccaggcct gctcagattg gcttcatgca acctcatgac    3840
aactttgaag caaacagagg tggcccattt aaggttccag tggtaccgct agacataaca    3900
gctggcgagg accatgatgc aaacggagcc atacgattta actatggcaa acaacatggc    3960
gaagattggg ccaaacaagg agcagcacca gaaaggtaca catgggatgc aattgatagt    4020
gcagctggga gggacacagc tagatgcttt gtacaaagtg caccaatatc tattccacca    4080
aaccaaaacc agatcttgca gcgagaagac gccatagctg gcagaactaa catgcattat    4140
actaatgttt ttaacagcta tggtccactt agtgcatttc ctcatccaga tcccatttat    4200
ccaaatggac aaatttggga caagaattg  gacctggaac acaaacctag actacacgta    4260
actgcaccat ttgtttgtaa aaacaaccca ccaggtcaac tatttgttca cttggggcct    4320
aatctgactg accaatttga cccaaacagc acaactgttt ctcgcattgt tacatatagc    4380 acttttttact ggaagggtat tttgaaattc aaagccaaac taagaccaaa tctgacctgg    4440
aatcctgtat accaagcaac cacagactct gttgccaatt cttacatgaa tgttaagaaa    4500
tggctcccat ctgcaactgg caacatgcac tctgatccat tgatttgtag acctgtgcct    4560
cacatgacat actaaccaac caactatgtt tctctgtttg cttcacataa tacttaaact    4620
aactagacta caacataaaa atatacactt aataatagat tattaaaaat aacataatat    4680
ggtaggttaa ctgtaaaaaa taatagaact tttggaataa atatagttag ttggttaatg    4740
ttagatagaa tataaaaaga ttttgtattt taaaataaat atagttagtt ggttaatgtt    4800
agatagaata taaaaagatt ttgtatttgg gaaataaaaa gggtggttgg gtggttggtt    4860
```

-continued

```
ggtactccct tagactgaat gttagggacc aaaaaaataa taaaataatt aaaatgaaca    4920
aggactactg tctattcagt tgaccaactg aacctatagt atcactatgt ttttagggtg    4980 gggggggtggg agatacatac gttcgctatg gaccaagtgg taccggttgg ttgctaagct    5040
cgaacaagac ggctaagccg gtccggttgg ttgagcgcaa ccaaccggta ccacttggtc    5100
catagcgaac gtatgtatct cccaccccc  caccctaaaa acatagtgat actataggtt    5160
cagttggtca actgaa                                                     5176
```

<210> SEQ ID NO 12
<211> LENGTH: 672
<212> TYPE: PRT
<213> ORGANISM: Parvovirus
<220> FEATURE:
<221> NAME/KEY: SOURCE
<222> LOCATION: 1..672
<223> OTHER INFORMATION: /mol_type="protein"
    /note="SEQ ID NO:12"
    /organism="Parvovirus"

<400> SEQUENCE: 12

Met Ala Gly Asn Ala Tyr Ser Asp Glu Val Leu Gly Val Thr Asn Trp
1               5                   10                  15

Leu Lys Asp Lys Ser Ser Gln Glu Val Phe Ser Phe Val Phe Lys Asn
            20                  25                  30

Glu Asn Val Gln Leu Asn Gly Lys Asp Ile Gly Trp Asn Ser Tyr Arg
        35                  40                  45

Lys Glu Leu Gln Asp Asp Glu Leu Lys Ser Leu Gln Arg Gly Ala Glu
    50                  55                  60

Thr Thr Trp Asp Gln Ser Glu Asp Met Glu Trp Glu Ser Ala Val Asp
65                  70                  75                  80

Asp Met Thr Lys Lys Gln Val Phe Ile Phe Asp Ser Leu Val Lys Lys
                85                  90                  95

Cys Leu Phe Glu Val Leu Ser Thr Lys Asn Ile Ala Pro Ser Asn Val
            100                 105                 110

Thr Trp Phe Val Gln His Glu Trp Gly Lys Asp Gln Gly Trp His Cys
        115                 120                 125

His Val Leu Ile Gly Gly Lys Asp Phe Ser Gln Pro Gln Gly Lys Trp
    130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Ser Glu Trp Val Thr Leu Leu Thr Tyr Lys His Lys His
            180                 185                 190

Thr Lys Lys Asp Tyr Thr Lys Cys Val Leu Phe Gly Asn Met Ile Ala
        195                 200                 205

Tyr Tyr Phe Leu Ser Lys Lys Ile Cys Thr Ser Pro Pro Arg Asp
    210                 215                 220

Gly Gly Tyr Phe Leu Ser Ser Asp Ser Gly Trp Lys Thr Asn Phe Leu
225                 230                 235                 240

Lys Glu Gly Glu Arg His Leu Val Ser Leu Tyr Thr Asp Glu Met
                245                 250                 255

Lys Pro Glu Thr Val Glu Thr Thr Val Thr Thr Ala Gln Glu Ala Lys
            260                 265                 270

Arg Gly Arg Ile Gln Thr Arg Lys Glu Val Ser Ile Lys Thr Thr Leu
        275                 280                 285
```

Lys Glu Leu Val His Lys Arg Val Thr Ser Pro Asp Trp Met Met
            290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Ala Asn Phe Ser Met Ala Ser Thr Arg Thr Cys Arg Ile Phe Ala
            355                 360                 365

Glu His Gly Trp Asn Tyr Ile Lys Val Cys His Ala Ile Cys Cys Val
        370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
        435                 440                 445

Gly Gln Gln Val Asn Gln Phe Lys Ala Ile Cys Ser Gly Gln Thr Ile
    450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Arg Ile Gly Cys
                485                 490                 495

Glu Glu Arg Pro Glu His Thr Gln Pro Ile Arg Asp Arg Met Leu Asn
            500                 505                 510

Ile His Leu Thr Arg Thr Leu Pro Gly Asp Phe Gly Leu Val Asp Lys
        515                 520                 525

His Glu Trp Pro Leu Ile Cys Ala Trp Leu Val Lys Asn Gly Tyr Gln
    530                 535                 540

Ser Thr Met Ala Cys Tyr Cys Ala Lys Trp Gly Lys Val Pro Asp Trp
545                 550                 555                 560

Ser Glu Asp Trp Ala Glu Pro Lys Leu Asp Thr Pro Ile Asn Ser Leu
                565                 570                 575

Gly Ser Met Arg Ser Pro Ser Leu Thr Pro Arg Ser Thr Pro Leu Ser
            580                 585                 590

Gln Asn Tyr Ala Leu Thr Pro Leu Ala Ser Asp Leu Ala Asp Leu Ala
        595                 600                 605

Leu Glu Pro Trp Ser Thr Pro Asn Thr Pro Val Ala Gly Thr Ala Ala
    610                 615                 620

Ser Gln Asn Thr Gly Glu Ala Gly Ser Thr Ala Cys Gln Gly Ala Gln
625                 630                 635                 640

Arg Ser Pro Thr Trp Ser Glu Ile Glu Ala Asp Leu Arg Ala Cys Phe
                645                 650                 655

Ser Gln Glu Gln Leu Glu Ser Asp Phe Asn Glu Glu Leu Thr Leu Asp
            660                 665                 670

<210> SEQ ID NO 13
<211> LENGTH: 187
<212> TYPE: PRT
<213> ORGANISM: Parvovirus
<220> FEATURE:

```
<221> NAME/KEY: SOURCE
<222> LOCATION: 1..187
<223> OTHER INFORMATION: /mol_type="protein"
      /note="SEQ ID NO:13"
      /organism="Parvovirus"

<400> SEQUENCE: 13

Met Ala Gly Asn Ala Tyr Ser Asp Glu Val Leu Gly Val Thr Asn Trp
1               5                   10                  15

Leu Lys Asp Lys Ser Ser Gln Glu Val Phe Ser Phe Val Phe Lys Asn
                20                  25                  30

Glu Asn Val Gln Leu Asn Gly Lys Asp Ile Gly Trp Asn Ser Tyr Arg
            35                  40                  45

Lys Glu Leu Gln Asp Asp Glu Leu Lys Ser Leu Gln Arg Gly Ala Glu
        50                  55                  60

Thr Thr Trp Asp Gln Ser Glu Asp Met Glu Trp Glu Ser Ala Val Asp
65                  70                  75                  80

Asp Met Thr Lys Lys Phe Asn Ala Leu Thr Ile Ser Asp Ser Glu Lys
                85                  90                  95

Tyr Ala Ser Gln Pro Lys Leu Arg Ser Tyr Ser Thr Cys Ile Gly Pro
            100                 105                 110

Cys Gly Pro Ser Ser Arg Ala Leu Glu His Thr Lys Tyr Ser Cys Cys
        115                 120                 125

Gly His Cys Ser Lys Pro Lys His Trp Gly Trp Phe His Ser Leu
    130                 135                 140

Pro Arg Cys Ser Thr Glu Pro Asn Leu Val Arg Asp Arg Gly Phe
145                 150                 155                 160

Glu Ser Leu Leu Gln Ser Arg Thr Val Gly Glu Arg Leu Gln Arg Gly
                165                 170                 175

Ala Asp Leu Gly Leu Pro Glu Ile Thr Trp Phe
            180                 185

<210> SEQ ID NO 14
<211> LENGTH: 188
<212> TYPE: PRT
<213> ORGANISM: Parvovirus
<220> FEATURE:
<221> NAME/KEY: SOURCE
<222> LOCATION: 1..188
<223> OTHER INFORMATION: /mol_type="protein"
      /note="SEQ ID NO:14"
      /organism="Parvovirus"

<400> SEQUENCE: 14

Met Ala Gly Asn Ala Tyr Ser Asp Glu Val Leu Gly Val Thr Asn Trp
1               5                   10                  15

Leu Lys Asp Lys Ser Ser Gln Glu Val Phe Ser Phe Val Phe Lys Asn
                20                  25                  30

Glu Asn Val Gln Leu Asn Gly Lys Asp Ile Gly Trp Asn Ser Tyr Arg
            35                  40                  45

Lys Glu Leu Gln Asp Asp Glu Leu Lys Ser Leu Gln Arg Gly Ala Glu
        50                  55                  60

Thr Thr Trp Asp Gln Ser Glu Asp Met Glu Trp Glu Ser Ala Val Asp
65                  70                  75                  80

Asp Met Thr Lys Lys Phe Asn Ala Leu Thr Ile Ser Asp Ser Glu Lys
                85                  90                  95

Tyr Ala Ser Gln Pro Lys Leu Arg Ser Tyr Ser Thr Cys Ile Gly Pro
            100                 105                 110
```

```
Cys Gly Pro Ser Ser Arg Ala Leu Glu His Thr Lys Tyr Ser Cys Cys
            115                 120                 125

Gly His Cys Ser Lys Pro Lys His Trp Gly Trp Phe His Ser Leu
    130                 135                 140

Pro Arg Cys Ser Thr Glu Pro Asn Leu Val Arg Asp Arg Gly Phe
145                 150                 155                 160

Glu Ser Leu Leu Gln Ser Arg Thr Val Gly Glu Arg Leu Gln Arg Gly
                165                 170                 175

Ala Asp Leu Gly Leu Arg Tyr Asn Gly Thr Ser Ser
            180                 185

<210> SEQ ID NO 15
<211> LENGTH: 734
<212> TYPE: PRT
<213> ORGANISM: Parvovirus
<220> FEATURE:
<221> NAME/KEY: SOURCE
<222> LOCATION: 1..734
<223> OTHER INFORMATION: /mol_type="protein"
      /note="SEQ ID NO:15"
      /organism="Parvovirus"

<400> SEQUENCE: 15

Met Ala Pro Pro Ala Lys Arg Ala Lys Arg Gly Trp Val Pro Pro Gly
1               5                   10                  15

Tyr Lys Tyr Leu Gly Pro Gly Asn Ser Leu Asp Gln Gly Glu Pro Thr
            20                  25                  30

Asn Pro Ser Asp Ala Ala Ala Lys Glu His Asp Glu Ala Tyr Asp Gln
        35                  40                  45

Tyr Ile Lys Ser Gly Lys Asn Pro Tyr Leu Tyr Phe Ser Pro Ala Asp
    50                  55                  60

Gln Arg Phe Ile Asp Gln Thr Lys Asp Ala Lys Asp Trp Gly Gly Lys
65                  70                  75                  80

Val Gly His Tyr Phe Phe Arg Thr Lys Arg Ala Phe Ala Pro Lys Leu
                85                  90                  95

Ser Thr Asp Ser Glu Pro Gly Thr Ser Gly Val Ser Arg Pro Gly Lys
            100                 105                 110

Arg Thr Lys Pro Pro Ala His Ile Phe Val Asn Gln Ala Arg Ala Lys
        115                 120                 125

Lys Lys Arg Ala Ser Leu Ala Ala Gln Gln Arg Thr Leu Thr Met Ser
    130                 135                 140

Asp Gly Thr Glu Thr Asn Gln Pro Asp Thr Gly Ile Ala Asn Ala Arg
145                 150                 155                 160

Val Glu Arg Ser Ala Asp Gly Gly Ser Gly Gly Gly Ser
                165                 170                 175

Gly Gly Gly Gly Ile Gly Val Ser Thr Gly Thr Tyr Asn Gln Thr
            180                 185                 190

Thr Tyr Lys Phe Leu Gly Asp Gly Trp Val Glu Ile Thr Ala His Ala
        195                 200                 205

Ser Arg Leu Leu His Leu Gly Met Pro Pro Ser Glu Asn Tyr Cys Arg
    210                 215                 220

Val Thr Val His Asn Asn Gln Thr Thr Gly His Gly Thr Lys Val Lys
225                 230                 235                 240

Gly Asn Met Ala Tyr Asp Thr His Gln Gln Ile Trp Thr Pro Trp Ser
                245                 250                 255

Leu Val Asp Ala Asn Ala Trp Gly Val Trp Phe Gln Pro Ser Asp Trp
            260                 265                 270
```

```
Gln Phe Ile Gln Asn Ser Met Glu Ser Leu Asn Leu Asp Ser Leu Ser
            275                 280                 285

Gln Glu Leu Phe Asn Val Val Val Lys Thr Val Thr Glu Gln Gln Gly
        290                 295                 300

Ala Gly Gln Asp Ala Ile Lys Val Tyr Asn Asn Asp Leu Thr Ala Cys
305                 310                 315                 320

Met Met Val Ala Leu Asp Ser Asn Asn Ile Leu Pro Tyr Thr Pro Ala
                325                 330                 335

Ala Gln Thr Ser Glu Thr Leu Gly Phe Tyr Pro Trp Lys Pro Thr Ala
                340                 345                 350

Pro Ala Pro Tyr Arg Tyr Tyr Phe Phe Met Pro Arg Gln Leu Ser Val
                355                 360                 365

Thr Ser Ser Asn Ser Ala Glu Gly Thr Gln Ile Thr Asp Thr Ile Gly
        370                 375                 380

Glu Pro Gln Ala Leu Asn Ser Gln Phe Phe Thr Ile Glu Asn Thr Leu
385                 390                 395                 400

Pro Ile Thr Leu Leu Arg Thr Gly Asp Glu Phe Thr Gly Thr Tyr
                405                 410                 415

Ile Phe Asn Thr Asp Pro Leu Lys Leu Thr His Thr Trp Gln Thr Asn
                420                 425                 430

Arg His Leu Ala Cys Leu Gln Gly Ile Thr Asp Leu Pro Thr Ser Asp
            435                 440                 445

Thr Ala Thr Ala Ser Leu Thr Ala Asn Gly Asp Arg Phe Gly Ser Thr
        450                 455                 460

Gln Thr Gln Asn Val Asn Tyr Val Thr Glu Ala Leu Arg Thr Arg Pro
465                 470                 475                 480

Ala Gln Ile Gly Phe Met Gln Pro His Asp Asn Phe Glu Ala Asn Arg
                485                 490                 495

Gly Gly Pro Phe Lys Val Pro Val Val Pro Leu Asp Ile Thr Ala Gly
            500                 505                 510

Glu Asp His Asp Ala Asn Gly Ala Ile Arg Phe Asn Tyr Gly Lys Gln
        515                 520                 525

His Gly Glu Asp Trp Ala Lys Gln Gly Ala Ala Pro Glu Arg Tyr Thr
        530                 535                 540

Trp Asp Ala Ile Asp Ser Ala Ala Gly Arg Asp Thr Ala Arg Cys Phe
545                 550                 555                 560

Val Gln Ser Ala Pro Ile Ser Ile Pro Pro Asn Gln Asn Gln Ile Leu
                565                 570                 575

Gln Arg Glu Asp Ala Ile Ala Gly Arg Thr Asn Met His Tyr Thr Asn
                580                 585                 590

Val Phe Asn Ser Tyr Gly Pro Leu Ser Ala Phe Pro His Pro Asp Pro
            595                 600                 605

Ile Tyr Pro Asn Gly Gln Ile Trp Asp Lys Glu Leu Asp Leu Glu His
        610                 615                 620

Lys Pro Arg Leu His Val Thr Ala Pro Phe Val Cys Lys Asn Asn Pro
625                 630                 635                 640

Pro Gly Gln Leu Phe Val His Leu Gly Pro Asn Leu Thr Asp Gln Phe
                645                 650                 655

Asp Pro Asn Ser Thr Thr Val Ser Arg Ile Val Thr Tyr Ser Thr Phe
                660                 665                 670

Tyr Trp Lys Gly Ile Leu Lys Phe Lys Ala Lys Leu Arg Pro Asn Leu
            675                 680                 685
```

```
Thr Trp Asn Pro Val Tyr Gln Ala Thr Thr Asp Ser Val Ala Asn Ser
    690             695                 700

Tyr Met Asn Val Lys Lys Trp Leu Pro Ser Ala Thr Gly Asn Met His
705             710                 715                 720

Ser Asp Pro Leu Ile Cys Arg Pro Val Pro His Met Thr Tyr
                725                 730

<210> SEQ ID NO 16
<211> LENGTH: 592
<212> TYPE: PRT
<213> ORGANISM: Parvovirus
<220> FEATURE:
<221> NAME/KEY: SOURCE
<222> LOCATION: 1..592
<223> OTHER INFORMATION: /mol_type="protein"
      /note="SEQ ID NO:16"
      /organism="Parvovirus"

<400> SEQUENCE: 16

Met Ser Asp Gly Thr Glu Thr Asn Gln Pro Asp Thr Gly Ile Ala Asn
1               5                   10                  15

Ala Arg Val Glu Arg Ser Ala Asp Gly Gly Ser Gly Gly Gly
            20                  25                  30

Gly Ser Gly Gly Gly Ile Gly Val Ser Thr Gly Thr Tyr Asp Asn
        35                  40                  45

Gln Thr Thr Tyr Lys Phe Leu Gly Asp Gly Trp Val Glu Ile Thr Ala
    50                  55                  60

His Ala Ser Arg Leu Leu His Leu Gly Met Pro Pro Ser Glu Asn Tyr
65              70                  75                  80

Cys Arg Val Thr Val His Asn Asn Gln Thr Thr Gly His Gly Thr Lys
                85                  90                  95

Val Lys Gly Asn Met Ala Tyr Asp Thr His Gln Gln Ile Trp Thr Pro
            100                 105                 110

Trp Ser Leu Val Asp Ala Asn Ala Trp Gly Val Trp Phe Gln Pro Ser
        115                 120                 125

Asp Trp Gln Phe Ile Gln Asn Ser Met Glu Ser Leu Asn Leu Asp Ser
    130                 135                 140

Leu Ser Gln Glu Leu Phe Asn Val Val Lys Thr Val Thr Glu Gln
145                 150                 155                 160

Gln Gly Ala Gly Gln Asp Ala Ile Lys Val Tyr Asn Asn Asp Leu Thr
                165                 170                 175

Ala Cys Met Met Val Ala Leu Asp Ser Asn Asn Ile Leu Pro Tyr Thr
            180                 185                 190

Pro Ala Ala Gln Thr Ser Glu Thr Leu Gly Phe Tyr Pro Trp Lys Pro
        195                 200                 205

Thr Ala Pro Ala Pro Tyr Arg Tyr Tyr Phe Met Pro Arg Gln Leu
    210                 215                 220

Ser Val Thr Ser Ser Asn Ser Ala Glu Gly Thr Gln Ile Thr Asp Thr
225                 230                 235                 240

Ile Gly Glu Pro Gln Ala Leu Asn Ser Gln Phe Phe Thr Ile Glu Asn
                245                 250                 255

Thr Leu Pro Ile Thr Leu Leu Arg Thr Gly Asp Glu Phe Thr Thr Gly
            260                 265                 270
```

```
Thr Tyr Ile Phe Asn Thr Asp Pro Leu Lys Leu Thr His Thr Trp Gln
        275                 280                 285

Thr Asn Arg His Leu Ala Cys Leu Gln Gly Ile Thr Asp Leu Pro Thr
    290                 295                 300

Ser Asp Thr Ala Thr Ala Ser Leu Thr Ala Asn Gly Asp Arg Phe Gly
305                 310                 315                 320

Ser Thr Gln Thr Gln Asn Val Asn Tyr Val Thr Glu Ala Leu Arg Thr
                325                 330                 335

Arg Pro Ala Gln Ile Gly Phe Met Gln Pro His Asp Asn Phe Glu Ala
            340                 345                 350

Asn Arg Gly Gly Pro Phe Lys Val Pro Val Val Pro Leu Asp Ile Thr
            355                 360                 365

Ala Gly Glu Asp His Asp Ala Asn Gly Ala Ile Arg Phe Asn Tyr Gly
        370                 375                 380

Lys Gln His Gly Glu Asp Trp Ala Lys Gln Gly Ala Ala Pro Glu Arg
385                 390                 395                 400

Tyr Thr Trp Asp Ala Ile Asp Ser Ala Ala Gly Arg Asp Thr Ala Arg
                405                 410                 415

Cys Phe Val Gln Ser Ala Pro Ile Ser Ile Pro Pro Asn Gln Asn Gln
            420                 425                 430

Ile Leu Gln Arg Glu Asp Ala Ile Ala Gly Arg Thr Asn Met His Tyr
        435                 440                 445

Thr Asn Val Phe Asn Ser Tyr Gly Pro Leu Ser Ala Phe Pro His Pro
        450                 455                 460

Asp Pro Ile Tyr Pro Asn Gly Gln Ile Trp Asp Lys Glu Leu Asp Leu
465                 470                 475                 480

Glu His Lys Pro Arg Leu His Val Thr Ala Pro Phe Val Cys Lys Asn
                485                 490                 495

Asn Pro Pro Gly Gln Leu Phe Val His Leu Gly Pro Asn Leu Thr Asp
            500                 505                 510

Gln Phe Asp Pro Asn Ser Thr Thr Val Ser Arg Ile Val Thr Tyr Ser
        515                 520                 525

Thr Phe Tyr Trp Lys Gly Ile Leu Lys Phe Lys Ala Lys Leu Arg Pro
        530                 535                 540

Asn Leu Thr Trp Asn Pro Val Tyr Gln Ala Thr Thr Asp Ser Val Ala
545                 550                 555                 560

Asn Ser Tyr Met Asn Val Lys Lys Trp Leu Pro Ser Ala Thr Gly Asn
                565                 570                 575

Met His Ser Asp Pro Leu Ile Cys Arg Pro Val Pro His Met Thr Tyr
            580                 585                 590
```

US 8,916,176 B2

MODIFIED PARVOVIRUS HAVING ENHANCED ANTI-TUMOR EFFICACY

This application is a continuation of PCT/EP2011/003021, filed Jun. 17, 2011; which claims the priority of EP Application No. 10166332, filed Jun. 17, 2010. The contents of the above-identified applications are incorporated herein by reference in their entirety.

REFERENCE TO SEQUENCE LISTING, TABLE OR COMPUTER PROGRAM

The Sequence Listing is concurrently submitted herewith the specification as an ASCII formatted text file via EFS-Web with a file name of Sequence Listing.txt with a creation date of Dec. 12, 2012, and a size of 3 kilobytes. The Sequence Listing filed via EFS-Web is part of the specification and is hereby incorporated in its entirety by reference herein.

TECHNICAL FIELD

The present invention relates to a parvovirus variant showing higher anti-tumor potential compared to the wild type parvovirus, wherein said variant is characterized by (a) an amino acid substitution, deletion or addition, preferably substitution, at position Lys96 of NS2 and/or position Leu103 of NS2 (the latter one also inducing an amino acid substitution at position Tyr595 of NS1), or (b) an in-frame deletion in the left-hand part of the H-1PV genome, preferably a deletion resulting in the translation of NS1 and NS2 proteins having a deletion of 38 amino acids in their C-terminal and central part, respectively. The present invention also relates to the use of said parvovirus variant for cancer therapy.

BACKGROUND OF THE INVENTION

Oncolytic viruses such as rodent parvoviruses represent novel tools for cancer treatment [1, 2]. Besides specifically killing cancer cells (oncolysis), these agents also provide danger signals prompting the immune system to eliminate virus-infected tumors [3]. As a consequence of oncolytic events, the innate and adaptive immune systems gain access to tumor antigens, which may result in cross-priming and vaccination effects [4, 5]. Rodent parvoviruses are single-stranded DNA viruses possessing "intrinsic" oncolytic activity, i.e. they preferentially replicate in and kill cancer cells of both murine and human origin [6, 7]. Yet the anticancer efficacy of the most promising candidates for human clinical applications (including H-1PV) needs to be improved. So far, for improvement the following strategies were applied:

(a) Creation of PV-based vectors by introducing therapeutic genes (e.g., chemokines or cytokines)[8, 9, 10];

(b) Use of natural rodent PVs in combination with chemotherapeutic drugs (e.g., gemcitabine)[11]; and (c) Creation of PV mutants bearing point mutations at potential phosphorylation sites of the large non-structural protein NS1 [12].

However, the results obtained need further improvement, in particular as regards higher anti-tumor potential compared to natural PVs currently used, and reduction of time during the production step.

SUMMARY OF THE INVENTION

It is the object of the present invention to provide improved parvoviruses for therapeutic uses.

According to the invention this is achieved by the subject matters defined in the claims. The present invention is based on the applicant's isolation of an H-1PV mutant that supplants the standard wild type H-1PV in co-infected cell cultures [13]. The present invention is also based on the critical role played by small non-structural proteins of rodent PV and their interaction with specific cellular partners for virus fitness [14, 15] and the possibility to improve the fitness of mouse parvovirus by slight modifications within these viral proteins [16].

The inventors started from the assumption that improving activities of the small non-structural proteins of rodent PVs may also account for a higher efficacy of these viruses in virus production and their anti-tumor potential. These assumptions were confirmed by introducing these mutations into the H-1PV genome and testing with regard to (a) the amount of progeny virions retrieved from productive cells, and (b) their onco-toxic/lytic activity against human tumor models. The data obtained with these improved H-1PVs demonstrated indeed a higher burst of progeny virions and an increased ratio of infectious versus full particles in the viral stock, a faster propagation in cell cultures and a better anticancer activity against tumor xenografts.

In summary, the improved PVs of the present invention (a) exhibit a higher anti-tumor potential compared with natural PVs currently used in preclinical assays as well as lead (b) to a reduction of time during the production step, and (c) the use of lower doses of full virions during (pre)clinical assays. Accordingly, the viruses of the present invention do not require the presence of a therapeutic gene and the combination with chemotherapeutic drugs for efficient therapy.

The viral genome is represented as a grey box. Viral promoters P4 and P38 are shown as black arrows. "NS1/NS2" and "VP1/2" that are mentioned above the grey box indicate the genome regions encoding the non-structural NS1/NS2 and capsid VP1/VP2 proteins, respectively. The pUC19 expression vector is represented as a black lane. Sites of point mutations (A-D) are indicated as grey bars, deletion (E) is indicated as a grey triangle. Nucleotide (nt) modifications (A-D) or deletion (E) are indicated in italics below the genome. Grey arrows below the genome show the resulting viral proteins together with the resulting amino acid (aa) modifications (A-D) or deletion (E) indicated in grey when appropriate. Leu, Pro, Tyr, His, Lys, Glu, Met: amino acids leucine, proline, tyrosine, histidine, lysine, glutamic acid and methionine, respectively.

FIG. 2 shows increased infectivity of Del H-1PV compared to wild type H-1PV and similar or even better infectivity of PMut1 H-1PV and PMut2 H-1PV variants compared with Del H-1PV.

Viruses were produced by infection of NB-324K cells and analysed by Plaque Assay (giving the number of PFU=plaque forming units), Hybridisation Assay (giving the number of RU=replication units) and Dot Blot (giving the number of full viral particles).

Numbers in grey indicate P/I values that are lower than the value obtained with wild type (wt) H-1PV.

Grey and patterned boxes with an arrow indicate the decreasing (/) or increasing (x) factor between the P/I ratio of wild type H-1PV and the one of the corresponding H-1PV deletion or point mutant variant.

Figure 3:
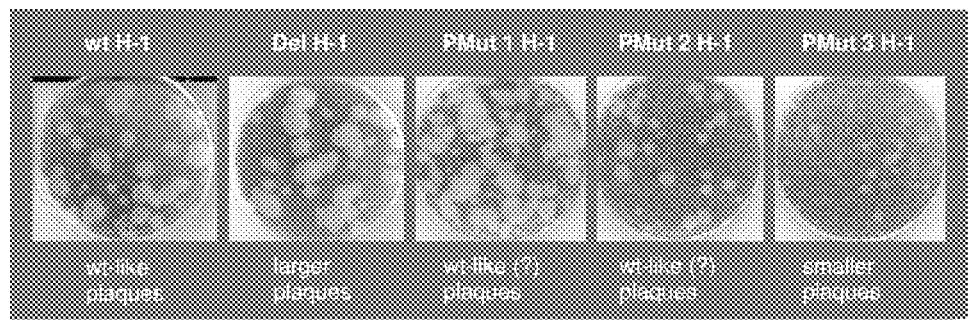
Figure 3:
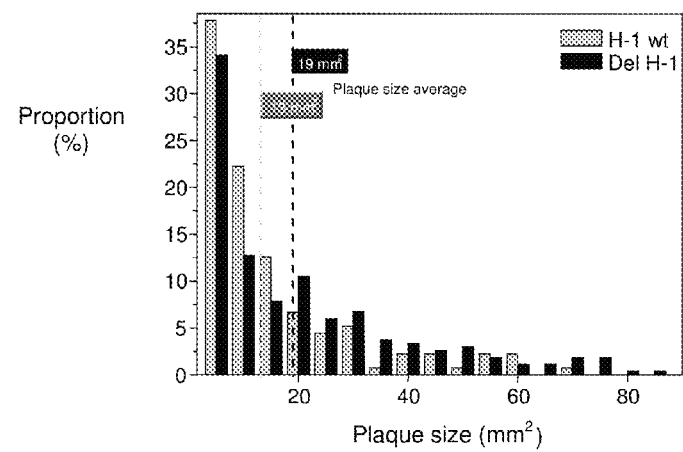

FIG. 3 shows increased propagation of Del H-1PV compared with wild type H-1PV in infected NB-324K cells.

(A) Newly-made wt H-1PV, Del H-1PV, PMut1 H-1PV, PMut2 H-1PV, and PMut3 H-1PV virus stocks were analysed by Plaque Assay using NB-324K cells. One example of plaques obtained with each virus stock is shown to illustrate the size of the plaques.

(B) The proportion of plaques showing a given size with wild type H-1PV (grey boxes) or Del H-1PV (black boxes) virus stock is given as a percentage of the total amount of plaques examined (n>100 plaques) for each case. The average size of plaques obtained with the wild-type H-1PV or Del H-1PV virus stock is indicated in a grey or black box and depicted by a grey or black dotted line, respectively.

Figure 4:
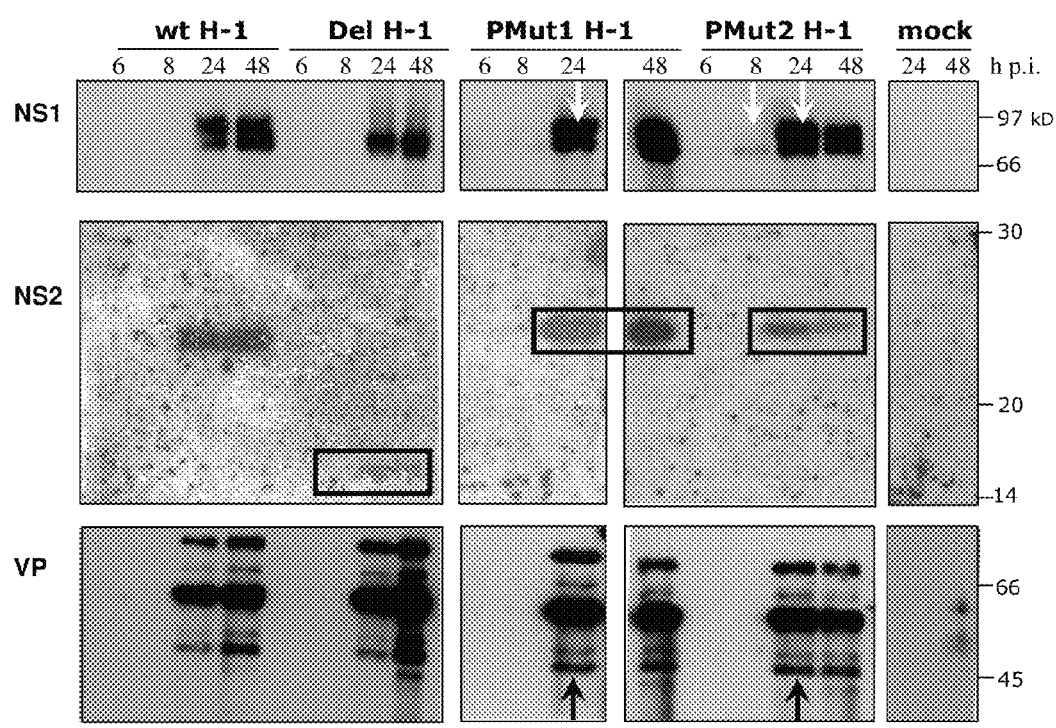

FIG. 4 shows viral protein accumulation in infected NB-324K cells.

$1.5 \times 10^5$ NB-324K cells were infected with wt H-1PV, Del H-1PV, PMut1 H-1PV or PMut2 H-1PV at a multiplicity of infection (moi) of 3 pfu/cell. Whole cell lysates were performed at the indicated hours (h) post infection (p.i.) and 10 µg of total protein extracts were migrated onto a 12% SDS-polyacrylamide gel and subsequently analysed by immunoblotting. The non-structural proteins NS1 and NS2 and the viral capsid proteins VP were detected with the polyclonal rabbit antibodies SP8, anti-NS2P, and anti-VPpep, respectively. White and black arrows indicate an increased and/or earlier accumulation of PMut variant NS1 and VP proteins, respectively, compared to the one observed in wild type H-1PV-infected cell extracts at 8 h or 24 h p.i. Variation in the accumulation of Del or PMut variant NS2 proteins compared to wild type NS2 proteins are highlighted by black boxes. Protein marker sizes are shown on the right side. mock: non infected, medium-treated cells, kD: kiloDalton.

Figure 5:
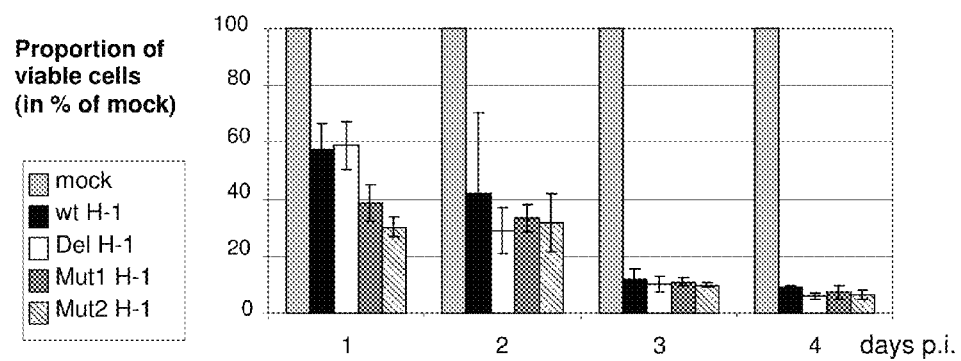
Figure 5:
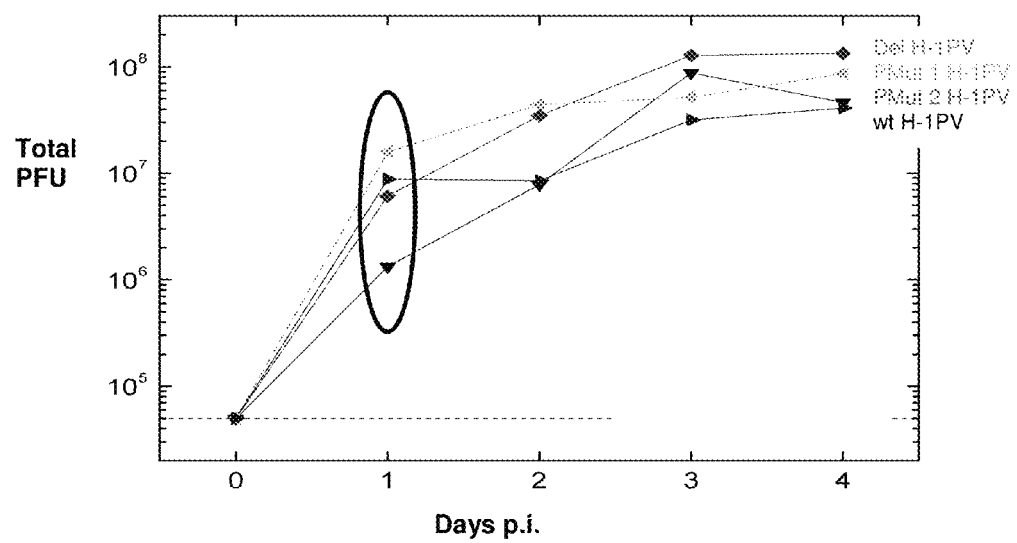

FIG. 5 shows increased growth inhibition and virus production of PMut1 H-1PV and PMut2 H-1PV variants at early points of time post-infection in human NB-324K cells.

(A) NB-324K cells were infected with wild type (wt) H-1PV, Del H-1PV, PMut1 H-1PV or PMut2 H-1PV at a moi of 3 pfu/cell. The amount of living cells was determined at the indicated days post infection (p.i.) using a CASY cell counter system. The proportion of living cells in infected samples is expressed as a percentage of the amount of living cells in the mock-treated sample. Light grey bars: mock (uninfected, medium-treated), black bar: wild type, white bar: Del H-1PV, dark grey bar: PMut1 H-1PV, dashed grey bar: PMut2 H-1PV.

(B) $1.5 \times 10^5$ NB-324K cells were infected with wt H-1PV, Del H-1PV, PMut1 H-1PV or PMut2 H-1PV at a moi of 0.5 pfu/cell. Virus was recovered at the indicated days post infection (p.i.) and the total amount of plaque forming units (PFU) was determined by plaque assay. Data obtained with wt H-1PV, Del H-1PV, PMut1 H-1PV and PMut2 H-1PV are represented by black or grey lanes, as indicated in the graph.

Figure 6:
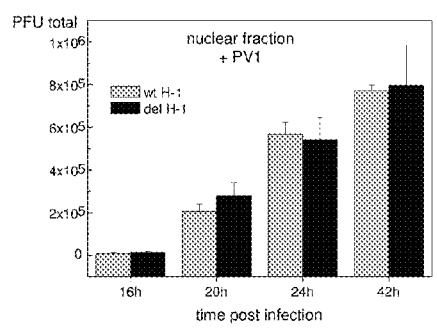
Figure 6:
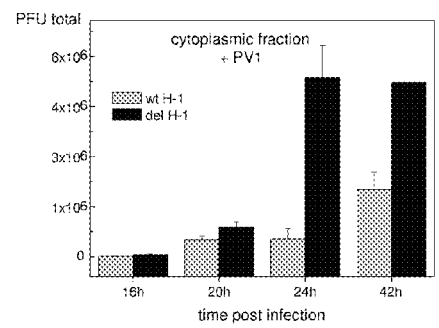
Figure 6:
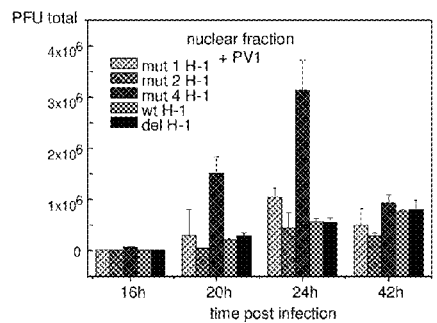
Figure 6:
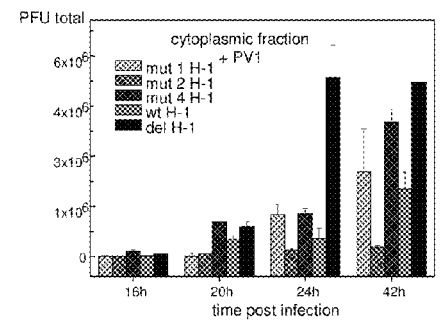

FIG. 6 shows Pfu-distribution in the nucleus and cytoplasm of infected NB-324K cells.

$5 \times 10^5$ NB-324K cells were infected with wild type H-1PV (upper and lower panels), Del H-1PV (upper and lower panels), PMut1 H-1PV (lower panels), PMut2 H-1PV (lower panels) or PMut4 H-1PV (lower panels) at a moi of 1 pfu/cell. Neutralizing polyclonal rabbit antibody PV1 was added into the medium of infected cells 2 hours post infection (p.i.) in order to block secondary infections. Isolation of the nuclear and cytoplasmic fractions of infected cells was carried out at the indicated hours (h) post infection (p.i). The total amount of plaque-forming unit (PFU) in each nuclear (A, C) and cytoplasmic (B, D) fractions was determined by plaque assay.

Figure 7:
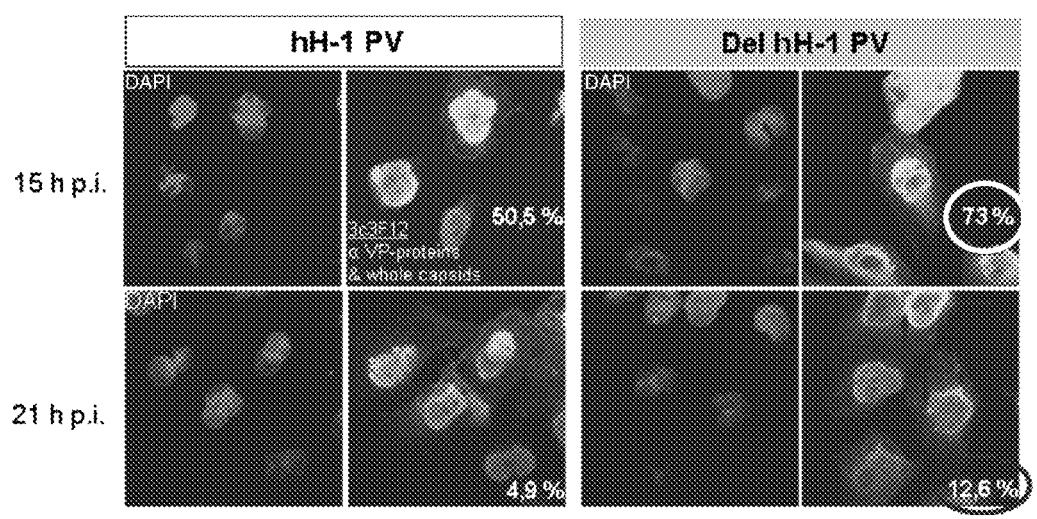

FIG. 7 shows that some steps of the Del H-1PV life cycle are faster than that of wt H-1PV.

NB-324K cells were infected with the hybrid hH-1PV or hybrid Del hH-1PV at a moi of 3 pfu/cell. Cells were fixed at the indicated hours (h) post infection (p.i.) and free or assembled capsid proteins were detected by immunofluorescent staining using 3c3F12 as primary antibody. Numbers in white (with a white circle for Del hH-1PV) represent the percentage of positive cells showing a predominant nuclear staining. White arrows indicate outcoming virions from infected cells. 3c3F12: mouse monoclonal antibody recognizing both viral capsid VP proteins and whole capsids. DAPI: 4',6-diamidino-2-phenylindole; a fluorescent stain that binds to DNA.

Figure 8:
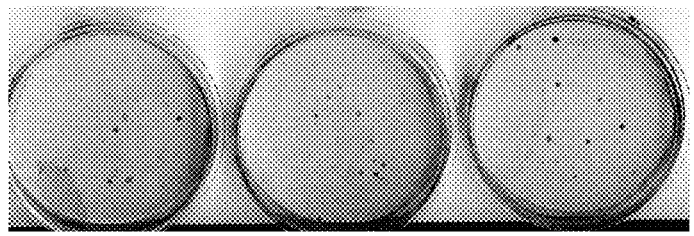
Figure 8:
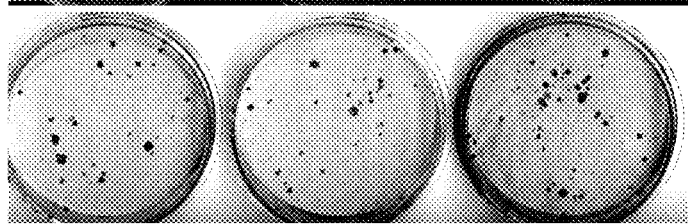
Figure 8:
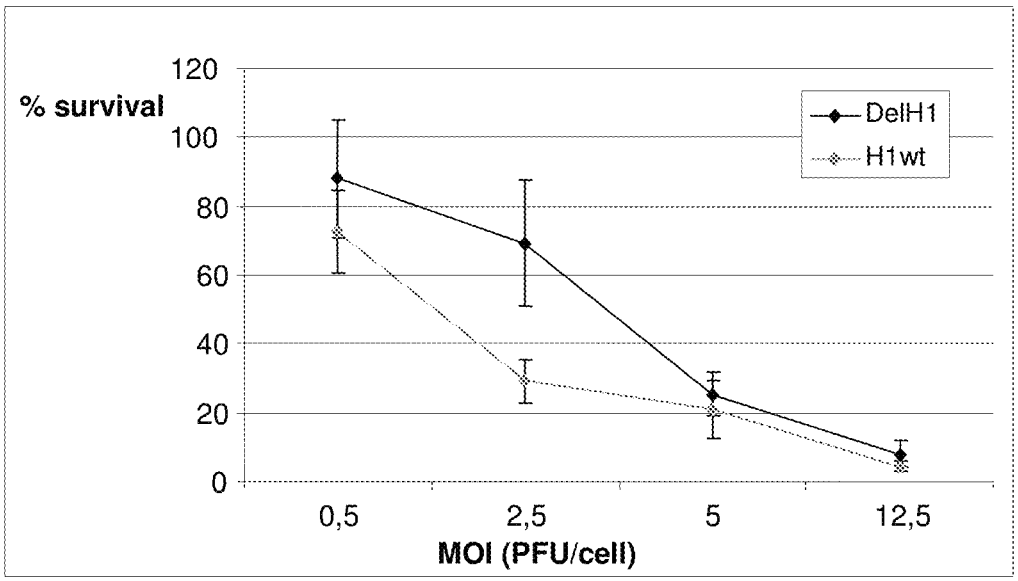

FIG. 8 shows that Del H-1PV had lower cytotoxicity than wt H-1PV.

NB-324K cells were infected with wild type (wt) H-1PV or Del H-1PV at various moi (see B). Infected cells were recovered 4 hours post infection and seeded at a low density on fresh cell culture dishes.

(A) The growth of cell colonies was followed over several days post-reseeding and cells were fixed and stained with a crystal violet solution when colonies were easily detected by light microscopy.

(B) The percentage of surviving cells upon infection with wild type (wt) H-1PV or Del H-1PV are represented with a grey or black lane, respectively.

Figure 9:
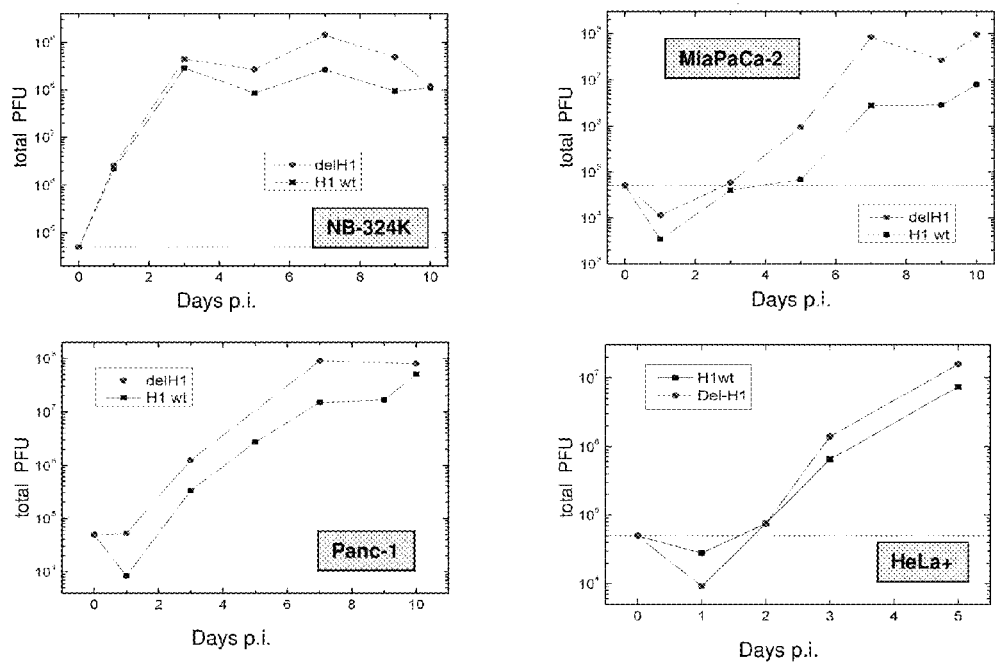

FIG. 9 shows increased virus production of Del H-1PV in different pancreatic cancer cell lines and HeLa cells.

$1 \times 10^5$ NB-324K, MiaPaCa-2, Panc-1 or HeLa+ cells were infected with Del H-1PV or wild type (wt) H-1 PV at a moi of 0.5 pfu/cell. Virus was recovered at the indicated days post infection (p.i.) and the total amount of plaque forming units (PFU) was determined by plaque assay. Amounts of infectious particles produced by Del H-1PV and wt H-1PV are represented with a lane and black dots or black rectangles, respectively.

Figure 10:
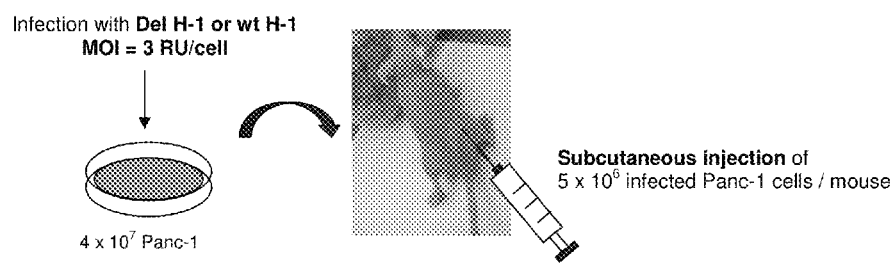
Figure 10:
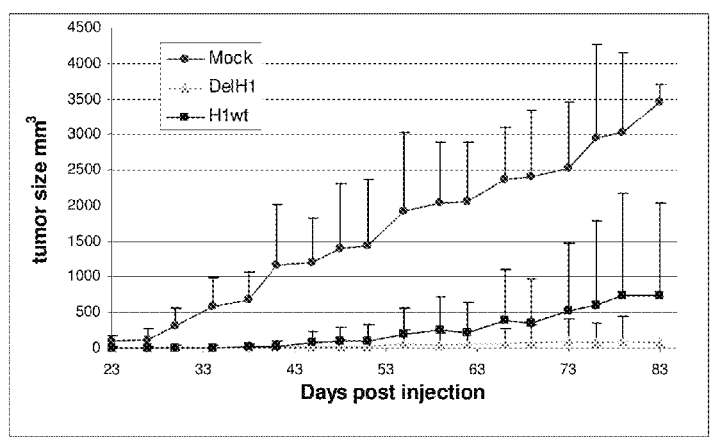
Figure 10:
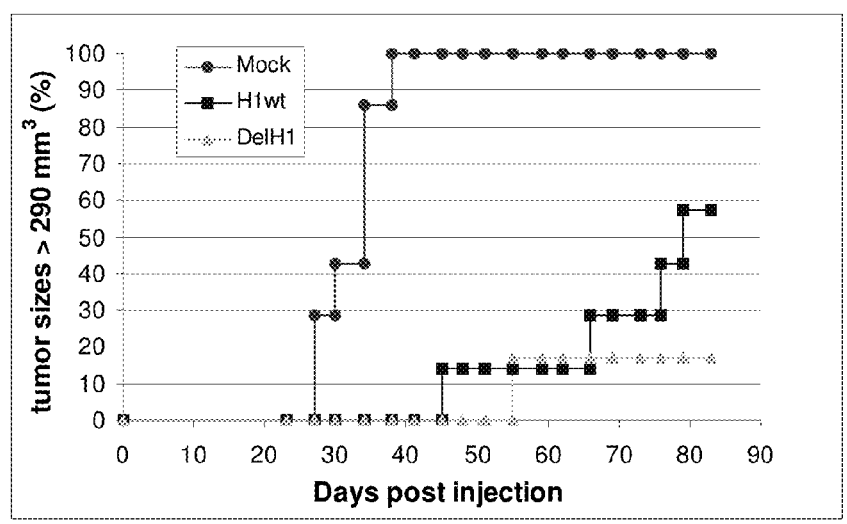

FIG. 10 shows that Del H-1PV is more efficient in suppressing tumor growth.

(A) $4 \times 10^7$ Panc-1 cells were infected with wild type (wt) H-1PV or Del H-1PV at a moi of 3 RU/cell (RU=replication units). Cells were harvested 4 hours post infection and $5 \times 10^6$ cells were subcutaneously injected in Balb/c nude mice.

(B) Tumor sizes were measured over a period of 83 days post cell implantation and presented in $mm^3$. Tumor sizes in animals that received mock-treated (i.e., uninfected), wild type H-1PV-infected or Del H-1PV-infected Panc-1 cells are shown as dark grey lane and small rectangles, a black lane and large rectangles, or a light grey lane and triangles, respectively.

(C) Measurements are presented as percentage of tumor sizes bigger than 290 $mm^3$. Tumor sizes in animals that received mock-treated (i.e., uninfected), wild type H-1PV-infected or Del H-1PV-infected Panc-1 cells are shown as a dark grey lane and small rectangles, a black lane and large rectangles, or a light grey lane and triangles, respectively.

Figure 1:
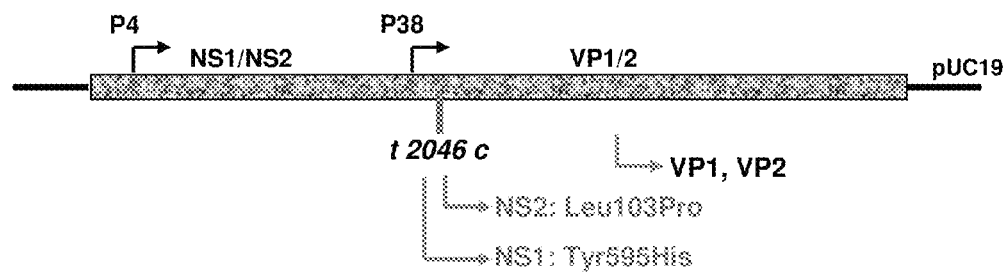
FIG. 1 shows the schematic representation of (A) pPMut1H-1PV, (B) pPMut2H-1PV, (C) pPMut3H-1PV, (D) pPMut4H-1PV and (E) pDel1H-1PV infectious molecular clones.
Figure 1:
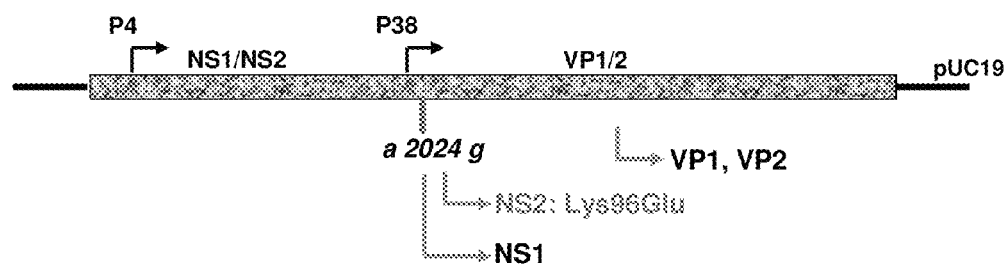
Figure 1:
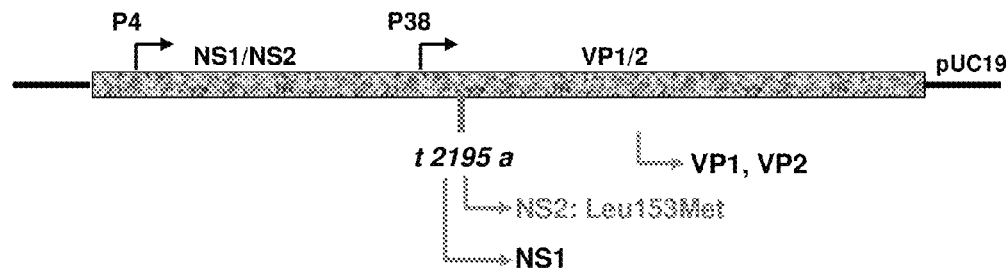
Figure 1:
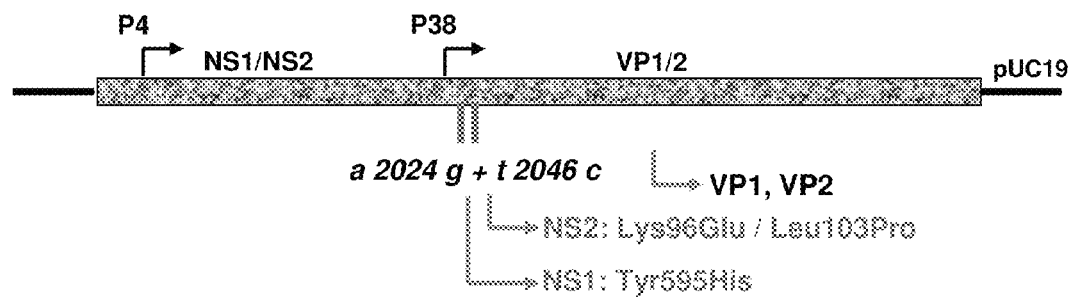
Figure 1:
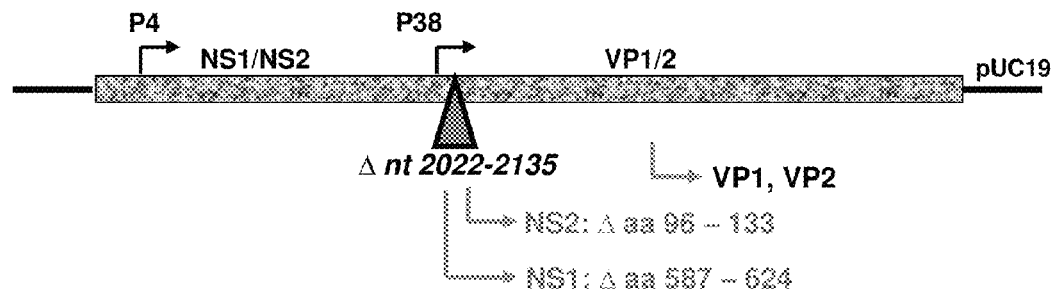

FIGS. 11-1 to 11-9 show H-1PV complete genome sequence (SEQ ID NO: 11) (in nucleotides) and H-1PV NS1 (SEQ ID NO: 12), NS2P (SEQ ID NO: 13), NS2Y (SEQ ID NO: 14), VP1 (SEQ ID NO: 15), and VP2 (SEQ ID NO: 16) protein sequences (in amino acids).

H-1PV genome sequence was retrieved from Gene Databank-accession number X01457.1:

gi|60993|emb|X01457.1| Parvovirus h-1, complete genome

Rhode S. L. III., Paradiso P. R. "Parvovirus genome: nucleotide sequence of h-1 and mapping of its genes by hybrid-arrested translation". J. Virol. 45:173-184 (1983).

and includes corrections of sequence mistakes found in the NS coding regions and further published:

Faisst S, Faisst S R, Dupressoir T, Plaza S, Pujol A, Jauniaux J C, Rhode S L, Rommelaere J. "Isolation of a fully infectious variant of parvovirus H-1 supplanting the standard strain in human cells". J. Virol., 1995, 69: 4538-4543.

nt a305c NS1 aa T14: silent & NS2 aa T14: silent
nt c634a NS1 aa P124Q
nt g1101a NS1 aa E280K These corrections are underlined in the H-1PV nucleotide and amino acid sequences. None of these corrections affects the amino acids and position of the amino acids in the NS1 and NS2 protein sequences as described in the document.

Figure 12:
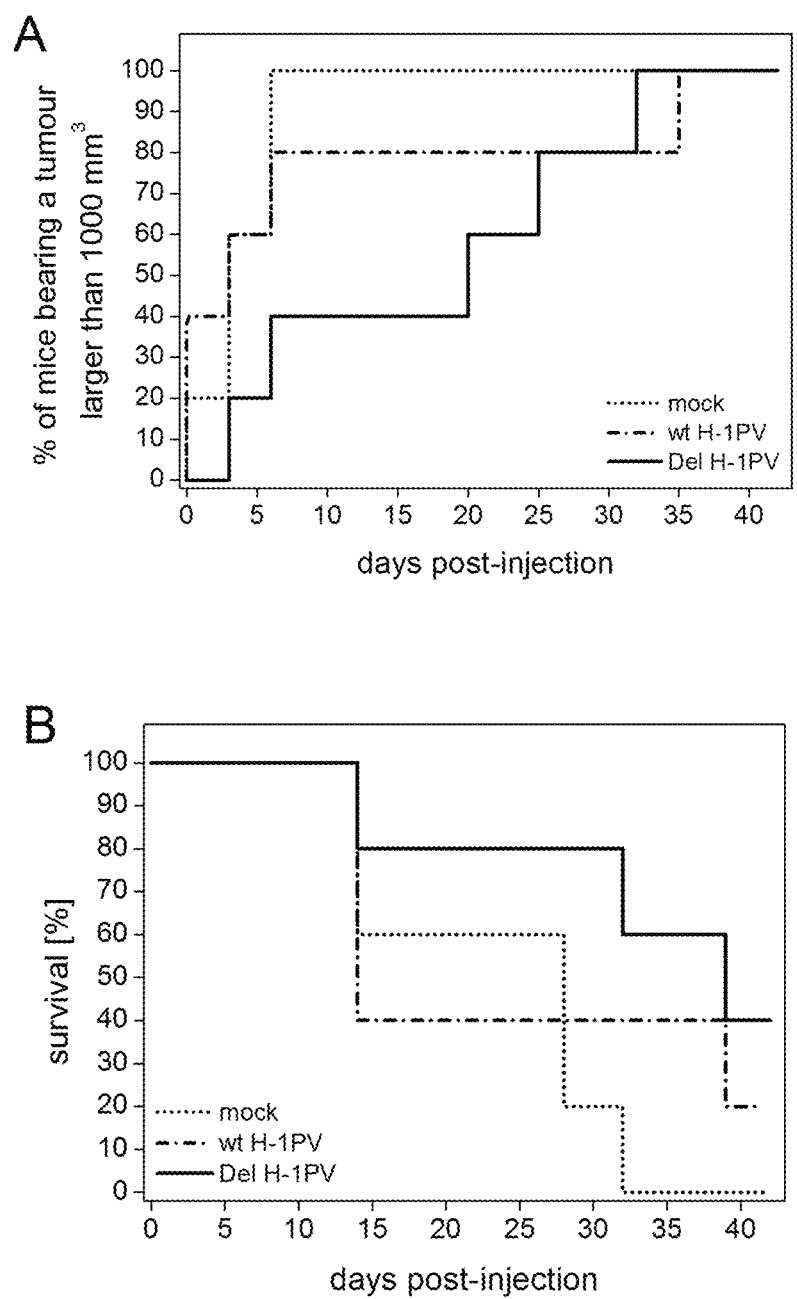

FIG. 12 shows that intratumoral injection of Del H-1PV is more efficient in suppressing growth of HeLa cell-derived tumors compared to wild type H-1PV.

$2 \times 10^6$ HeLa cells were injected subcutaneously into the right flank of Balb/c nude mice. 9 days post-implantation, $10^8$ PFU of Del H-1PV or wild type H-1PV were injected intratumorally. Tumor sizes were monitored up to 42 days post-injection.

(A) Percentage of mice in each group bearing a tumor bigger than 1000 mm$^3$.

(B) Percentage of mice bearing tumors smaller than 3000 mm$^3$ which prevented them from being sacrificed.

Figure 13:
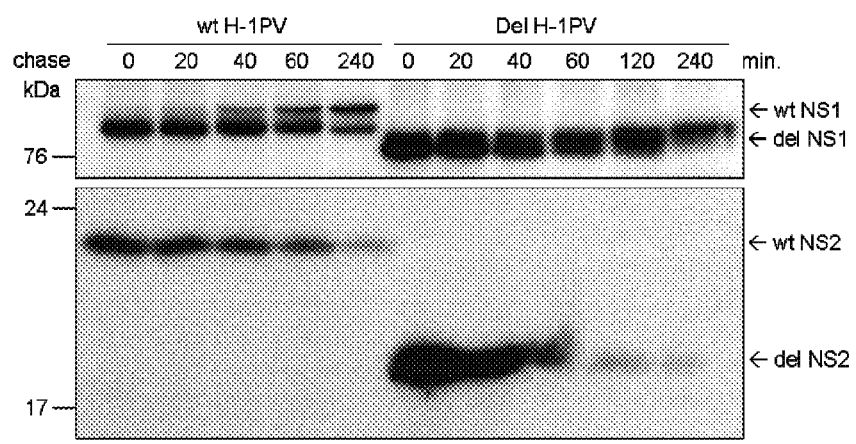

FIG. 13 shows increased neo-synthesis and lability of Del NS2P compared to wild type NS2P proteins.

$8 \times 10^8$ NB-324K cells were infected with wild type (wt) or Del H-1PV at a moi of 10 PFU/cell, first incubated for 18 hours in cold (i.e., non-radioactive) complete medium, and further incubated for a 30-min pulse in presence of Tran$^{35}$S-labeling medium (i.e., containing $^{35}$S-labeled Cysteine and Methionine amino acids). Cells were harvested either immediately (chase point 0 min) or after an additional 20-, 40-, 60-, or 240-min chase period in unlabeled medium. Proteins were extracted in RIPA buffer and $^{35}$S-Cys/Met-labeled NS1 or NS2 proteins, immunoprecipitated with the polyclonal rabbit antibodies SP8 and anti-NS2P, respectively, and separated by electrophoresis on a SDS-12% polyacrylamide gel, were visualized by autoradiography.

Figure 14:
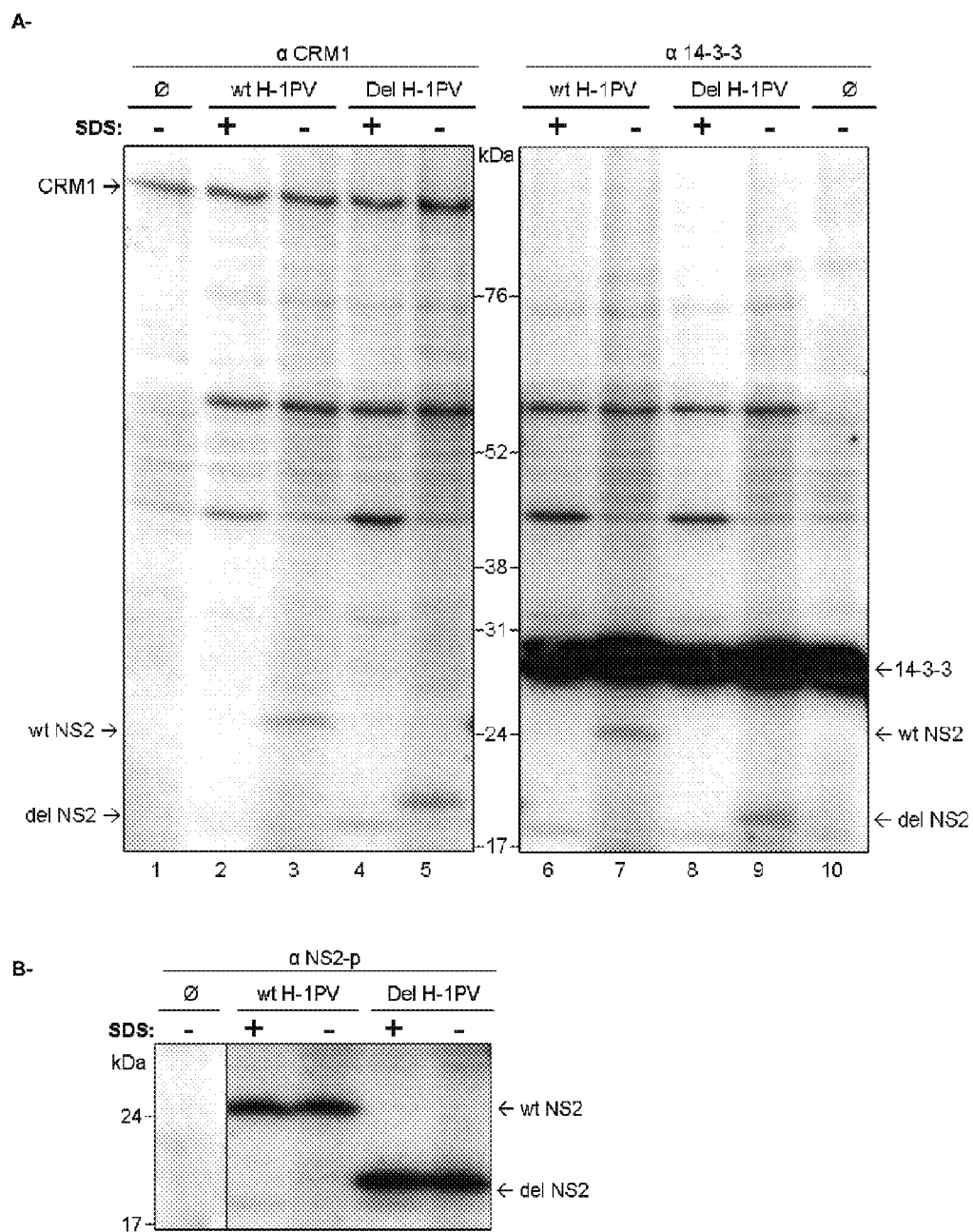

FIG. 14 shows that Del NS2P is still able to interact with the nuclear export factor Crm1 and with members of the 14-3-3 protein family (A) Lysates of NB-324K cells, previously mock-treated (Ø), or infected with either wt H-1PV or Del H-1PV (MOI=10 PFU/cell) for hours and metabolically labelled with Tran$^{35}$S-Cys/Met for 2 hours, were prepared in the presence (+) or absence (-) of SDS and immunoprecipitated with an antiserum against CRM1 (left panel) or against 14-3-3 (right panel). The autoradiograms show immunoprecipitated material after separation by SDS-12% polyacrylamide gel electrophoresis. Positions of wild type (wt) NS2 (25 kDa), Del NS2 (~18 kDa), CRM1 (123 kDa), and 14-3-3 (30 kDa) are indicated on the left and/or right sides of the figure. α: anti; kDa: molecular sizes in kilodaltons.

(B) Lysates of NB-324K cells, previously mock-treated (Ø), or infected with either wt H-1PV or Del H-1PV (MOI=10 PFU/cell) for 18 hours and metabolically labelled with Tran$^{35}$S-Cys/Met for 2 hours, were prepared in the presence (+) or absence (-) of SDS and immunoprecipitated with a polyclonal rabbit antiserum directed against NS2P. The autoradiogram shows immunoprecipitated material after separation by SDS-12% polyacrylamide gel electrophoresis. Positions of wild type (wt) NS2 (25 kDa) and Del NS2 (~18 kDa) are indicated on the right side of the figure. α: anti; kDa: molecular sizes in kilodaltons.

Figure 15:
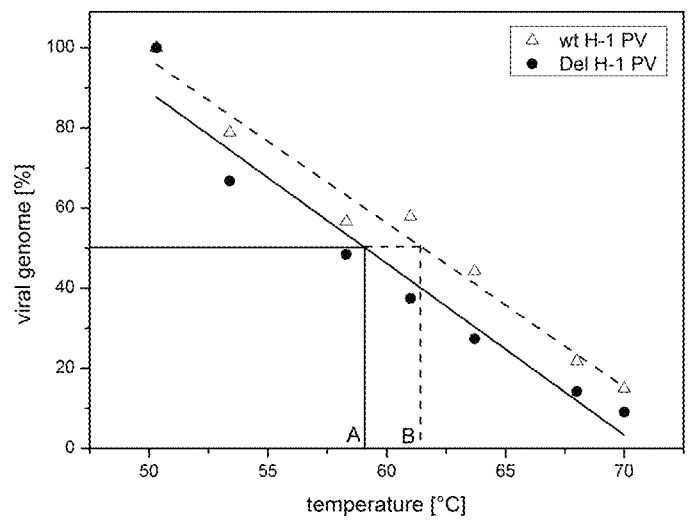

FIG. 15 shows that Del H-1PV virions are more susceptible to heat denaturation than wild type H-1PV virions.

Purified full viral particles were exposed to various, indicated temperatures (generated in a PCR machine) for 10 minutes and the amount of viral genomes that became accessible following this treatment was titrated by quantitative real-time PCR after DNase treatment and alkaline lysis. Point A (i.e., 59.11° C.) and point B (i.e., 61.53° C.) indicate the temperatures at which 50% of Del H-1PV virions (compact line) and of wild type H-1PV virions (dashed line) were destroyed, respectively. This results in a temperature difference of 2.42° C. Data shown in this figure represent the mean of two independent experiments.

Figure 16:
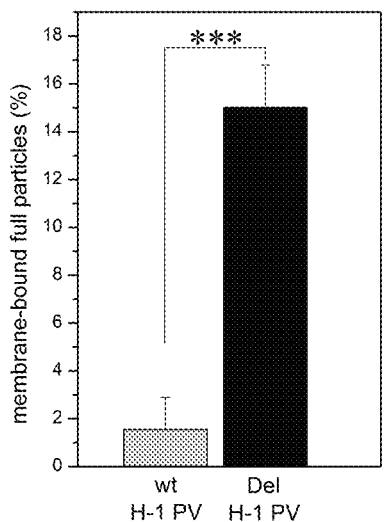
Figure 16:
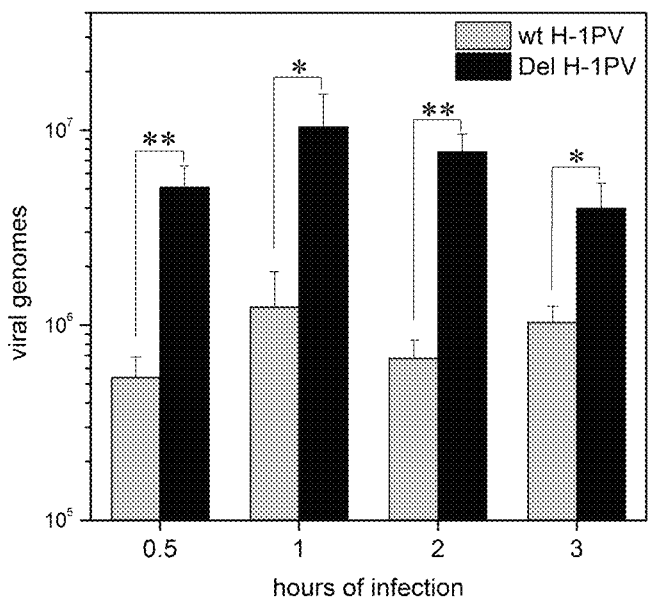

FIG. 16 shows improved cell binding and uptake with Del H-1PV.

(A) $5 \times 10^5$ NB-324K cells were infected for 1 hour at 4° C. with wild type H-1PV or Del H-1PV at a multiplicity of infection of $10^4$ viral genomes per cell. Cell culture medium was removed and cells were washed with PBS prior to cell harvest by scraping. The amount of membrane-bound full particles was determined by quantitative real time PCR after cell lysis and DNA purification and expressed as % of total viral full particles. Data represent means of duplicate measurements ± the standard deviation from two independent experiments. ***p<0.001.

(B) $8 \times 10^4$ NB-324K cells were infected with wild type H-1PV or Del H-1PV at a multiplicity of infection of $10^4$ viral genomes per cell and incubated for 0.5 hour, 1 hour, 2 hours or 3 hours at 37° C. Cell culture medium was removed and membrane-bound viral particles were detached by trypsin/EDTA treatment. The amount of viral particles inside the cells was determined by quantitative real time PCR after cell lysis and DNA purification. Data represent the mean of one representative experiment done in triplicate. *p<0.05; **p<0.01.

Figure 17:
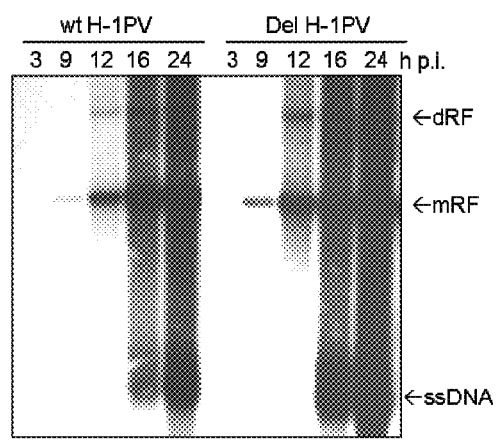
Figure 17:
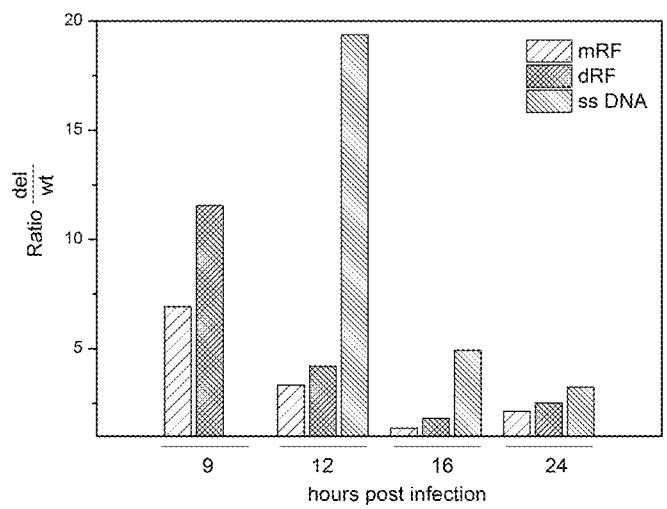

FIG. 17 shows earlier replication of Del H-1PV genome and high accumulation of single-strand DNA in infected NB-324K cells.

(A) $9 \times 10^5$ NB-324K cells were infected with wild type (wt) H-1PV or Del H-1PV at a multiplicity of infection of 6844 viral genomes per cell, and further incubated in presence of neutralizing antibodies PV1 to avoid secondary infections before being harvested at the indicated points of time post-infection (p.i.). Viral DNA replicative forms were extracted from cell lysates, separated by 1%-agarose gel electrophoresis and subjected to Southern-blotting analysis. Viral replicative intermediates were revealed through hybridization with an NS1-specific $^{32}$P-radioactive labelled probe and autoradiography. Positions of dimeric replicative forms (dRF), monomeric replicative forms (mRF), and single-stranded (ss) genome are indicated on the right side of the figure.

(B) Signal intensities corresponding to the monomeric replicative form (mRF), dimeric replicative form (dRF), and single-strand (ss) DNA detected in Del H-1PV or wild type H-1PV infected samples were quantified by a Phospho Imager analysis. Signal intensities were represented as the Del H-1PV over wild type H-1PV ratio of the mRF, dRF, and ss DNA at 9 hours, 12 hours, 16 hours, and 24 hours post-infection.

Figure 18:
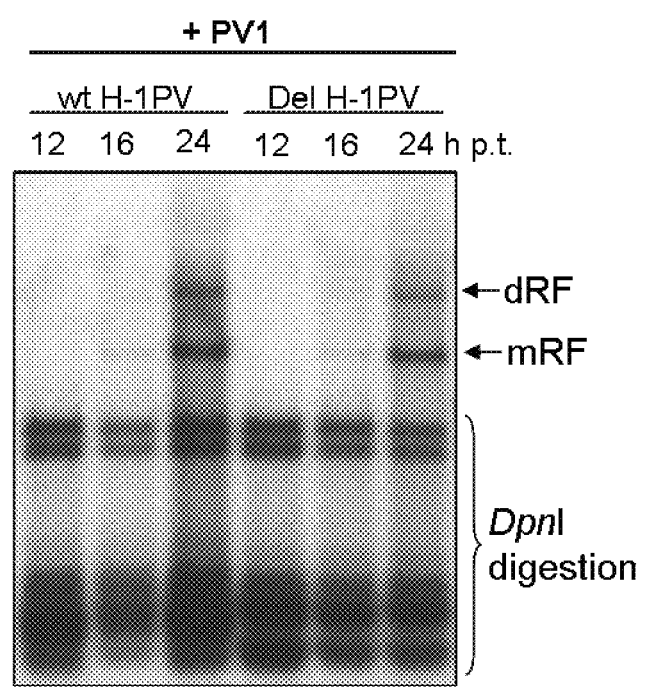

FIG. 18 shows no difference in accumulation of replicative forms upon transfection of NB-324K cells with either Del H-1PV or wild type H-1PV $2\times10^6$ NB-324K cells were transfected with 6 μg of pwtH-1PV or pDel H-1PV plasmid construct and neutralizing antibody PV1 was added in the cell culture medium 4 h post-transfection (p.t.) (+PV1) in order to prevent secondary infections. Cells were harvested at indicated points of time post-transfection and viral DNA molecules were extracted from the cell lysates, subjected to DpnI digestion, analysed by Southern blotting using a $^{32}$P-labelled, NS1-coding region specific probe, and detected upon autoradiography. mRF: monomeric replicative form; dRF: dimeric replicative form.

Figure 19:
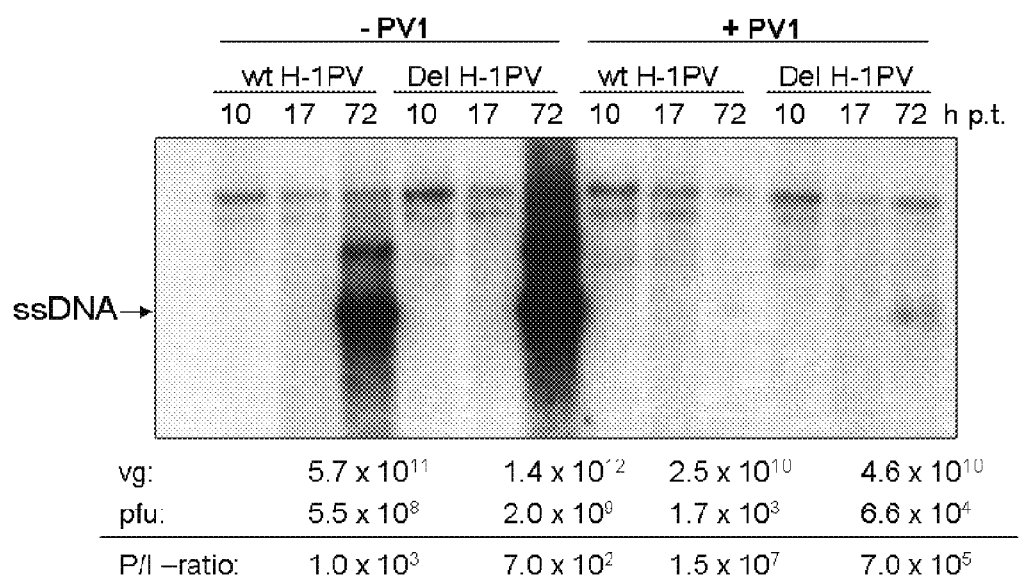

FIG. 19 shows increased and/or faster release of Del H-1PV full virions in the medium of transfected NB-324K cells compared to the release of wild type H-1PV full virions.

$2\times10^6$ NB-324K cells were transfected with 6 μg of pwtH-1PV or pDel H-1PV plasmid construct and further incubated in presence (+PV1) or not (−PV1) of neutralizing antibody PV1. Cell culture supernatant was recovered at indicated points of time post-transfection (p.t.). Single-stranded DNA molecules (ssDNA) were isolated from supernatants of transfected cell cultures by Hirt extraction and analysed by Southern blotting through hybridization with an NS1-specific $^{32}$P-radioactive labelled probe and autoradiography. Additionally, the amount of full viral particles and of infectious viral particles present in the supernatants of transfected NB-324K cells 72 hours post-transfection were analysed by measuring the amount of viral genomes (vg) upon DNase treatment and alkaline lysis by quantitative real-time PCR in the former case and the amount of plaque-forming units (pfu) by plaque assay in the latter case. Virus titers and particle-to-infectivity (P/I)-ratios are given below the autoradiogram.

FIG. 20 shows increased infectivity of Del H-1PV and Del hH-1PV produced by transfection of human 293T cells compared to wild type H-1PV and wild type hH-1PV.

Newly-made Del H-1PV, Del hH-1PV, wild type H-1PV, and wild type hH-1PV virus stocks generated in transfected human 293 T cells were analysed by plaque assay to determine the infectious titer of the stocks (given in PFU per mL) and by quantitative real-time PCR to determine the viral genome titer (given in vg per mL). P/I-ratio: particle-to-infectivity ratio.

DETAILED DESCRIPTION OF THE INVENTION

The present invention provides a parvovirus variant showing higher anti-tumor potential compared to the wild type parvovirus, wherein said variant is characterized by (a) an amino acid substitution, deletion or addition, preferably substitution, at a position corresponding to Lys96 of NS2 and/or position Leu103 of NS2 (the latter one also inducing an amino acid substitution at position Tyr595 of NS1) of H-1PV, or (b) an in-frame deletion in the left-hand part of the H-1PV genome affecting both the central part of NS2 and the C-terminal part of NS1 protein sequences.

The amino acid positions given above are in relation to H-1PV as a reference point, but the skilled person can easily determine the corresponding aa positions in any parvovirus based on the homology of the NS1/NS2 proteins.

Preferably, this deletion has a length of at least 1, preferably at least 10, more preferably at least 20, and even more preferably at least 30 amino acids. Preferably, said deletions are deletions of contiguous amino acids and/or further variations (compared to wild type) are not present. Particularly preferred is an in-frame deletion of nt 2022 to 2135 resulting in the translation of an NS1 protein having a deletion of aa 587-624 and an NS2 protein having a deletion of aa 96-133 (e.g., Del H-1PV).

The term "showing higher anti-tumor potential compared to the wild type parvovirus" means that the growth inhibition of NB-324K cells at 1 day post infection is higher by a factor of at least 1.4, preferably at least 1, 7 and, more preferably, at least 2 compared to the wild type.

The term "parvovirus" as used herein comprises wild type or modified replication-competent derivatives thereof, as well as related viruses or vectors based on such viruses or derivatives. Suitable parvoviruses, derivatives, etc. as well as cells which can be used for producing said parvoviruses are readily determinable within the skill of the art based on the disclosure herein, without undue empirical effort. The expression "parvovirus" comprises any parvovirus, particularly a rodent parvovirus, such as minute virus of mice (MVM) and H-1 virus (H-1PV). The person skilled in the art can introduce amino acid alterations at position Lys96 of NS2 and/or position Leu103 of NS2 (together with one at position Tyr595 of NS1 in the latter case) or large deletions at both positions 96-133 of NS2 and 587-624 of NS1 protein sequences according to standard procedures starting from the known nucleic acid sequence and amino acid sequences of the structural and non-structural proteins of parvoviruses, e.g., from parvovirus H-1PV (see FIGS. 11 and [17], see also [13] and [18] for sequence corrections) The person skilled in the art can also easily assay whether a particular variant exhibits the desired biological properties recited by using the assays explained in the examples, below, e.g., by comparing the increase of infectivity or the inhibition of growth of mammalian cells, e.g., NB-324K cells compared to the wild type.

Preferred are parvovirus variants having either a point mutation at one or several of the sites described above which is an amino acid substitution, or a large deletion of amino acids in both viral NS1 and NS2 protein sequences at the sites described above.

In a more preferred embodiment of the present invention, Lys at position 96 of NS2 is replaced by another hydrophilic polar amino acid (e.g., Arg, Glu, Asp, Gln, or Asn) and/or Leu at position 103 of NS2 is replaced by a neutral nonpolar amino acid (e.g., Pro or Gly), the latter inducing a replacement of Tyr at position 595 of NS1 by a neutral polar amino acid (e.g., Ser, H is or Thr).

In an even more preferred embodiment of the present invention, the parvovirus variant comprises (a) the following amino acid substitution(s) NS2:Lys96Glu, or NS2:Leu103Pro (the latter one also inducing the substitution NS1:Tyr595His), or (b) the following amino acid deletion NS2: Δ96-133 and NS1:Δ587-624.

Particularly preferred are parvovirus variants comprising the following modification(s):

(a) NS2 Lys96Glu substitution (PMut2 H-1PV variant);
(b) NS2 Leu103Pro and NS1 Tyr595H is substitutions (PMut1 H-1PV variant); or
(c) NS2 aa 96-133 and NS1 aa 587-624 deletions (Del H-1PV variant)

Preferably, the parvovirus variant of the invention is derived from parvovirus H-1 (H-1PV) or a related rodent parvovirus. Examples of preferred related rodent parvoviruses are LuIII, Mouse minute virus (MMV), Mouse parvovirus (MPV), Minute virus of mice (MVM), Rat minute virus (RMV), Rat parvovirus (RPV), Rat virus (RV), or Kilham rat virus (KRV).

A further subject matter of the present invention relates to a nucleic acid, particularly a DNA, which codes for an above parvovirus variant.

A DNA according to the invention can be present in a vector and expression vector, respectively. A person skilled in the art is familiar with examples thereof. In the case of an expression vector for *E. coli* these are e.g. pGEMEX, pUC derivatives, pGEX-2T, pET3b, T7 based expression vectors and pQE-8. For the expression in yeast, e.g. pY100 and Ycpad1 have to be mentioned while e.g. pCMV, pCI, pKCR, pEFBOS, cDM8, pMSCND, and pCEV4 have to be indicated for the expression in animal cells. The baculovirus expression vector pAcSGH is NT-A is especially suitable for the expression in insect cells.

In a preferred embodiment, the vector containing the DNA according to the invention is a virus, e.g. an adenovirus, vaccinia virus, an AAV virus or a parvovirus, such as MVM or H-1PV, a parvovirus being preferred. The vector may also be a retrovirus, such as MoMULV, MoMuLV, HaMuSV, MuMTV, RSV or GaLV.

For constructing expression vectors which contain the DNA according to the invention, it is possible to use general methods known in the art. These methods include e.g. in vitro recombination techniques, synthetic methods and in vivo recombination methods.

Furthermore, the present invention relates to host cells which contain the above described vectors. These host cells include bacteria, yeast, insect and animal cells, preferably mammalian cells. The *E. coli* strains HB101, DH1, x1776, JM101, JM109, BL21, XL1Blue, SG 13009, and SURE, the latter being preferred for full parvovirus genome-based vectors, the yeast strain *Saccharomyces cerevisiae* and the animal cells L, A9, 3T3, FM3A, CHO, COS, Vero, HeLa, 293T, and NB-324K, the two latter being preferred for H-1PV vectors, and the insect cells sf9 are preferred. Methods of transforming these host cells, of phenotypically selecting transformants and of expressing the DNA according to the invention by using the above described vectors are known in the art.

Thus, the present invention also provides a method of producing the parvovirus variant of the invention, comprising the culturing of a transformant of the invention under suitable conditions and harvesting the parvovirus variant from the cells or the medium.

Moreover, the present invention relates to antibodies which specifically recognize an above described parvovirus variant NS1 or NS2 protein, i.e. the region of the parvovirus variant protein where the mutation responsible for the higher anti-tumor potential compared with the wild type is located. The antibodies can be monoclonal, polyclonal or synthetic antibodies or fragments thereof, e.g. Fab, Fv or scFV fragments. Preferably monoclonal antibodies are concerned. For the production it is favorable to immunize animals—particularly rabbits or goats for a polyclonal antibody and mice for a monoclonal antibody—with the non-structural protein(s) of an above parvovirus variant or with fragments thereof. Further boosters of the animals can be affected with the same parvovirus variant non-structural protein(s) or with fragments thereof. The polyclonal antibody can then be obtained from the animal serum and can further be purified. The monoclonal antibody can be obtained according to standard methods, reference being made particularly to the method by Köhler and Milstein [19—Nature 256 (1975), 495] and Galfrè and Milstein [20—Meth. Enzymol. 73 (1981), 3]. In this case, mouse myeloma cells are fused with spleen cells originating from the immunized animals. Antibodies according to the invention can be used in many ways, e.g. for the immunoprecipitation of variant non-structural proteins expressed from the above described parvovirus variants or for the isolation thereof. The antibodies can be bound in immunoassays in liquid phase or to a solid carrier. In this connection, the antibodies can be labeled in various ways. The person skilled in the art is familiar with suitable markers and labelling methods. Examples of immunoassays are ELISA, RIA, as well as (co-)immunoprecipitation, immunofluorescence and immunoblotting.

Thus, the present invention provides products which are suitable for therapeutic (and diagnostic) purposes. In particular, expression vectors according to the invention, e.g. parvoviruses, can be used for gene-therapeutic measures. Moreover, parvoviruses variants according to the invention are suitable as toxins, e.g. for treating tumoral diseases.

Therefore, a kit is also provided for the application of the present invention. This kit comprises the following:
(a) a parvovirus variant according to the invention,
(b) a DNA according to the invention, e.g. an expression vector, particularly a parvovirus,
(c) an antibody according to the invention as well as
(d) conventional auxiliary agents, such as solvents, buffers, carriers, markers and controls.

Of component (a) to (d) one or more representatives can be present each.

The present invention also provides a pharmaceutical composition containing a parvovirus variant of the invention, vector or a cell producing said parvovirus variant ("parvotherapeutic agent" or "parvotherapeutic composition"), e.g. human 293(T), human NB-324K or rat RG2 cells.

For administration, the parvotherapeutic agent can be combined with suitable pharmaceutical carriers. Suitable pharmaceutical carriers of a type well known in the art and readily commercially available, include phosphate buffered saline (PBS) solutions, water, emulsions such as oil/water emulsions, wetting agents of various types, contrast media (e.g., VISIPAQUE®), sterile solutions, etc. Such carriers can be formulated with the parvotherapeutic agent(s) by conventional formulating methods for administration to the subject at a suitable dose.

Additional pharmaceutically compatible carriers can include gels, biosorbable matrix materials, implantation elements containing the therapeutic agent, or any other suitable vehicle, delivery or dispensing means or material(s).

Patients treatable by the parvotherapeutic agents of the invention include humans as well as non-human animals. Examples of the latter include, without limitation, animals such as cows, sheep, pigs, horses, dogs, and cats.

Administration of the parvotherapeutic pharmaceutical compositions to a patient, e.g. a brain tumor patient, may be effected in any of numerous suitable ways, e.g., by intravenous, intraperitoneal, subcutaneous, intramuscular, topical, intradermal, intracranial, and intratumoral administration. The route of administration, of course, depends on the nature of the disease and the specific therapeutic agent(s) contained in the pharmaceutical composition.

If such parvotherapeutic agent(s) comprise infectious virus particles with the ability to penetrate through the blood-brain barrier, treatment can be performed or at least initiated by intravenous injection of the viral therapeutic agent, e.g., an H-1PV variant.

Since long-term intravenous treatment is susceptible to becoming inefficient as a result of the formation of neutralizing antibodies to the viral therapeutic agent, different modes of administration can be adopted after an initial regimen of intravenous viral administration, or such different administration techniques, e.g., intracranial or intratumoral virus administration, can be alternatively used throughout the entire course of parvoviral treatment.

As another specific administration technique, the parvotherapeutic agent (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvotherapeutic composition to be injected locally at various times without further surgical intervention. The parvovirus variant or derived vectors can also be injected, e.g., into a tumor, by stereotactic surgical techniques or by neuronavigation targeting techniques.

Administration of the parvoviral agents or compositions can also be performed by continuous infusion of viral particles or fluids containing viral particles through implanted catheters at low flow rates using suitable pump systems, e.g., peristaltic infusion pumps or convection enhanced delivery (CED) pumps.

A yet another method of administration of the parvotherapeutic composition is from an implanted device constructed and arranged to dispense the parvotherapeutic agent to the desired locus, e.g., tumor. For example, wafers can be employed that have been impregnated with the parvotherapeutic composition, e.g., a parvovirus H-1 variant, wherein the wafer is attached to the edges of the resection cavity at the conclusion of surgical tumor removal. Multiple wafers can be employed in such therapeutic intervention.

Cells that actively produce the parvotherapeutic agent, e.g., a parvovirus H-1PV variant, or H-1PV vectors, can be injected into the desired tissue, e.g., tumor, or into a tumoral cavity after tumor removal.

Combinations of two or more of the above-described administration modes can be employed in any suitable manner, e.g., concurrently, contemporaneously, or sequentially.

The dosage regimen of the parvotherapeutic agent is readily determinable within the skill of the art, by the attending physician based on patient data, observations and other clinical factors, including for example the patient's size, body surface area, age, sex, the particular virus, vector, cell, etc. to be administered, the time and route of administration, the type of disease, e.g., tumor type and characteristics, general health of the patient, and other drugs or therapies to which the patient is being subjected.

Accordingly, the present invention also relates to the use of a parvovirus variant according to the present invention, a cell producing said parvovirus variant, a DNA, an expression vector or antibody of the present invention for the preparation of a pharmaceutical composition for the treatment of cancer. Preferred cancers are pancreas carcinoma, cervical carcinoma, hepatoma, and lymphoma being expected to be particularly amenable to treatment with an agent of the present invention.

The below examples explain the invention in more detail.

EXAMPLES

Example 1

Materials and Methods (A) Cells and Reagents

Simian virus 40-transformed human newborn kidney NB-324K cells [21] were propagated in Eagle's minimal essential medium (Sigma-Aldrich), supplemented with 5% fetal bovine serum, glutamine and antibiotics (100 µg/ml Penicillin and 100 U/ml Streptomycin, Gibco/Invitrogen, Karlsruhe, Germany).

Human PDAC cell lines Panc-1 and MiaPaCa-2 (established from primary tumors) were kindly provided by A. Vecchi (Instituto Clinico Humanitas, Rozzano, Italy). The human HeLa+ cell line was kindly provided by E. Schwarz (German Cancer Research Center, Heidelberg, Germany). Panc-1, MiaPaCa-2, and HeLa+ cells were grown in Dulbecco's modified Eagle's medium (DMEM, Sigma-Aldrich, Taufkirchen, Germany) supplemented with 10% fetal bovine serum (PAA Laboratories, Pasching, Austria), and 2 mM L-glutamine (Gibco/Invitrogen).

The SV40 T antigen-, Ad5-transformed human embryonic kidney 293T cell line [28] was cultivated in Dulbecco's modified Eagle medium (DMEM, Sigma), supplemented with 10% of FCS, 2 mM of L-glutamine, 100 U/mL of penicillin and 100 µg/mL of streptomycin.

(B) Virus Infection and Production

Virus infections were performed at 37° C. for 1 hr with an inoculum of 400 µl per 6-cm cell culture dish (Sarstedt, Nürnbrecht, Germany) of purified virus diluted in cell culture medium without supplements and periodical rocking of the plate.

Del H-1 PV and PMut H-1PV variants were primarily produced by transfection of 293T cells as described previously [18] using the appropriate plasmid construct. H-1PV variants, as well as wild type H-1PV, were subsequently produced by infection of NB-324K cells at a low multiplicity of infection (moi), i.e., $10^3$ PFU/cell. At day 3 post-infection or upon appearance of cytopathic effects, cells were harvested and lysed in VTE buffer (50 mM Tris pH 8.7, 0.5 mM EDTA) by means of three freeze-thaw cycles. Cell debris was removed by centrifugation and virus stocks were purified by iodixanol step gradient centrifugation [22].

For the measurement of progeny virus production, $1 \times 10^5$ cells were infected with H-1PV variants or wild type H-1PV at a moi of 0.5 PFU/cell. At various time points post-infection, medium was collected and the infected culture was harvested and subjected to three freeze-thaw cycles in VTE buffer. The virus titers were determined for both the cell extract and the culture medium by plaque assay.

(C) Titration of Infectious Virus

Virus stocks were titered by plaque assay [23] or by infected cell hybridization assay [24] on NB-324K indicator cells. Virus titers are expressed as plaque forming units (PFU) or replication units (RU) per milliliter of virus suspension as described elsewhere [18, 23, 25].

(D) Titration of Full Virus Particles

The amount of full virus particles present in a virus stock was determined by quantitative dot blot hybridization assays as described previously [26] and expressed as full viral particles per milliliter of virus suspension.

(E) Measurement of Growth Inhibition

The growth kinetics of infected NB-324K cells was monitored by electronic pulse area analysis using a Casy cell counter system (Casy, Reutlingen, Germany).

(F) Immunoblotting $1.5 \times 10^5$ NB-324K cells were infected with Del H-1PV, PMut1 H-1PV, PMut2 H-1PV or wild type H-1PV at a moi of 3 PFU/cell. Cells were harvested at 6, 8, 24 and 48 hours after infection and lysed in RIPA buffer (150 mM NaCl, 10 mM Tris pH 7.5, 1 mM EDTA pH 8.0, 1% NP-40, 0.5% sodium deoxycholate, 0.1% SDS) supplemented with protease inhibitors (Roche, Germany). After protein quantification (Bio-Rad Protein Assay, Bio-Rad Laboratories, Munich, Germany) 10 µg of total proteins were separated by SDS 12%-polyacrylamide gel electrophoresis (SDS-PAGE) and electro-transferred to Protran nitrocellulose membranes (PerkinElmer Life Sciences, Überlingen, Germany). The membranes were incubated first with either rabbit polyclonal antiserum directed against NS1 (SP8, [27]), against NS2

(α-NS2p, [18]) or against viral capsid proteins (α-VPpep, [25]) and second with the appropriate secondary horseradish peroxidase-coupled antibody (Promega, Mannheim, Germany). Immunoreactive proteins were further revealed by enhanced chemiluminescence (GE Healthcare Europe, Freiburg, Germany).

(G) Nuclear and Cytoplasmic Protein Fractionation from Infected Cultured Cells $5 \times 10^5$ NB-324K cells were infected at a moi of 1 PFU/cell with Del H-1PV, PMut1 H-1PV, PMut2 H-1PV, PMut4 H-1PV or wild type H-1PV. 16, 20, 24 and 42 hours after infection, cells were harvested and a nuclear and cytoplasmic protein fractionation was performed using the NE-PER Nuclear and Cytoplasmic Extraction Reagents Kit (Thermo Fisher Scientific, Rockford, USA) according to the manufacturer's instructions. The number of infectious particles present in each fraction was determined by plaque assay and expressed as total PFU.

(H) Measurement of Cell Clonogenicity

NB-324K cells were infected with wild type H-1 PV or Del H-1 PV at various moi. 4 hours after infection cells were harvested by trypsinization and re-seeded onto 6-cm cell culture dishes as single cells, i.e., 100 to 200 cells per dish. After 13 to 17 days of incubation in complete medium containing 2.5% of anti H-1 capsid serum PV1, the cells were fixed and stained with crystal violet solution (1 g crystal violet diluted in 100 ml EtOH 70%). Cell colonies were counted and expressed for each moi as a percentage of surviving cells compared to mock-treated cells.

(I) Immunofluorescence $1.5 \times 10^4$ NB-324K cells were grown on coverslips (Diagnostic microscope slides, Erie Scientific Company, Portsmouth, USA) and infected with Del H-1PV or wild type H-1PV at a moi of 3 PFU/cell. 15 and 21 hours after infection, cells were fixed in 3.7% formaldehyde for 10 min, treated with cold methanol for 5 min, cold acetone for 2 min and permeabilized with 0.2% Triton X-100 ([4-(1,1,3,3-Tetramethylbutyl)phenol]ethoxylate) for 10 min. After washing with PBS, the cells were treated with a blocking solution containing 10% fetal bovine serum for ca 30 min. Cells were then successively incubated with the monoclonal mouse antibody 3C3F12 (1:100 dilution) (C. Dinsart, unpublished) as primary antibody, and with a donkey anti-mouse alexa fluor 488-conjugated antibody (1:600 dilution; Santa Cruz Biotechnology, Eugene, Oreg., USA) as secondary antibody, for 1 hour each at room temperature, followed by three phosphate-buffered saline washes. All solutions and dilutions were prepared in phosphate-buffered saline. After a quick staining of the DNA with DAPI (4',6-diamidino-2-phenylindole), coverslips were dried with ethanol and mounted onto glass slides in the presence of polyvinyl alcohol (Elvanol; Serva, Heidelberg, Germany). Samples were examined with a Leica DMRBE microscope at a x63 magnification with an oil immersion objective and images were captured with a Hamamatsu Orca digital camera and processed using the Openlab2 (Improvision, UK) and Adobe Photoshop CS2 softwares. In order to determine the percentage of a certain phenotype, 200 cells per phenotype were examined.

(J) In Vivo Measurement of Tumor Suppression $4 \times 10^7$ Panc-1 cells were infected in vitro with either Del H-1PV or wild type H-1PV at a moi of 3 RU/cell. 4 h after infection $5 \times 10^6$ cells per mouse were implanted subcutaneously (s.c.) into the right flank of Balb/c nude mice. 7 nude mice were injected with mock-treated (i.e., buffer-treated) cells, 7 nude mice were injected with wild type H-1PV-infected cells whereas 6 nude mice were injected with Del H-1PV-infected cells.

The mice (6- to 7-week-old females, five animals per cage) were maintained in isolators at 21-24° C., 40-60% humidity. Tumor sizes were measured with a calliper two to three times a week over a time period of about 3 months. The tumor volume was calculated according to the formula $V=\frac{1}{2} \times \text{length} \times (\text{width})^2$ and expressed either in the mean of the total volume ($mm^3$) or in percentage of mice of one group bearing a tumor bigger than 290 $mm^3$.

$1 \times 10^6$ HeLa cells were injected subcutaneously into the right flank of Balb/c nude mice. 9 days post-implantation, 5 nude mice were injected with 100 µl of PBS each, 5 nude mice were injected with $10^8$ pfu of Del H-1PV (in 100 µl PBS) each, 5 nude mice were injected with $10^8$ pfu of wild type H-1PV (in 100 µl PBS) each. Mice (6- to 7-week old females, 5 animals per cage) were maintained in isolators at 21° C.-24° C., 40-60% humidity. Tumor sizes were measured with a calliper two to three times a week over a time period of about 6 weeks. The tumor volume was calculated according to the formula $V=\frac{1}{2} \times \text{length} \times \text{width}^2$ and expressed either in the mean of the total volume (mm3) or in percentage of mice of one group bearing a tumor bigger than 1000 $mm^3$.

(K) Pulse-Chase Metabolic Radiolabeling and Cell Extracts $9 \times 10^5$ NB-324K cells were infected with either Del H-1PV or wild type H-1PV at a MOI of 3 PFU/cell or mock infected (i.e., buffer treated). 18 h after infection cultures were metabolically labelled for 30 min with 200 µCi of Tran$^{35}$S-label (1175 Ci/mmol; MP Biomedicals) in Met- and Cys-free Dulbecco's modified Eagle's medium (DMEM) supplemented with 5% dialyzed fetal calf serum, 1% L-glutamine and 1% gentamycine. Afterwards the labelling medium was aspired and cells were washed once with MEM without serum. Cells were either lysed subsequently or re-incubated at 37° C. in unlabeled complete medium (chase) and further lysed at various points of time post-incubation in order to investigate the degradation of labelled, synthesized proteins. Lysis was performed using RIPA buffer (150 mM NaCl, 10 mM Tris [pH 7.5], 1 mM EDTA [pH 8.0], 1% [v/v] Nonidet P-40, 0.5% Sodium Deoxycholate, 0.1% [w/v] Sodium Dodecylsulfate (SDS)) supplemented with a mixture of proteinase inhibitors (Complete, Roche, Mannheim, Germany). Proteins were harvested after removing cell debris by centrifugation in an Eppendorf centrifuge at full speed for 10 min at 4° C.

(L) (Co-) Immunoprecipitation of Cellular and Viral Proteins $5 \times 10^6$ cpm of labelled protein extracts were incubated at 4° C. for 1 hour under continuous rotation (Reax 2, Heidolph) and in presence of 8 to 10 µl of polyclonal rabbit antiserum directed either against H-1PV NS1, H-1PV NS2, human CRM1 or 14-3-3 proteins and further incubated 1 hour at 4° C. after adding 100 µl of protein A sepharose (6 MB, GE Healthcare) to each sample. Samples were centrifuged for 5 min at 5500 rpm and 4° C. (Sigma 2K15). Protein-antibody-beads complexes were then washed three times with each 1 ml of RIPA (+/−SDS) buffer. Sample pellets were resuspended in an appropriate volume of 2×SDS-loading dye (80-100 µL) and proteins were separated by 12% [w/v] polyacrylamide gel electrophoresis. After 30 min incubation with Amplify (Amersham), gels were dried and further exposed to autoradiographic films (BioMax, MS Film, Kodak).

(M) Heat-Denaturation of Virus and Detection of Packaged Viral DNA by Quantitative Real-Time PCR A DNAse-buffer-dilution (400 mM Tris-HCl [pH 8.0], 100 mM $MgSO_4$, 10 mM $CaCl_2$; Promega, Mannheim, Germany) containing $10^9$ full viral particles of either purified Del H-1PV or purified wild type H-1PV was heated to a defined temperature (temperatures ranged from 50° C. to 70° C. and generated with a PCR machine) for 10 minutes. Samples were treated subsequently with DNAseI [0.1 U/µl; Promega, Mannheim, Germany] for 1 h at 37° C. In order to be able to determine the number of intact capsids, viral particles were destroyed by alkaline lysis and packaged viral DNA was detected by quantitative real-time PCR as described elsewhere [29], using the Mastercycler® ep realplex (Eppendorf, Hamburg, Germany). Individual reaction mixtures (20 µl) contained 1×TaqMan Universal PCR Master Mix™ (Applied Biosystems), 0.28 µM labelled NS1-TagMan™ probe, 0.28 µM of each forward and reverse primer and 2.85 µl template. Virus titers were expressed as viral genomes per ml of virus suspension (vg/ml) and calculated according to the following equation:

$$\text{Virus titer}[vg/ml] = I_{Qf}[1/ml] \cdot 35000$$

Factor $35000 = [46.7\ \mu l/(6.7\ \mu l \times 20\ \mu l)] \times (100\ \mu l/10\ \mu l) \times 1000\ \mu l$ IQ denotes the quantified fluorescence intensity of a sample and the factor 35000 is needed to calculate the quantity per well (46.7 µl/(6.7 µL×20 µl), per 10 µl of virus suspension used for alkaline lysis (1000 µl/10 µl) and per ml (1000 µl) in order to express the virus titer per ml of the virus stock solution.

(N) Virus Binding to Human NB-324K Cells $5 \times 10^5$ human NB-324K cells were infected with wild type H-1PV or Del H-1PV at a MOI of 104 vg/cell and further incubated for 1 hour at 4° C. Cells were washed with ice-cold 1×PBS, scraped in 500 µl 1×PBS, and pelleted by centrifugation for 5 min at 3500 rpm and 4° C. (centrifuge 5417R, Eppendorf). Supernatants were saved in Eppendorf tubes. Cells were next resuspended in 200 µl of ice-cold 1×PBS and DNA was purified after cell lysis using the DNeasy Blood and Tissue Kit (Qiagen) according to the manufacturer's instructions. Cell lysates were incubated at 85° C. for 30 min (HBT 130, Haep Labor Consult) in order to denature the viral particles, and released viral DNA was recovered by Hirt extraction. Quantification of the viral genomes present either in the supernatant fraction or bound to the cells was determined by quantitative real-time PCR as described elsewhere [28].

(O) Virus Uptake $8 \times 10^4$ NB-324K cells were infected with wild type H-1PV or Del H-1PV at a MOI of 104 vg/cell and further incubated at 37° C. At points of time post-infection (ranging from 0.5 to 3 h), cells were washed with 1×PBS and membrane-bound viral particles were detached by Trypsin/EDTA (Invitrogen) treatment. Cells were then pelleted by centrifugation for 5 min at 3500 rpm and room-temperature (centrifuge 5417R, Eppendorf). Cells were lysed using the DNEASY® Blood and Tissue Kit (Qiagen, kits for the isolation of nucleic acids from cells) according to the manufacturer's instructions and internalized viral DNA was extracted by Hirt extraction. Quantification of internalized viral genomes was determined by quantitative real-time PCR as described elsewhere [28].

(P) Extraction of Low-Molecular Weight Viral DNA from Mammalian Cells (Hirt Extraction)

Extraction of low molecular weight viral DNA from infected or transfected cells or from cell supernatants was performed either by Hirt extraction as described elsewhere [30] or with the DNEASY® Blood and Tissue Kit (Qiagen).

(Q) Southern-Blotting

Viral DNA replicative forms were separated by 1%-agarose gel electrophoresis. Upon two denaturation treatments for 30 min each and two neutralization treatment for 15 min each of the gel, DNA molecules were transferred onto a nitrocellulose filter (Protran, GE Healthcare) for 15-20 hours at room temperature by capillary action in presence of 10×SSC buffer. Membrane was removed from the blot and DNA molecules were immobilized by UV-treatment of the membrane. The membrane was afterwards hybridized with a $^{32}$P-radioactive labelled NS-specific probe and further exposed on autoradiographic films (BioMax, MS Film, Kodak) at −80° C.

(R) Transfection

Transfection Using CaPO$_4$

6 µg of pwtH-1PV and pDelH-1PV plasmid DNA were precipitated in a mixture of a HEPES buffered saline solution and a calcium chloride (CaCl2) solution as described elsewhere [28] and further added to $2 \times 10^6$ 293T cells cultured in a 10-cm dish in complete medium before incubation at 37° C. and 5% CO$_2$.

Transfection Using Lipofectamine 2000

30-60 min prior to transfection, complete cell culture medium was exchanged by fresh medium devoid of supplements. In the meantime, 6 µg of pwtH-1PV and pDelH-1PV plasmid DNA was diluted in OPTI-MEM (Invitrogen) and a mixture of Lipofectamine 2000 (Invitrogen) and OPTI-MEM was prepared, as described in the manufacturer's protocol. The two solutions were mixed and after incubation at room-temperature for 25 min, the mixture was added dropwise to the cell culture medium of subconfluent NB-324K cells. 4 h post-transfection (p.t.), the transfection medium was replaced by fresh, complete cell culture medium.

Example 2

Construction of Parvovirus Variants (A) Del H-1PV Variant

The deletion in the NS-coding sequence of H-1PV genome (i.e., Δ2022-2135 nts) was constructed by PCR with the help of the pSR19 plasmid [13] and the primers listed in Table 1. The ApoI-HindIII fragment containing the deleted region was excised from the mutated DNA and subsequently substituted for the equivalent wild type ApoI-HindIII fragment in the desired vector to generate the pDelH-1PV plasmid construct. The construct was verified by sequencing the entire substituted ApoI-HindIII fragment (GATC Biotech, Constance, Germany).

TABLE 1

| Construct | Template | Primer sequence (5'→3') |
|---|---|---|
| pDelH-1PV | pSR19 | ¹ctataaattcgctaggttcaatgcgctcaccatctctgactc cgagccaaaacactggggaggctggttcc (SEQ ID NO: 1) |
| | | ²gaaagcttaggtgcaaaagctcgcttgg (SEQ ID NO: 2) |

¹Forward and ²reverse primers.

(B) PMut H-1PV Variants

Introduction of single and double point mutations into the infectious H-1PV clone pSR19 was performed by site-directed mutagenesis using the QUICKCHANGE® Site-Directed Mutagenesis Kit (Stratagene, Amsterdam, The Netherlands) according to the manufacturer's instructions and the primers described in Table 2. All the constructs were verified by sequencing (GATC Biotech, Constance, Germany).

TABLE 2

| Construct | Template | primer sequence (5'→3') |
|---|---|---|
| pPMut1H-1PV | pSR19 | ¹cgcctctcagccaaaaccacgctcttactccac (SEQ ID NO: 3) |
| | | ²gtggagtaagagcgtggttttggctgagaggcg (SEQ ID NO: 4) |
| pPMut2H-1PV | pSR19 | ¹atctctgactccgaggagtacgcctctcagc (SEQ ID NO: 5) |
| | | ²gctgagaggcgtactcctcggagtcagagat (SEQ ID NO: 6) |
| pPMut3H-1PV | pSR19 | ¹caacggagcccaacatggtccgagatcga (SEQ ID NO: 7) |
| | | ²tcgatctcggaccatgttgggctccgttg (SEQ ID NO: 8) |
| pPMut4H-1PV | pPMut1H-1PV | ¹atctctgactccgaggagtacgcctctcagc (SEQ ID NO: 9) |
| | | ²gctgagaggcgtactcctcggagtcagagat (SEQ ID NO: 10) |

¹Forward and ²reverse primers. Mutated nucleotides are underlined.

Example 3

Increased Infectivity of Del H-1PV Compared to Wild Type H-1PV and Similar or Even Better Infectivity of PMut1 H-1PV and PMut2 H-1PV Variants Compared to Del H-1PV The infectivity of a virus stock is defined by the ratio of full viral particles (P) to infectious particles (I), i.e. the P/I ratio. Therefore, the lower the P/I ratio the higher the infectivity of the virus stock is.

FIG. 2 shows the P/I ratio (particle-to-infectivity ratio) of the various deletion and point mutant H-1PV variants compared to the one of wild type H-1PV from virus stocks newly-generated in NB-324K cells. For each virus stock, the amount of full particles was determined according to the genome titre of this stock whereas the amount of infectious particles was determined according to the capacity of full particles (i) to form plaque (given in plaque-forming unit or PFU), and (ii) to replicate their genome (given in replicative unit or RU) in the reference NB-324K cell line. Two P/I ratios were further determined by comparing the amount of full particles (i.e., capsids containing a viral genome):
 first to the amount of pfu (characterizing full virions able to spread in the culture via cell lysis) (FIG. 2 ratio 1), and
 second to the amount of ru (characterizing full virions able to amplify their genome) (FIG. 2 ratio 2).

As shown in FIG. 2, PMut1 H-1PV and PMut2 H-1PV point mutant variants as well as Del H-1PV deletion variant exhibited a lower P/I ratio than wild type H-1PV with regard to the ability of full particles either to amplify their genome (FIG. 2; ratio 2) or to propagate in the cell culture (FIG. 2; ratio 1). Indeed the P/I ratio of both Del H-1PV and PMut2 H-1PV and the one of PMut1 H-1PV is lower with a factor of at least 5 and 8, respectively, compared to the P/I ratio of wild type H-1PV. This indicates a higher infectivity of these variants with PMut1 H-1PV showing the highest level.

In contrast, PMut3 H-1PV and PMut4 H-1PV point mutant variants exhibited a higher, and therefore worse, P/I ratio than the three other variants (Del H-1PV, PMut1 H-1PV, and PMut2 H-1PV) with regard to the ability of full virions both to amplify their genome and to propagate. These two variants also exhibited a worse P/I ratio (i.e., 2-fold higher) than wild type H-1PV, at least according to their ability to propagate in the cell culture. These data indicate a reduced infectivity of both PMut3 H-1PV and PMut4 H-1PV point mutant variants. It is worth noting that point mutations, which were introduced in PMut1 and PMut2 H-1PV, alone increased the infectivity of the variant whereas a combination of both point mutations, as in PMut4 H-1PV, appeared to have an opposite effect and led to more non infectious than infectious full particles.

In summary, the infectivity of the point mutant variant PMut1 H-1PV (NS2 Leu103Pro & NS1 Tyr595His) is even better than the one of either the deletion variant Del H-1PV (Δ nt 2022-2135) or the point mutant variant PMut2 H-1PV (NS2 Lys96Glu), which infectivity of the two latter was already significantly increased (i.e., by at least a factor of 5) compared to the one of wild type H-1PV.

Example 4

Increased and/or Faster Propagation of Del H-1PV Compared to Wild Type H-1PV in Infected NB-324K Cells Virus production of the deletion variant Del H-1PV and of the point mutant variants PMut1 H-1PV, PMut2 H-1PV, and PMut3 H-1PV as well as of wild type H-1PV were analysed by plaque assay. Besides allowing determining a titer, this method shows the ability of a virus to form plaques that means its ability to infect neighboring cells and thereby to spread in a monolayer cell culture. It is worth noting that a plaque assay always gives rise to a mixture of small and large plaques whatever the virus stock, probably due to the fact that cells are at various stages of the cell cycle when being infected although parvovirus replication cycle can only start at the S-phase of the cell cycle. However, the bigger the plaques and the higher the amount of big plaques produced by a virus is, the better is the ability of this virus to propagate in a cell culture.

FIG. 3A illustrates the size of the plaques formed by the various H-1PV variants and by wild type H-1PV in the reference NB-324K cell line. PMut3 H-1PV clearly produced smaller plaques than wild type H-1PV, suggesting a lower propagation efficacy of this mutant at least in human NB-324K cells. These data are also in agreement with the above-described lower infectivity of this variant in NB-324K cells (see example 3 and FIG. 2).

In contrast, the plaques produced by the three other variants PMut1 H-1PV, PMut2 H-1PV, and Del H-1PV were in general larger than those obtained with PMut3 H-1PV, suggesting a better propagation efficacy with these variants. However, PMut2 H-1PV and PMut1 H-1PV seemed to produce smaller and bigger plaques, respectively, than the ones obtained with wild type H-1PV. Further experiments will be performed in order to determine the various sizes of the plaques formed by these two point mutant variants and their proportion compared to those obtained with wild type H-1PV or Del H-1PV.

As shown FIG. 3A, the deletion variant Del H-1PV produced larger plaques than wild type H-1PV. Indeed as shown FIG. 3B, a higher proportion of large plaques, i.e., above 25 mm$^2$, was formed upon infection with Del H-1PV variant whereas wild type H-1PV produced a higher proportion of small plaques, i.e., up to 20 mm$^2$. Moreover, Del H-1PV gave rise to a higher average and maximal size of plaques (19 mm$^2$ and 118 mm$^2$, respectively) compared to wild type H-1PV (13 mm$^2$ and 67 mm$^2$, respectively). In other words, the plaque size average obtained with the Del H-1PV variant is higher from a factor of 1.5 compared to the one obtained with wild type H-1PV, suggesting a better propagation efficacy and/or a faster infectious cycle of the Del H-1PV variant. These data are also in agreement with the above-described higher infectivity of this Del H-1PV variant in NB-324K cells (see Example 3 and FIG. 2).

In summary, propagation of the deletion variant Del H-1PV (Δ nt 2022-2135) is increased and/or faster compared to wild type H-1PV in NB-324K cells. Whether the point mutant variant PMut1 H-1PV (NS2 Leu103Pro & NS1 Tyr595His) propagates similarly to or better than wild type H-1PV will be further determined.

Example 5

Viral Protein Accumulation in Infected NB-324K Cells

Accumulation of the viral proteins was determined by immunoblotting assays in NB-324K cells infected with Del H-1PV, PMut1 H-1PV, PMut2 H-1PV, or wild type H-1PV. FIG. 4 shows the accumulation of the non-structural NS1 and NS2 and capsid VP proteins 6 hours, 8 hours, 24 hours, and 48 hours post-infection.

All the tested viruses were able to express non-structural and capsid proteins; however, the accumulation pattern of these proteins was different for each virus.

In all infected NB-324K cells, the capsid proteins VP1 and VP2 were detectable 24 h and 48 h post-infection but not at the earlier 6 h and 8 h points of time. 24 h post infection, cells infected with the deletion and point mutant variants showed higher amounts of VP proteins compared to wild type H-1PV infected cells (FIG. 4, black arrows). Between 24 h and 48 h post-infection, Del H-1PV led to a strong increase in VP protein accumulation whereas no or only a slight increase of VP proteins was observed with PMut1 H-1PV and PMut2 H-1PV variants or with wild type H-1PV.

In contrast to wild type H-1PV and to Del H-1PV infection, the non-structural protein NS1 was already detectable 8 h post-infection with either PMut1 H-1PV or PMut2 H1-PV (FIG. 4, red arrows). Moreover, these two point mutant variants also led to higher accumulation level of NS1 as observed 24 h and/or 48 h post-infection compared to the one obtained with wild type H-1PV or Del H-1PV, the latter appearing to give rise to the lowest accumulation level of NS1 at least within the analyzed period of time post-infection.

Although in all cases no NS2 protein could be detected early in infection, i.e., 6 h or 8 h post-infection, the accumulation pattern of NS2 was strikingly different between all 4 viruses later in infection (FIG. 4, black boxes). Between 8 h and 24 h post-infection, NS2 accumulated to detectable level with all viruses except Del H-1PV. At 24 h and 48 h points of time post-infection, the level of NS2 accumulation was similar in cells infected with wild type H-1PV but significantly increased or decreased upon infection with PMut1 H-1PV or PMut2 H-1PV, respectively. In cells infected with Del H-1PV, NS2 was only hardly detectable at the latest analyzed point of time, i.e., 48 h post-infection.

In summary, the point mutant variants PMut1 H-1PV (NS2 Leu103Pro & NS1 Tyr595His) and PMut2 H-1PV (NS2 Lys96Glu), both appearing to be highly cytotoxic (see example 6 and FIG. 5), gave rise to an earlier and to higher accumulation of the non-structural protein NS1 whereas the deletion variant Del H-1PV (Δ nt 2022-2135), appearing to propagate faster (see example 4 and FIG. 3), gave rise to an higher accumulation of the capsid proteins VP1 and VP2 and the lowest accumulation of the non-structural protein NS2 at least in the reference human NB-324K cell line and within the period of time analyzed.

Example 6

Increased Cell Culture Growth Inhibition and Increased Production of Infectious Progeny Virions with PMut1 H-1PV and PMut2 H-1PV Variants The cytotoxic and productive properties of the point mutant variants PMut1 H-1PV and PMut2 H-1PV were compared to the ones of the deletion variant Del H-1PV and of the wild type H-1PV in infected human NB-324K. Therefore both cell culture growth and production of infectious progeny virions were followed up over a 4-day period of time. On the one hand, the amount of living and dead cells was measured using a Casy cell counter system and FIG. 5A shows the average percentage of living cells based on the average of living cells obtained in mock-treated cells. On the other hand, the amount of newly-made virions able to form plaques was determined by plaque assay and FIG. 5B shows the amount of total plaque-forming units obtained at days 1, 2, 3, and 4 post-infection.

As shown FIG. 5A, all viruses were able to inhibit the cell culture growth, the deletion variant Del H-1PV and the wild type H-1PV showing similar levels of cell growth inhibition at least day 1 post-infection. However a much higher cytotoxic effect, i.e., a stronger inhibition of cell population growth with a factor of about 1.5 and 2, was clearly observed upon infection of NB-324K cells with the point mutant variants PMut1 H-1PV and PMut2 H-1PV, respectively, when compared to Del H-1PV or wild type H-1PV infected cells at least 1 day post-infection.

As shown FIG. 5B, all viruses were able to produce infectious progeny virions in human NB-324K cells. However, both point mutant variants PMut1 H-1PV and PMut2 H-1PV as well as the deletion variant Del H-1PV gave rise to a higher production of infectious progeny virions compared to wild type H-1PV, showing an increase of about 12-fold, 7.5-fold, and 5-fold, respectively, in the amount of total plaque-forming units at least 1 day post-infection.

In summary, the point mutant variants PMut1 H-1PV (NS2 Leu103Pro & NS1 Tyr595His) and PMut2 H-1PV (NS2 Lys96Glu) inhibit the growth of NB-324K cell population even more than the deletion variant Del H-1PV (Δ nt 2022-2135) and than wild type H-1PV. All three variants, i.e., PMut1 H-1PV, PMut2 H-1PV and Del H-1PV, also gave rise to a higher production of infectious progeny virions as wild type H-1PV did at least in human NB-324K cells.

Example 7

Pfu-Distribution in the Nucleus and Cytoplasm of Infected Human NB-324K Cells

FIG. 6 shows the production and the intra-cellular distribution of infectious progeny virions in NB-324K cells infected either with wild type H-1PV or with the variant Del H-1PV, PMut1 H-1PV or PMut2 H-1PV and in absence of secondary infections. Infectious progeny virions present in the nuclear and cytoplasmic fractions of the cells were quantified 16 hours, 20 hours, 24 hours and 42 hours post-infection by plaque assay and represented as plaque-forming units (i.e. plaque-forming particles or virions).

As shown FIG. 6a, the amount of plaque-forming, i.e., infectious, progeny virions that was recovered from the nuclear fraction of NB-324K cells was equivalent and similarly increasing with time upon infection with either Del H-1PV or wild type H-1PV at all tested points of time.

In contrast and as shown FIG. 6b, a significantly higher amount of plaque-forming virions was recovered from the cytoplasmic fraction 24 h and 42 h post-infection in Del H-1PV compared to wild type H-1PV infected NB-324K cells. These data clearly showed an increased production of progeny virions as a result of a primary infection together with an earlier and/or increased export of newly-made infectious virions from the nucleus to the cytoplasm of NB-324K cells upon infection with Del H-1PV compared to wild type H-1PV infected cells.

The accumulation pattern of plaque-forming progeny virions in the nuclear fraction of NB-324K cells infected with PMut1 H-1PV, PMut2 H-1PV or PMut4 H-1PV was different to the one obtained upon infection with either wild type H-1PV or Del H-1PV.

As shown in FIG. 6c, the double point mutant variant PMut4 H-1PV gave rise to a much higher amount of plaque-forming particles in the nuclear fraction of NB-324K cells, i.e., with an increased factor of 7 at 20 h and of 5 at 24 h post-infection, compared to all other viruses tested. 24 h post-infection, PMut1 H-1PV also gave rise to a significantly higher amount of plaque-forming particles in the nuclear fraction of NB-324K cells compared to PMut2 H-1PV, Del H-1PV, and wild type H-1PV. It is interesting to note that the amounts of plaque-forming particles found in the nucleus upon infection with PMut1 H-1PV, PMut2 H-1PV, or PMut3 H-1PV dropped between the 24 h and 42 h points of time post-infection in contrast to the deletion variant Del H-1PV or wild type H-1PV.

In the cytoplasmic fraction and as shown in FIG. 6d, the double point mutant variant PMut4 H-1PV showed a clear increase in the amount of plaque-forming particles 20 h, 24 h, and 42 h post-infection compared to wild type, which amount even approximated the one obtained with Del H-1PV at least 42 h post-infection. The single point mutant variant PMut1 H-1PV also gave rise to a higher amount of plaque-forming progeny virions compared to wild type H-1PV, at least 24 h and 42 h post-infection, but not as high as the one obtained with Del H-1PV. In contrast to the other variants, the amount of plaque-forming particles found in the cytoplasm of NB-324K cells infected with PMut2 H-1PV remained virtually constant at all tested points of time and thereby stayed lower than the one found in samples infected with wild type H-1PV. The latter data suggest that some step(s) of the infectious cycle allowing an increased cytoplasmic accumulation of progeny virions might be impaired with PMut2 H-1PV variant in contrast to the other variants.

In summary, both the deletion variant Del H-1PV (Δ nt 2022-2135) and the double point mutant variant PMut4 H-1PV (NS2 Lys96Glu, Leu103Pro & NS1 Tyr595His) showed a clear increased production of progeny virions compared to wild type, PMut4 H-1PV also showing an earlier accumulation in the nucleus and Del H-1PV showing an earlier nuclear export of newly-made infectious virions compared to wild type. The single point mutant variant PMut1 H-1PV (NS2 Leu103Pro & NS1 Tyr595His) seems to behave similarly to the double point mutant variant PMut4 H-1PV, although with lower amounts of plaque-forming particles at least at the points of time tested, whereas the single point mutant variant PMut2 H-1PV (NS2 Lys96Glu) appears to be impaired in its ability to cumulate infectious progeny virions in the cytoplasm of infected cells.

Example 8

Some Steps of the Del H-1PV Life Cycle are Faster than that of Wild Type H-1PV

FIG. 7 shows the accumulation and the subcellular localization of viral particles at a single cell level in infected NB-324K as detected by immunofluorescence assays 15 hours and 21 hours post-infection. In this experiment, human NB-324K cells were infected with either the hybrid (h) deletion variant Del hH-1PV or the hybrid wild type hH-1PV, in which the left hand part of the H-1PV genome was replaced by the equivalent region, i.e., from nucleotide 1 to nucleotide 990, of the genome from the closely related parvovirus MVMp (retrieved from the pdB-MVp construct, [25]). This means that the viral promoter P34 as well as the first 244 amino acid of NS1 and 85 amino acid of NS2 at their amino termini are from MVMp origin whereas the carboxy termini of both NS1 and NS2 proteins as well as the viral promoter P38 and the full VP proteins are from H-1PV origin.

A higher number of cells showing newly-assembled particles in their nucleus were observed among the cell population infected with Del H-1PV compared to the one infected with wild type H-1PV at 15 h and 21 h points of time. In addition, a higher number of cells showing progeny virions that were already released from the nucleus to the cytoplasm, was also observed among the cell population infected with Del H-1PV compared to the one infected with wild type H-1PV 21 h post-infection (FIG. 7, white arrows). Although these data were obtained with the hybrid Del hH-1PV and hybrid wild type hH-1PV, they are in agreement with the above-described faster accumulation of infectious progeny virions in the cytoplasmic fraction of NB-324K cells infected with Del H-1PV compared to those infected with wild type H-1PV (see Example 7 and FIG. 6).

In summary, an earlier nuclear egress of progeny viral particles occurs in cells producing the deletion variant Del hH-1PV (Δ nt 2022-2135) compared to those producing wild type hH-1PV, suggesting that some steps of the Del hH-1PV infectious cycle are progressing faster than those of the wild type H-1PV infectious cycle at least in the reference human NB-324K cell line.

Example 9

The Deletion Mutant Del H-1PV Shows a Lower Cytotoxicity than Wild-Type H-1PV

The cytotoxicity of the deletion mutant Del H-1PV was compared to the one of the wild type H-1PV on NB-324K cells using a clonogenicity assay followed by a crystal violet stain.

As shown in FIG. 8A the amount of cells able to form colonies, i.e., to grow, after infection with the deletion variant H-1PV is somehow higher than the amount of cell colonies detected after infection with wild type H-1PV.

As shown in FIG. 8B, this effect is particularly observed when cells were infected with a low or moderate multiplicity of infection (i.e., 0.5 pfu/cell or 2.5 pfu/cell). Altogether these data indicate a decreased toxicity of the deletion mutant Del H-1PV compared to the toxicity of wild type H-1PV. These are preliminary data; however, the decreased toxicity of the deletion variant Del H-1PV can be correlated with its better production of progeny virions at least in human NB-324K cells. Indeed, these data are in agreement with observations previously made in our laboratory that cell lines that are good producers of progeny virions do not die very fast during the infection process.

In summary, the deletion variant Del H-1PV (Δ nt 2022-2135) exhibits a lower toxicity compared to wild type H-1PV that appears to be in favour of an increased virus production.

Example 10

Increased Virus Production of Del H-1PV in Different Pancreatic Cancer Cell Lines and in HeLa Cells As above-described, a significant advantage of the deletion variant Del H-1PV over the standard wild type H-1PV was observed with respect to infectivity and production rates in the reference human NB-324K cell line. This effect of the Del H-1PV variant was confirmed in various human tumor cell lines.

FIG. 9 shows the amount of infectious particles produced by the deletion variant Del H-1PV compared to the one obtained with wild type H-1PV in human NB-324K, human pancreatic carcinoma Panc-1 and MiaPaCa-2, and human cervix cancer HeLa+ cell lines, as determined by plaque assay at various points of time post-infection.

As shown in FIG. 9, an increased production of infectious progeny virions was observed upon infection with Del H-1PV compared to wild type H-1PV in all tested human cell lines.

In summary, the deletion variant Del H-1PV (Δ nt 2022-2135) exhibits a significant advantage over wild type H-1PV with respect to production rate not only in the human reference cell line NB-324K but also in different pancreatic or cervix cancer cells derived from human tumors.

Example 11

The Deletion Mutant Del H-1PV Shows a Better Efficiency in Suppressing Tumor Growth than Wild-Type H-1PV In addition to the above-described in vitro experiments, the action of the deletion variant Del H-1PV on tumor growth was also investigated in in vivo assays.

FIG. 10A shows a schematic representation of the in vivo assay that was performed. Human pancreatic carcinoma Panc-1 cells were either treated with buffer (mock-treated cells) or infected with Del H-1PV or wt H-1PV at a multiplicity of infection of 1RU/cell (RU, i.e., replication unit, corresponds to a full virus particle that is able to deliver and to amplify its viral genome into a host cell). Mock-treated or parvovirus-infected Panc-1 cells were further injected subcutaneously in Balb/c nude mice as follows: 7 nude mice received mock-treated Panc-1 cells, 7 nude mice received Panc-1 cells infected with wild type H-1PV, and 6 nude mice received Panc-1 cells infected with Del H-1PV variant.

Tumor growth was followed up over an 83-day period of time post injection (FIG. 10B) and the percentage of tumors with a size bigger than 290 mm$^3$ was also determined (FIG. 10C).

The data showed a strong delay in the appearance and growth of parvovirus-infected Panc-1 tumors compared to mock-treated tumors. Moreover, a clear reduced tumor growth was also observed in nude mice that received Del H-1PV-infected Panc-1 tumor cells compared to those injected with wild type H-1PV-infected Panc-1 tumor cells. Indeed, human Panc-1 tumors having a size bigger than 290 mm$^3$ were detected about 10 days later when Panc-1 cells received Del H-1PV compared to those that received wild type H-1PV and less than 20% compared to more than 55% of the human Panc-1 tumors showed a size bigger than 290 mm$^3$ when infected with Del H-1PV compared to wild type H-1PV, respectively, 83 days post-implantation (FIG. 10C).

In summary, the deletion variant Del H-1PV (Δ nt 2022-2135) exhibits a stronger efficiency than wild type H-1PV in suppressing human tumor growth in animals.

Example 12

Intratumoral Injection of Del H-1PV is More Efficient in Suppressing Growth of HeLa Cell-Derived Tumors Compared to Wild Type H-1PV In an in-vivo assay, 2×10$^6$ HeLa cells were injected subcutaneously into the right flank of Balb/c nude mice. 9 days later, when the mice developed HeLa cell-derived tumors, 10$^8$ PFU per mouse (in a volume of 100 μL of PBS) of Del H-1PV or wild type H-1PV were injected near the site of tumor growth, i.e. intratumorally. Tumor growth was monitored up to day 42 post implantation. FIG. 12 shows the action of the deletion variant Del H-1PV on the growth of HeLa cell-derived human cervix carcinoma tumors when injected intratumorally.

An accelerated tumor growth was observed in these conditions, which was probably due to the disruption of the tumor cell mass by the intratumoral injection of the virus. The liquid pressure of the inoculum most probably contributed to a spreading of the tumor cells thereby participating to the strongly accelerated tumor growth. However, improved tumor suppression was still observable in these conditions with Del H-1PV compared to wild type H-1PV. As shown FIG. 12A, the number of mice that developed tumors larger than 1000 mm$^3$ was retarded upon injection of Del H-1PV compared with mock-treated (buffer) or with wild type H-1PV-injected mice. Indeed, 60% of the mice (i.e., 3 mice out of 5) developed tumors larger than 1000 mm$^3$ already at day 6 post-injection when intratumorally injected with wild type H-1PV and only at day 25 post-injection (i.e., almost 20 days later) when intratumorally injected with Del H-1PV.

FIG. 12B shows the survival of mice given in percentage of mice bearing tumors smaller than 1000 mm$^3$ (thereby preventing the sacrifice of the animal) in each group. 80% of the mice (i.e., 4 mice out of 5) that were treated with Del H-1PV survived until day 35 post-injection whereas only 40% of mice (i.e., 2 out of 5) that were treated with wild type H-1PV survived from already day 17 post-injection.

In summary, the deletion variant Del H-1PV (Δ nt 2022-2135) exhibits a stronger capacity than wild type H-1PV in suppressing growth of HeLa cell-derived human tumors in vivo.

Example 13

Increased Neo-Synthesis and Lability of Del NS2P Proteins Compared to Wild Type NS2P Proteins Neo-synthesis and stability of the viral non-structural proteins were determined by pulse-chase labeling and immunoprecipitation assays from NB-324K cells infected with Del H-1PV or wild type H-1PV. FIG. 13 shows the amount of neo-synthesized non-structural NS1 and NS2P proteins after a 30-min period of labeling as well as the remaining amount of these viral proteins within an up to 240-min period of time after their synthesis.

A higher amount of neo-synthesized Del NS1 was detected when compared to neo-synthesized wild type NS1 (FIG. 13, top panel, 0 min of chase). However, the truncated form of NS1 (Del NS1) appeared to be as stable as the wild type form, at least up to a 60-min period of chase. In the case of wild type NS1, an additional and slower-migrating band was slightly detectable at the beginning of the chase period (points 0 and 20 min) and became clearly visible at least from a 40-min to a 240-min period of chase, and which amount increased with time concomitantly with a progressive diminution of the faster migrating form of NS1. This indicates the emergence of some post-translational modification(s) of wild type NS1 that seem to occur progressively and/or temporally. Although not as clearly visible as for wild type NS1, Del NS1 also seemed to migrate as a doublet at least up to a 120-min period of chase whereas only the slower migrating form of Del NS1 was detected after a 240-min period of chase, suggesting different and/or faster-occurring post-translational modifications of the Del NS1 protein when compared to wild type NS1.

As shown FIG. 13 (bottom panel), both synthesis and degradation of the Del NS2P protein were strikingly stimulated when compared to the ones of wild type NS2P. Indeed, although the amount of neo-synthesized Del NS2P protein was much higher than the one of the wild type protein after the labelling period (point 0 min of chase), most of Del NS2P already disappeared after a 60-min period of chase and no more of neo-synthesized Del NS2P was detected after a 240-min chase period whereas neo-synthesized wild type NS2P was still detectable.

In summary, Del NS2P synthesis and turnover are clearly enhanced compared to wild type NS2P. Post-translational modifications of NS1 might also be altered in the truncated (Del) compared to the wild type form of the protein. Altogether, these data strongly suggest that the 114-nt long, in-frame deletion in the Del H-1PV genome and/or the resulting truncation of 37 amino acids in the non-structural Del NS1 and Del NS2 proteins affect some regulatory mechanism(s) of these viral proteins. Whether these alterations would be a key issue in the observed higher infectivity and/or earlier nuclear egress of Del H-1PV progeny virions will be further investigated.

Example 14

Del NS2P is Still Able to Interact with the Nuclear Export Factor Crm1 and with Members of the 14-3-3 Protein Family The ability of the viral proteins to interact with specific cellular proteins was determined by co-immunoprecipitation assays using metabolically $^{35}$S-labelled protein extracts of NB-324K cells infected with Del H-1PV or wild type H-1PV.

As shown FIG. 14A, equivalent amounts of the cellular proteins Crm1 (left panel) and 14-3-3 (right panel) were detected in all tested samples upon immunoprecipitation with the appropriate antibody. In addition, equivalent amounts of wild type NS2 and Del NS2 proteins were found to co-precipitate with either Crm1 or 14-3-3 in the samples prepared in absence of SDS (FIG. 14A, lanes 3 & 5, and lanes 7 & 9, respectively). Co-precipitation of the viral Del NS2 and wild type NS2 proteins with both Crm1 and 14-3-3 was specific as no Del NS2 or wild type NS2 were detected in samples from mock-treated cells (FIG. 14A, lanes 1 & 10) or in samples prepared in presence of SDS, which disrupts protein-protein interaction (FIG. 14A, lanes 2 & 4, and lanes 6 & 8).

FIG. 14B shows that similar amounts of Del NS2 and wild type NS2 proteins were immunoprecipitated from infected samples when using an NS2P-specific antiserum. These data also indicate that only a fraction of the total amount of Del NS2 or wild type NS2 proteins present in the samples was able to interact with either Crm1 or 14-3-3.

In summary, the viral Del NS2 protein interacts with both Crm1 and 14-3-3 cellular products as efficiently as wild type NS2, indicating that the 37-amino acid deletion in the H-1PV NS2 protein sequence did not abrogate the binding properties of the viral protein with its cellular partners and that some conformational structures of H-1PV NS2 were still preserved in the truncated (Del) form.

Example 15

Del H-1PV Virions are More Susceptible to Heat Denaturation than Wild Type H-1PV Virions The decapsidation process of viral genome in infected cells can be mimicked in vitro by a heat denaturation assay. Susceptibility of H-1PV particles to heat denaturation was analysed in vitro by subjecting full virions to various temperatures before determining the amount of viral genomes still present in the samples by quantitative real-time PCR after a DNase treatment followed by an alkaline lysis of the remaining intact virions. As shown FIG. 15, stability of Del H-1PV and wild type H-1PV virions was investigated by exposing purified full particles to temperatures ranging from 50° C. to 70° C. (generated in a PCR machine) for 10 minutes each.

FIG. 15 shows that the amount of Del H-1PV genomes (expressed in % of the total amount) which were recovered upon heat denaturation were lower at all temperatures tested, when compared to the one of wild-type genomes. The temperature that led to the denaturation of 50% of full particles displayed a 2.42° C. difference between Del H-1PV and wild type H-1PV, being of 59.11° C. in the former case and of 61.53° C. in the latter case.

In summary, Del H-1PV particles were more susceptible to heat denaturation than wild type H-1PV particles. This suggests that Del H-1PV viral genomes could be more efficiently decapsidated than wild type H-1PV genomes, which would also be in favour of an increased infectivity of the former ones.

Example 16

Improved Cell Binding and Uptake with Del H-1PV

Binding of full particles to the cell surface was determined by measuring by quantitative real-time PCR the amount of viral genomes recovered from infected NB-324K cells upon incubation for 1 hour at 4° C. to prevent virus internalisation.

Uptake of full particles was investigated by measuring by quantitative real-time PCR the amount of internalised viral genomes at various points of time post infection (ranging from 0.5 hour to 3 hours) from infected cells previously incubated at 37° C. to allow virus entry and treated with trypsin/EDTA to remove plasma membrane-bound viral particles. FIG. 16A shows the percentage of cell membrane-bound full particles whereas FIG. 16B shows the amount of internalised viral genomes both upon infection of NB-324K cells with either Del H-1PV or wild type H-1PV.

As shown FIG. 16A, the percentage of full particles bound to the cell membrane was 9.7-fold higher upon infection with Del H-1PV when compared to wild type H-1PV, indicating that Del H-1PV virions are more susceptible to bind at the plasma membrane of infected cells than wild type H-1PV virions.

As shown FIG. 16B, significantly higher amounts of viral genomes were recovered in all tested cell lysates, i.e., at all tested time of incubation, upon infection with Del H-1PV compared to wild type H-1PV. A nearly 9-fold increase was already observed after 30 min of infection. These data correlate with the above-described better binding efficiency of Del H-1PV virions compared to wild type H-1PV.

In summary, binding at the plasma membrane of Del H-1PV, and as a probable consequence its uptake inside of infected cells, is significantly improved over the wild-type virus. Whether the enhanced binding/uptake together with the above-described higher susceptibility to heat denaturation (Example 15, FIG. 15), and earlier/faster nuclear egress of progeny infectious virions (Example 7, FIG. 6 and Example 8, FIG. 7) of this deletion variant Del H-1PV (A nt 2022-2135) can be due to some subtle modification(s) of the Del H-1PV viral particles will be further investigated.

Example 17

Earlier Replication of Del H-1PV Genome and High Accumulation of Single-Strand DNA in Infected NB-324K Cells Accumulation of the viral replicative forms was analysed by Southern blotting assays using cell extracts from NB-324K cells infected with Del H-1PV or wild type H-1PV. FIG. 17A shows the accumulation of viral monomeric replicative forms (mRF), dimeric replicative forms (dRF) 3 hours, 9 hours, 12 hours, 16 hours, and 24 hours post-infection as a result of a primary infection since infection of cells was performed in presence of neutralizing antibodies to prevent secondary infections during the assay. Signal intensity of each of these viral DNA forms was quantified by Phospho Imager analysis and FIG. 17B shows the Del H-1PV over wild type ratio of the signal intensity of each of these forms at the indicated points of time post-infection.

Both viruses were able to accumulate all viral replicative forms; however, the accumulation pattern of these replicative forms was somehow delayed upon infection with wild type H-1PV compared to Del H-1PV.

In all infected NB-324K cells, no viral replicative form was detectable at the earlier 3-hour point of time. 9 hours post-infection, both mRF and dRF were clearly visible and with a higher intensity upon infection with Del H-1PV compared to wild type H-1PV (FIG. 17A). Indeed, a 7-fold and 11-fold increase in the accumulation of Del H-1PV mRF and dRF, respectively, was measured 9 hours post-infection compared to wild type H-1PV (FIG. 17B). At 12 hours post-infection, both Del H-1PV mRF and dRF were still present in higher amounts than wild type H-1PV mRF and dRF but to a lower extent (with a factor of less than 5x) whereas accumulation of ssDNA, which is a product of a NS1-dependent cleavage of dRF molecules, became significantly detectable in Del H-1PV infected samples reaching a 19-fold increase compared to the accumulation of wild type H-1PV ssDNA. These data indicate a much intense replicative activity in Del H-1PV infected cells 9 hours post-infection which lasted at least up to 12 hours post-infection compared to wild type H-1PV infected cells.

At later points of time post-infection, all three replicative forms were clearly visible in both infected samples (FIG. 17A) with a less than 4-fold (16 h pi) and 2-fold (20 h pi) elevated accumulation of the Del H-1PV replicative forms compared to wild type. These data indicate a replicative activity in the wild type H-1PV infected samples which became more intense between 12 hours and 16 hours post-infection, although still not as high as in Del H-1PV samples, than the ones observed at earlier points of time post-infection.

In summary, replication of the deletion variant Del H-1PV genome (A nt 2022-2135) takes place earlier compared to wild type H-1PV genome replication in NB-324K cells. These data are in agreement with the above-described better efficiency of Del H-1PV virions to bind and enter in NB-324K cells (Example 16 and FIG. 16) as well as the higher susceptibility of Del H-1PV virions to heat denaturation (Example 15, FIG. 15) compared to wild type H-1PV.

Example 18

No Difference in Accumulation of Replicative Forms Upon Transfection of NB-324K Cells with Either Del H-1PV or Wild Type H-1PV Accumulation of Del H-1PV and wild type H-1PV replicative forms was assessed upon transfection of human NB-324K cells with the plasmid construct pDe1H-1PV or pwtH-1PV in presence of neutralizing antibodies, followed by an analysis of transfected samples by Southern blotting assays. This experiment was designed to compare replicative activity of Del H-1PV and wild type H-1PV genome in absence of any earlier step of the parvovirus life cycle that proved to be enhanced with Del H-1PV compared to wild type H-1PV as above-described, in particular cell binding (uptake) (Example 16 and FIG. 16). FIG. 18 shows the accumulation of viral monomeric replicative forms (mRF) and dimeric replicative forms (dRF) 12 hours, 16 hours, and 24 hours post-transfection.

As shown FIG. 18, no significant difference in the appearance and accumulation of viral mRF and dRF molecules was observed at early points of time post-transfection with the plasmid construct pDe1H-1PV compared to pwtH-1PV. *None* of the viral mRF and dRF replicative forms were detectable 12 hours post-transfection. mRF and dRF from both Del H-1PV and wild type H-1PV genomes started to be visible 16 hours post-transfection and the amount of both of them was significantly increased 24 hours post-transfection.

In summary, replication of Del H-1PV genome per se does not take place earlier and/or is not enhanced in transfected NB-324K cells compared to wild type H-1PV genome replication.

Example 19

Increased and/or Faster Release of Del H-1PV Full Virions in the Medium of Transfected NB-324K Cells Compared to the Release of Wild Type H-1PV Full Virions Release of progeny virions was monitored from cell culture supernatants collected 10 hours, 17 hours, and 72 hours after transfection of NB-324K cells with either pDe1H-1PV or pwtH-1PV in presence (+PV1) or not (−PV1) of neutralising antibodies. Viral ssDNA molecules were recovered from supernatant samples by Hirt extraction and detected by Southern blotting analysis. Full and infectious particles which were present in supernatant samples 72 hours post-transfection were quantified by measuring the amount of viral genomes (vg) by quantitative real-time PCR and the amount of plaque-forming units (pfu) by plaque assay, respectively.

FIG. 19 shows that no sssDNA was detectable in the supernatant samples recovered 10 hours and 17 hours post-transfection. 72 hours post-transfection, detectable amounts of ssDNA were recovered from all tested supernatant samples however to a much lower extent from transfection samples performed in presence of neutralizing antibodies, which prevented secondary infections, compared to those performed in absence of neutralizing antibodies, which allowed secondary infections to take place. Yet in both cases, the signal intensity of Del H-1PV progeny ssDNA obtained from the supernatant of transfected 293T cells was higher compared to the one of wild type H-1PV progeny ssDNA. These data indicate that release of Del H-1PV progeny virions is improved when compared to wild type H-1PV, this even in absence of early steps of the virus life cycle (virus binding to cell surface and internalisation, viral genome decapsidation and conversion).

As also shown FIG. 19, Del H-1PV progeny virions present in the supernatants 72 hours post-transfection exhibited a lower P/I ratio when compared to wild type H-1PV. Indeed, the P/I ratio of Del H-1PV progeny virions, which were produced in the presence of neutralising antibodies, was decreased with a factor of up to 21-fold compared to wild type H-1PV.

In summary, Del H-1PV progeny virions are released earlier and/or with a better efficiency in the cell culture medium of transfected cells compared to wild type H-1PV progeny virions. Moreover even when they were produced by transfection, progeny virions of the deletion variant Del H-1PV (Δ nt 2022-2135) exhibited an enhanced infectivity compared to wild type H-1PV.

Example 20

Increased Infectivity of Del H-1PV and Del hH-1PV Produced by Transfection of Human 293T Cells Compared to Wild Type H-1PV and Wild Type hH-1PV The particle-to-infectivity (P/I) ratio of Del H-1PV, Del hH-1PV, wild type H-1PV, wild type hH-1PV was determined from virus stocks that were generated upon transfection of human 293T cells with the appropriate plasmid constructs and recovered from the cell pellets 3 days post-transfection. For each virus stock, the amount of full particles was measured by quantitative real-time PCR, done after DNAse treatment and alkaline lysis of the stocks, in order to determine the number of genome-containing viral particles (given in viral genome (vg) per ml). For each virus stock, the amount of infectious particles was measured by plaque assay in order to determine the capacity of full particles to form plaques (given in plaque forming unit (pfu) per ml) in the reference NB-324K cell line.

As shown FIG. 20, Del H-1PV and Del hH-1PV exhibited a 4.5-fold and 5.8-fold lower P/I ratio than wild type H-1PV and wild type hH-1PV, respectively. This indicates that more infectious particles were produced by the virus stocks generated upon transfection of human 293T cells when the virus contains a 114 nt-long deletion in the NS-coding sequence of their genome.

In summary, both deletion variants Del H-1PV and Del hH-1PV (Δ nt 2022-2135) exhibit a better infectivity even when produced by transfection compared to the wild type H-1PV and hH-1PV.

LIST OF REFERENCES

1 Rommelaere J, Geletneky K, Angelova A L, Daeffler L, Dinsart C, Kiprianova I, Schlehofer J R, Raykov Z.
  Oncolytic parvoviruses as cancer therapeutics.
  Cytokine Growth Factor Rev., 2010, 21: 185-195.
2 Cornelis J J, Salomé N, Dinsart C, Rommelaere J.
  Vectors based on autonomous parvoviruses: novel tools to treat cancer?
  J Gene Med., 2004, 6: S193-202.
3 Bhat R, Dempe S, Dinsart C, and Rommelaere J.
  Enhancement of NK cell anti-tumor responses using an oncolytic parvovirus.
  International Journal of Cancer, 2010, in press [EPub ahead of print]
4 Raykov Z, Grekova S, Galabov A S, Balboni G, Koch U, Aprahamian M, Rommelaere J.
  Combined oncolytic and vaccination activities of parvovirus H-1 in a metastatic tumor model.
  Oncol Rep., 2007, 17: 1493-1499.
5 Raykov Z, Grekova S, Leuchs B, Aprahamian M, Rommelaere J.
  Arming parvoviruses with CpG motifs to improve their oncosuppressive capacity.
  Int J Cancer, 2008, 122: 2880-2884.
6 Rommelaere J, Giese N, Cziepluch C, Cornelis J J.
  Parvoviruses as anticancer agents.
  In: Sinkovics J G, Horvath J C, eds. Viral therapy of human cancers. New-York: Marcel Dekker, 2005, 627p.
7 Rommelaere J, Cornelis J J.
  Antineoplastic activity of parvoviruses.
  J Virol Methods, 1991, 33: 233-251.
8 Cornelis J J, Lang S I, Stroh-Dege A Y, Balboni G, Dinsart C, Rommelaere J.
  Cancer gene therapy through autonomous parvovirus-mediated gene transfer.
  Curr Gene Ther., 2004, 4: 249-261.
9 Wetzel K, Struyf S, Van Damme J, Kayser T, Vecchi A, Sozzani S, Rommelaere J, Cornelis J J, Dinsart C.
  MCP-3 (CCL7) delivered by parvovirus MVMp reduces tumorigenicity of mouse melanoma cells through activation of T lymphocytes and NK cells.
  Int J Cancer, 2007, 120: 1364-1371.
10 Enderlin M, Kleinmann E V, Struyf S, Burrachi C, Vecchi A, Kinscherf R, Kiessling F, Paschek S, Sozzani S, Rommelaere J, Cornelis J J, Van Damme J, Dinsart C.
  TNF-alpha and IFN-gamma-inducible protein 10 (IP-10/CXCL-10) delivered by parvoviral vectors act in synergy to induce antitumor effects in mouse glioblastoma.
  Cancer Gene Ther, 2009, 16: 149-160.
11 Angelova A, Aprahamian M, Grekova S, Hajri A, Leuchs B, Giese N, Herrmann A, Dinsart C, Balboni G, Rommelaere J, Raykov Z. Improvement of gemcitabine-based therapy of pancreatic carcinoma by means of oncolytic parvovirus H-1PV.
  Clinical Cancer Research, 2009, 15: 511-519.
12 Daeffler L, Hörlein R, Rommelaere J, Nüesch J P.
  Modulation of minute virus of mice cytotoxic activities through site-directed mutagenesis within the NS coding region.
  J. Viral., 2003, 77: 12466-12478.
13 Faisst S, Faisst S R, Dupressoir T, Plaza S, Pujol A, Jauniaux J C, Rhode S L, Rommelaere J.
  Isolation of a fully infectious variant of parvovirus H-1 supplanting the standard strain in human cells.
  J. Viral., 1995, 69: 4538-4543.

14 Engelsma D, Valle N, Fish A, Salomé N, Almendral J M, Formerod M.
   A supraphysiological nuclear export signal is required for parvovirus nuclear export.
   Mol Biol Cell, 2008, 19: 2544-2552.
15 Eichwald V, Daeffler L, Klein M, Rommelaere J, Salomë N.
   The NS2 proteins of parvovirus minute virus of mice are required for efficient nuclear egress of progeny virions in mouse cells.
   J. Viral., 2002, 76: 10307-10319.
16 López-Buena A, Valle N, Gallego J M, Pérez J, Almendral J M.
   Enhanced cytoplasmic sequestration of the nuclear export receptor Crm1 by NS2 mutations developed in the host regulates parvovirus fitness.
   J. Virol., 2004, 78: 10674-10684.
17 Rhode S L 3rd, Paradiso P R.
   Parvovirus genome: nucleotide sequence of H-1 and mapping of its genes by hybrid-arrested translation.
   J. Virol., 1983, 45: 173-184.
18 Wrzesinski C, Tesfay L, Salomé N, Jauniaux J C, Rommelaere J, Cornelis J, Dinsart C.
   Chimeric and pseudotyped parvoviruses minimize the contamination of recombinant stocks with replication-competent viruses and identify a DNA sequence that restricts parvovirus H-1 in mouse cells.
   J. Virol., 2003, 77: 3851-3858.
19 Köhler G, Milstein C.
   Continuous cultures of fused cells secreting antibody of predefined specificity.
   Nature, 1975, 256: 495-497.
20 Galfré G, Milstein C.
   Preparation of monoclonal antibodies: strategies and procedures.
   Methods Enzymol., 1981, 73: 3-46.
21 Tattersall P, Bratton J.
   Reciprocal productive and restrictive virus-cell interactions of immunosuppressive and prototype strains of minute virus of mice.
   J. Virol., 46: 944-955.
22 Zolotukhin S, Byrne B J, Mason E, Zolotukhin I, Potter M, Chesnut K, Summerford C, Smulski R J, Muzyczka N.
   Recombinant adeno-associated virus purification using novel methods improves infectious titer and yield.
   Gene Ther, 1999, 6: 973-985.
23 Cornelis J J, Spruyt N, Spegelaere P, Guetta E, Darawshi T, Cotmore S F, Tal J, Rommelaere J.
   Sensitization of transformed rat fibroblasts to killing by parvovirus minute virus of mice correlates with an increase in viral gene expression.
   J. Virol., 1988, 62: 3438-3444.
24 Haag A, Menten P, Van Damme J, Dinsart C, Rommelaere J, Cornelis J J.
   Highly efficient transduction and expression of cytokine genes in human tumor cells by means of autonomous parvovirus vectors: generation of antitumor responses in recipient mice. Hum Gene Ther., 2000, 11: 597-609.
25 Kestler J, Neeb B, Struyf S, Van Damme J, Cotmore S F, D'Abramo A, Tattersall P, Rommelaere J, Dinsart C, Cornelis J J.
   Cis requirements for the efficient production of recombinant DNA vectors based on autonomous parvoviruses.
   Hum Gene Ther., 1999, 10: 1619-1632.
26 Lang S I, Boelz S, Stroh-Dege A Y, Rommelaere J, Dinsart C, Cornelis J J.
   The infectivity and lytic activity of minute virus of mice wild-type and derived vector particles are strikingly different.
   J. Virol., 2005, 79: 289-298.
27 Brockhaus K, Plaza S, Pintel D J, Rommelaere J, Salomé N.
   Nonstructural proteins NS2 of minute virus of mice associate in vivo with 14-3-3 protein family members.
   J. Virol., 1996, 70: 7527-7534.
28 Graham F L, Van Der Eb A J.
   Transformation of rat cells by DNA of human adenovirus 5. Virology, 1973, 54 (2): 536-539.
29 Lacroix J, Leuchs B, Li J, Hristov G, Deubzer H E, Kulozik A E, Rommelaere J, Schlehofer J R, Witt O.
   Parvovirus H1 selectively induces cytotoxic effects on human neuroblastoma cells.
   International Journal of Cancer, 2010, 127(5): 1230-1239.
30 Arad U.
   Modified Hirt Procedure for Rapid Purification of Extrachromosomal DNA from Mammalian Cells.
   BioTechniques, 1998, 24(5), 760-762.

The invention claimed is:

1. A method for treating cancer, comprising the step of administering to a patient a parvovirus variant derived from parvovirus H-1 (H-1PV) or a related rodent parvovirus, wherein said variant (a) has an amino acid substitution at position Lys96 and/or position Leu103 of NS-2 in SEQ ID NO: 13, or (b) has an in-frame deletion consisting of from nucleotides 2022 to 2135 in SEQ ID NO: 11, resulting in the translation of an NS1 protein having a deletion of amino acids 587-624 in SEQ ID NO: 12 and an NS2 protein having a deletion of amino acids 96-133 in SEQ ID NO: 13.

2. The method of claim 1, wherein Lys at position 96 of NS-2 is substituted by a hydrophilic polar amino acid, and/or Leu at position 103 of NS-2 is substituted by Pro.

3. The method of claim 1, wherein Lys at position 96 of NS-2 is substituted by a Glu, and/or Leu at position 103 of NS-2 is substituted by a neutral nonpolar amino acid.

4. The method of claim 1, wherein said variant is characterized by the following substitution(s):
(a) Lys96Glu of NS2; or
(b) Leu103Pro of NS2 and Tyr595H is of NS1.

5. The method of claim 1, wherein said variant (b) has an in-frame deletion consisting of from nucleotides 2022 to 2135 in SEQ ID NO: 11, resulting in the translation of an NS1 protein having a deletion of amino acid residues 587-624 in SEQ ID NO: 12 and an NS2 protein having a deletion of amino acid residues 96-133 in SEQ ID NO: 13.

6. The method of claim 1, wherein said related rodent parvovirus is LuIII, Mouse minute virus (MMV), Mouse parvovirus (MPV), Minute virus of Mice (MVM), Rat minute virus (RMV), Rat parvovirus (RPV), Rat virus (RV), or Kilham rat virus (KRV).

7. The method of claim 1, wherein said cancer is pancreatic carcinoma.

8. The method of claim 1, wherein the parvovirus is derived from H-1PV.

9. The method of claim 1, wherein said cancer is pancreatic carcinoma, cervical carcinoma, hepatoma, or lymphoma.

* * * * *